US012760334B2

(12) United States Patent
Lam et al.

(10) Patent No.: US 12,760,334 B2
(45) Date of Patent: Oct. 13, 2026

(54) METHODS AND COMPOSITIONS FOR EFFICIENT PRODUCTION OF BIOFUELS AND BIOPLASTICS FROM TOXIC FEEDSTOCKS

(71) Applicants: Massachusetts Institute of Technology, Cambridge, MA (US); Whitehead Institute for Biomedical Research, Cambridge, MA (US)

(72) Inventors: Felix Lam, Cambridge, MA (US); Gregory Stephanopoulos, Winchester, MA (US); Gerald Fink, Chestnut Hill, MA (US)

(73) Assignees: Massachusetts Institute of Technology, Cambridge, MA (US); Whitehead Institute for Biomedical Research, Cambridge, MA (US)

( * ) Notice: Subject to any disclaimer, the term of this patent is extended or adjusted under 35 U.S.C. 154(b) by 364 days.

(21) Appl. No.: 18/572,167

(22) PCT Filed: Jun. 23, 2022

(86) PCT No.: PCT/US2022/034720
§ 371 (c)(1),
(2) Date: Dec. 19, 2023

(87) PCT Pub. No.: WO2022/271947
PCT Pub. Date: Dec. 29, 2022

(65) Prior Publication Data

US 2024/0287549 A1 Aug. 29, 2024

Related U.S. Application Data

(60) Provisional application No. 63/214,304, filed on Jun. 24, 2021.

(51) Int. Cl.
*C12P 7/10* (2006.01)
*C12N 9/04* (2006.01)

(52) U.S. Cl.
CPC .............. *C12P 7/10* (2013.01); *C12N 9/0006* (2013.01); *C12Y 101/01028* (2013.01); *C12Y 101/01283* (2013.01)

(58) Field of Classification Search
CPC ......... C12P 7/10; C12N 9/0006; C12N 15/52; C12N 15/81; C12Y 101/01028; C12Y 101/01283; Y02E 50/10
See application file for complete search history.

(56) References Cited

U.S. PATENT DOCUMENTS

| | | | |
|---|---|---|---|
| 2005/0196774 | A1 | 9/2005 | Rozzell et al. |
| 2015/0064759 | A1 | 3/2015 | Perez et al. |
| 2020/0024622 | A1 | 1/2020 | Medoff |

OTHER PUBLICATIONS

Kisselev L., Polypeptide release factors in prokaryotes and eukaryotes: same function, different structure. Structure, 2002, vol. 10: 8-9. (Year: 2002).*

Jayakody et al., Expression of Gre2p improves tolerance of engineered xylose-fermenting *Saccharomyces cerevisiae* to glycolaldehyde under xylose metabolism. Appl. Microbiol. Biotechnol., 2018, vol. 102: 8121-8133. (Year: 2018).*

Lam et al., Engineering alcohol Itolerance in yeast. Science, 2014, vol. 346(6205): 71-75 (Year: 2014).*

Mitsui et al., Construction of lactic acid-tolerant *Saccharomyces cerevisiae* by using CRISPR-Cas-mediated genome evolution for efficient D-lactic acid production. Appl. Microbiol. Biotechnol., 2020, vol. 104: 9147-9158. (Year: 2020).*

Moon et al., Engineered NADH-dependent GRE2 from *Saccharomyces cerevisiae* by directed enzyme evolution enhances HMF reduction using additional cofactor NADPH. Enzyme Microb. Technol ., 2012, vol. 50: 115-120. (Year: 2012).*

Whisstock et al., Prediction of protein function from protein sequence. Q. Rev. Biophysics., 2003, vol. 36 (3): 307-340. (Year: 2003).*

Wishart et al., A single mutation converts a novel phosphotyrosine binding domain into a dual-specificity phosphatase. J. Biol. Chem., 1995, vol. 270(45): 26782-26785. (Year: 1995).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

PCT/US2022/034720, Oct 12, 2022, International Search Report and Written Opinion.

PCT/US2022/034720, Jan. 4, 2024, International Preliminary Report on Patentability.

International Search Report and Written Opinion mailed Oct. 12, 2022, for Application No. PCT/US2022/034720.

International Preliminary Report on Patentability mailed Jan. 4, 2024, for Application No. PCT/US2022/034720.

Lam et al., Engineered yeast tolerance enables efficient production from toxified lignocellulosic feedstocks. Sci Adv. Jun. 25, 2021;7(26):eabf7613.

Abbott et al., Metabolic engineering of *Saccharomyces cerevisiae* for production of carboxylic acids: current status and challenges. FEMS Yeast Res. Dec. 2009;9(8):1123-36. doi: 10.1111/j.1567-1364.2009.00537.x. Epub Jun. 6, 2009.

Ali et al., Emerging technologies for the pretreatment of lignocellulosic materials for bio-based products. Appl Microbiol Biotechnol. Jan. 2020;104(2):455-473. doi: 10.1007/s00253-019-10158-w. Epub Nov. 4, 2019. Erratum in: Appl Microbiol Biotechnol. Jun. 2020;104(11):5159. doi: 10.1007/s00253-020-10629-5.

Allen et al., Furfural induces reactive oxygen species accumulation and cellular damage in *Saccharomyces cerevisiae*. Biotechnol Biofuels. Jan. 15, 2010;3:2. doi: 10.1186/1754-6834-3-2.

Almario et al., Evolutionary engineering of *Saccharomyces cerevisiae* for enhanced tolerance to hydrolysates of lignocellulosic biomass. Biotechnol Bioeng. Oct. 2013;110(10):2616-23. doi: 10.1002/bit.24938. Epub Jul. 11, 2013.

(Continued)

*Primary Examiner* — Ganapathirama Raghu
(74) *Attorney, Agent, or Firm* — Wolf, Greenfield & Sacks, P.C.

(57) ABSTRACT

The present disclosure provides, in various aspects, engineered alcohol tolerant yeast and methods of producing high concentrations of biofuels and bioplastics from toxic feedstocks.

16 Claims, 15 Drawing Sheets

Specification includes a Sequence Listing.

(56) References Cited

OTHER PUBLICATIONS

Almeida et al., Increased tolerance and conversion of inhibitors in lignocellulosic hydrolysates by *Saccharomyces cerevisiae*. Journal of Chemical Technology & Biotechnology: International Research in Process, Environmental & Clean Technology. Apr. 2007;82(4):340-9.

Almeida et al., NADH- vs NADPH-coupled reduction of 5-hydroxymethyl furfural (HMF) and its implications on product distribution in *Saccharomyces cerevisiae*. Appl Microbiol Biotechnol. Apr. 2008;78(6):939-45. doi: 10.1007/s00253-008-1364-y. Epub Mar. 11, 2008.

Alper et al., Tuning genetic control through promoter engineering. Proc Natl Acad Sci U S A. Sep. 6, 2005;102(36):12678-83. doi: 10.1073/pnas.0504604102. Epub Aug. 25, 2005. Erratum in: Proc Natl Acad Sci U S A. Feb. 21, 2006;103(8):3006.

Baek et al., Metabolic engineering and adaptive evolution for efficient production of D-lactic acid in *Saccharomyces cerevisiae*. Appl Microbiol Biotechnol. Mar. 2016;100(6):2737-48. doi: 10.1007/s00253-015-7174-0. Epub Nov. 23, 2015.

Brachmann et al., Designer deletion strains derived from *Saccharomyces cerevisiae* S288C: a useful set of strains and plasmids for PCR-mediated gene disruption and other applications. Yeast. Jan. 30, 1998;14(2):115-32. doi: 10.1002/(SICI)1097-0061(19980130)14:2<115::AID-YEA204>3.0.CO;2-2.

Capaldi et al., Structure and function of a transcriptional network activated by the MAPK Hog1. Nat Genet. Nov. 2008;40(11):1300-6. doi: 10.1038/ng.235. Epub Oct. 19, 20089. Supplemental Information, 43 pages.

Casey et al., Effect of acetic acid and pH on the cofermentation of glucose and xylose to ethanol by a genetically engineered strain of *Saccharomyces cerevisiae*. FEMS Yeast Res. Jun. 2010;10(4):385-93. doi: 10.1111/j.1567-1364.2010.00623.x. Epub Mar. 10, 2010.

Chen et al., DMR (deacetylation and mechanical refining) processing of corn stover achieves high monomeric sugar concentrations (230 g L-1) during enzymatic hydrolysis and high ethanol concentrations (> 10% v/v) during fermentation without hydrolysate purification or concentration. Energy & Environmental Science. 2016;9(4):1237-45.

Cunha et al., Molecular and physiological basis of *Saccharomyces cerevisiae* tolerance to adverse lignocellulose-based process conditions. Appl Microbiol Biotechnol. Jan. 2019;103(1):159-175. doi: 10.1007/s00253-018-9478-3. Epub Nov. 5, 2018.

Flikweert et al., Pyruvate decarboxylase: an indispensable enzyme for growth of *Saccharomyces cerevisiae* on glucose. Yeast. Mar. 15, 1996;12(3):247-57. doi: 10.1002/(SICI)1097-0061(19960315)12:3%3C247::AID-YEA911%3E3.0.CO;2-I.

Heer et al., Identification of furfural as a key toxin in lignocellulosic hydrolysates and evolution of a tolerant yeast strain. Microb Biotechnol. Nov. 2008;1(6):497-506. doi: 10.1111/j.1751-7915.2008.00050.x. Epub Aug. 4, 2008.

Heer et al., Resistance of *Saccharomyces cerevisiae* to high concentrations of furfural is based on NADPH-dependent reduction by at least two oxireductases. Appl Environ Microbiol. Dec. 2009;75(24):7631-8. doi: 10.1128/AEM.01649-09. Epub Oct. 23, 2009.

Hohmann, S., Characterization of PDC6, a third structural gene for pyruvate decarboxylase in *Saccharomyces cerevisiae*. J Bacteriol. Dec. 1991;173(24):7963-9. doi: 10.1128/jb.173.24.7963-7969. 1991.

Ishida et al., The effect of pyruvate decarboxylase gene knockout in *Saccharomyces cerevisiae* on L-lactic acid production. Biosci Biotechnol Biochem. May 2006;70(5):1148-53. doi: 10.1271/bbb.70.1148.

Jönsson et al., Bioconversion of lignocellulose: inhibitors and detoxification. Biotechnol Biofuels. Jan. 28, 2013;6(1):16. doi: 10.1186/1754-6834-6-16.

Jung et al., Dilute acid pretreatment of lignocellulose for whole slurry ethanol fermentation. Bioresour Technol. Mar. 2013;132:109-14. doi: 10.1016/j.biortech.2012.12.151. Epub Jan. 3, 2013.

Klinke et al., Inhibition of ethanol-producing yeast and bacteria by degradation products produced during pre-treatment of biomass. Appl Microbiol Biotechnol. Nov. 2004;66(1):10-26. doi: 10.1007/s00253-004-1642-2. Epub Aug. 6, 2004.

Ko et al., Compounds inhibiting the bioconversion of hydrothermally pretreated lignocellulose. Appl Microbiol Biotechnol. May 2015;99(10):4201-12. doi: 10.1007/s00253-015-6595-0. Epub Apr. 24, 2015.

Lam et al., Biofuels. Engineering alcohol tolerance in yeast. Science. Oct. 3, 2014;346(6205):71-5. doi: 10.1126/science.1257859. Epub Oct. 2, 2014.

Larsson et al., The generation of fermentation inhibitors during dilute acid hydrolysis of softwood. Enzyme and microbial technology. Feb. 1, 1999;24(3-4):151-9.

Lau et al., Cellulosic ethanol production from AFEX-treated corn stover using *Saccharomyces cerevisiae* 424A(LNH-ST). Proc Natl Acad Sci U S A. Feb. 3, 2009;106(5):1368-73. doi: 10.1073/pnas.0812364106. Epub Jan. 22, 2009.

Liu et al., Multiple gene-mediated NAD(P)H-dependent aldehyde reduction is a mechanism of in situ detoxification of furfural and 5-hydroxymethylfurfural by *Saccharomyces cerevisiae*. Appl Microbiol Biotechnol. Dec. 2008;81(4):743-53. doi: 10.1007/s00253-008-1702-0. Epub Sep. 23, 2008.

Ma et al., Alcohol dehydrogenases from *Scheffersomyces stipitis* involved in the detoxification of aldehyde inhibitors derived from lignocellulosic biomass conversion. Appl Microbiol Biotechnol. Sep. 2013;97(18):8411-25. doi: 10.1007/s00253-013-5110-8. Epub Aug. 4, 2013.

Mills et al., Cellulosic hydrolysate toxicity and tolerance mechanisms in *Escherichia coli*. Biotechnol Biofuels. Oct. 15, 2009;2:26. doi: 10.1186/1754-6834-2-26.

Mohd Azhar et al., Yeasts in sustainable bioethanol production: A review. Biochem Biophys Rep. Mar. 6, 2017;10:52-61. doi: 10.1016/j.bbrep.2017.03.003.

Moon et al., Engineered NADH-dependent GRE2 from *Saccharomyces cerevisiae* by directed enzyme evolution enhances HMF reduction using additional cofactor NADPH. Enzyme Microb Technol. Feb. 10, 2012;50(2):115-20. doi: 10.1016/j.enzmictec.2011.10.007. Epub Nov. 9, 2011.

Mosier et al., Features of promising technologies for pretreatment of lignocellulosic biomass. Bioresour Technol. Apr. 2005;96(6):673-86. doi: 10.1016/j.biortech.2004.06.025.

O'Rourke et al., Unique and redundant roles for HOG MAPK pathway components as revealed by whole-genome expression analysis. Mol Biol Cell. Feb. 2004;15(2):532-42. doi: 10.1091/mbc.e03-07-0521. Epub Oct. 31, 2003. Supplemental Information, 4 pages.

Palmqvist et al., Fermentation of lignocellulosic hydrolysates. II: inhibitors and mechanisms of inhibition. Bioresource technology. Aug. 1, 2000;74(1):25-33.

Petersson et al., A 5-hydroxymethyl furfural reducing enzyme encoded by the *Saccharomyces cerevisiae* ADH6 gene conveys HMF tolerance. Yeast. Apr. 30, 2006;23(6):455-64. doi: 10.1002/yea.1370.

Taherzadeh et al., Conversion of furfural in aerobic and anaerobic batch fermentation of glucose by *Saccharomyces cerevisiae*. J Biosci Bioeng. 1999;87(2):169-74. doi: 10.1016/s1389-1723(99)89007-0.

Turner et al., Lactic acid production from cellobiose and xylose by engineered *Saccharomyces cerevisiae*. Biotechnol Bioeng. May 2016;113(5):1075-83. doi: 10.1002/bit.25875. Epub Nov. 20, 2015.

Van Der Pol et al., By-products resulting from lignocellulose pretreatment and their inhibitory effect on fermentations for (bio-)chemicals and fuels. Appl Microbiol Biotechnol. Dec. 2014;98(23):9579-93. doi: 10.1007/s00253-014-6158-9. Epub Nov. 5, 2014.

Varela et al., Osmostress-induced changes in yeast gene expression. Mol Microbiol. Aug. 1992;6(15):2183-90. doi: 10.1111/j.1365-2958.1992.tb01392.x.

Zhang et al., High-titer-ethanol production from cellulosic hydrolysate by an engineered strain of *Saccharomyces cerevisiae* during an in situ removal process reducing the inhibition of ethanol on xylose metabolism. Process Biochemistry. Aug. 1, 2016;51(8):967-72.

(56) References Cited

OTHER PUBLICATIONS

Zhou et al., Xylose isomerase overexpression along with engineering of the pentose phosphate pathway and evolutionary engineering enable rapid xylose utilization and ethanol production by *Saccharomyces cerevisiae*. Metab Eng. Nov. 2012;14(6):611-22. doi: 10.1016/j.ymben.2012.07.011. Epub Aug. 16, 2012.

* cited by examiner

METHODS AND COMPOSITIONS FOR EFFICIENT PRODUCTION OF BIOFUELS AND BIOPLASTICS FROM TOXIC FEEDSTOCKS

CROSS-REFERENCE TO RELATED APPLICATIONS

This application is a national stage filing under 35 U.S.C. § 371 of International PCT Application PCT/US2022/034720, filed Jun. 23, 2022, entitled "METHODS AND COMPOSITIONS FOR EFFICIENT PRODUCTION OF BIOFUELS AND BIOPLASTICS FROM TOXIC FEEDSTOCKS, which claims the benefit under 35 U.S.C. § 119 (e) of U.S. Provisional Application No. 63/214,304, filed Jun. 24, 2021, entitled "METHODS AND COMPOSITIONS FOR EFFICIENT PRODUCTION OF BIOFUELS AND BIOPLASTICS FROM TOXIC FEEDSTOCKS," the entire disclosure of each of which is hereby incorporated by reference in its entirety.

GOVERNMENT SUPPORT

This invention was made with government support under DE-EE0007531 awarded by the U.S. Department of Energy. The government has certain rights in the invention.

REFERENCE TO AN ELECTRONIC SEQUENCE LISTING

The contents of the electronic sequence listing (M065670505US01-SEQ-KVC.txt; Size: 9,230 bytes; and Date of Creation: Dec. 14, 2023) is hereby incorporated by reference in its entirety.

FIELD

Provided herein are methods and compositions related to efficiently producing biofuels from toxic hydrolyzed biomass feedstocks with the use of modified yeast cells.

BACKGROUND

The increased use of renewable transportation fuels such as bioethanol is one of the most widely accepted strategies to combat global climate change. However, the toxicity of ethanol and other alcohols to the industrial production organism, *Saccharomyces cerevisiae*, is a primary factor limiting greater output. The high cell density ("pitch") and very high sugar ("gravity") conditions of large-scale fermentation produce preternaturally high concentrations of ethanol that lead to significant losses in cell viability and productivity. Ethanol tolerance is a complex phenotype with an elusive biological basis; genetic analysis has shown that no single modification is capable of eliciting greater resistance.

Meaningful displacement of greenhouse gas emissions from continued oil consumption requires a renewable feedstock transformable into products fungible with petrofuels and petrochemicals and, importantly, is deployable on a similar scale. Despite the declining cost of carbon-free electricity and rise of emission-free vehicles, studies estimate that this segment will comprise at most 31% of the global fleet by 2040 due to non-road modes of carriage and long average ownership in the established internal combustion fleet (1). As the transportation sector remains the largest generator of carbon dioxide, the sheer number of legacy vehicles necessitates that liquid biofuels play a dominant role in any future energy mix in order to minimize net emissions (2). Lignocellulosic biomass, the largest renewable terrestrial resource, provides a realistic intermediate-term route to sustainable fuel and non-fuel commodities at significant scale when paired with suitable fermentation infrastructure (3). In addition to quantities on the magnitude of fossil carbon, lignocellulose addresses issues such as food-fuel competition and arable land use that beset present-generation feedstocks like corn (4). Fermented fuel products, notably ethanol, can be blended directly into the gasoline supply at 15-85% or chemically dehydrated to ethylene and upgraded into jet fuel (5). However, the severe pretreatments needed to deconstruct the highly recalcitrant plant fibers into fermentable sugars typically result in feedstocks toxic to microorganisms (6-8). Partly saddled by such technical challenges, the U.S. cellulosic ethanol industry has dwindled sharply (a single pre-production plant run by POET-DSM remains) and pretreatment research has refocused on conversions that yield clarified, biocatalyst-friendly substrates (9, 10). Even then, the greater complexities required by these processes have generally increased costs (estimates as high as 30¢/gallon ethanol) as well as eroded scalability and competitiveness (11). Engineering elevated microbial tolerance to the inhibitors released in simpler, but more aggressive, hydrolytic methods would, therefore, address one of the major obstacles impeding greater utilization of cellulosic feedstocks (12-15).

SUMMARY

Ethanol toxicity in yeast *S. cerevisiae* limits the production of biofuels globally, yet its biological underpinnings remain enigmatic. Surprisingly, the present disclosure shows that yeast engineered for enhanced aldehyde reduction together with elevated extracellular potassium and pH are sufficient to enable ethanol production from inhibitor-laden feedstocks produced from biomass. By specifically targeting the universal hydrolysate inhibitors, yeast strains are enhanced to tolerate a broad diversity of highly toxic feedstocks and consistently achieve industrial-scale titers of ethanol.

One aspect of the present disclosure provides a genetically modified yeast cell (modified cell) comprising a first exogenous gene operably linked to a promoter, wherein the first exogenous gene encodes an enzyme having methylglyoxal reductase (GRE2) activity. In some embodiments, the enzyme having GRE2 activity is derived from *Saccharomyces cerevisiae*. In some embodiments, the enzyme having GRE2 activity comprises a sequence having at least 90% identity to the amino acid sequence set forth in SEQ ID NO: 1. In some embodiments, the enzyme having GRE2 activity comprises a sequence set forth in SEQ ID NO: 1. In some embodiments, the enzyme having GRE2 activity comprises at least one substitution mutation at a position corresponding to position P48, I290, and/or D133, relative to SEQ ID NO: 1. In some embodiments, the substitution mutation at the position corresponding to position P48 of SEQ ID NO: 1 is a mutation to serine. In some embodiments, the substitution mutation at the position corresponding to position I290 of SEQ ID NO: 1 is a mutation to valine. In some embodiments, the substitution mutation at the position corresponding to position D133 of SEQ ID NO: 1 is a silent mutation that retains aspartate. In some embodiments, the promoter is selected from the group consisting of pTDH3, pTEF3, and pPDC1.

In some embodiments, the yeast cell is of the genus *Saccharomyces*. In some embodiments, the yeast cell is of the species *Saccharomyces cerevisiae*. In some embodiments, the yeast cell is modified to ferment xylose to ethanol in the absence of glucose.

In some embodiments, the modified cell further comprises a second exogenous gene, wherein the second exogenous gene encodes an enzyme having D-lactate dehydrogenase (D-LDH) activity. In some embodiments, the enzyme having D-LDH activity is derived from *Leuconostoc mesenteroides*. In some embodiments, the enzyme having D-LDH activity comprises a sequence having at least 90% identity to the amino acid sequence set forth in SEQ ID NO: 2. In some embodiments, the enzyme having D-LDH activity comprises a sequence set forth in SEQ ID NO: 2.

Another aspect of the present disclosure provides a method of producing biofuel from toxic biomass or feedstocks produced from biomass comprising contacting the modified cell described herein with a medium comprising a potassium salt and a pH modulator. In some embodiments, the biofuel is ethanol. In some embodiments, the potassium salt is selected from potassium phosphate monobasic ($KH_2PO_4$), potassium bicarbonate ($KHCO_3$), potassium phosphate dibasic ($K_2HPO_4$), potassium chloride (KCl), potassium hydroxide (KOH), and potassium sulfate ($K_2SO_4$). In some embodiments, the potassium salt is $K_2HPO_4$. In some embodiments, the concentration of potassium salt in the medium is between about 15 mM to about 200 mM. In some embodiments, the concentration of potassium salt in the medium is about 50 mM. In some embodiments, the pH modulator is selected from potassium hydroxide (KOH), potassium phosphate dibasic ($K_2HPO_4$), and calcium carbonate ($CaCO_3$). In some embodiments, the pH modulator is $CaCO_3$. In some embodiments, the $CaCO_3$ is in an amount sufficient to maintain, in culture medium, a pH of at least 3.5.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The accompanying drawings are not intended to be drawn to scale. In the drawings. each identical or nearly identical component that is illustrated in various figures is represented by a like numeral. For purposes of clarity, not every component may be labeled in every drawing. In the drawings:

FIG. 1A shows ethanol titers from the prototrophic wildtype (WT) strain FY4/5 fermenting synthetic medium containing 100 mM of the indicated additions: Ac=acetic acid; FF=furfural; FF—OH=2-furanmethanol; HMF=5-hydroxymethyl-furfural; HMF-OH=furan-2,5-dimethanol; K+=50 mM KCl; $K^+$/pH=50 mM KCl and $NH_4OH$ to pH 6. Light gray bars are baseline synthetic medium; medium gray bars (+$K^+$) contain the addition of 50 mM KCl; and black bars (+$K^+$/pH) contain the addition of 50 mM KCl and sufficient $NH_4OH$ to achieve pH 6. FIG. 1B shows conversion of furfural and HMF into their cognate alcohols FF—OH and HMF-OH by the WT or GRE2 over-expression strain after 24 h of fermentation in medium containing elevated $K^+$ and pH buffering, and toxified with a benchmark suite of furfural, HMF, and acetic acid. A=FF. B=HMF. C=FF—OH. D=HMF-OH. FIG. 1C shows ethanol titers correlated with time integrals of viable cell densities from toxified medium containing increasing $K^+$ and/or pH by the GRE2 over-expression strain, WT, or gre2Δ/gre2Δ deletion strain. FIG. 1D shows cell growth, and furfural and HMF depletion, in toxified medium by the WT (Label A), GRE2 over-expression strain (Label B), or $GRE2^{evol}$ over-expression strain (Label C). Label D shows furfural depletion by WT. Label E shows furfural depletion by the GRE2 over-expression strain. Label F shows furfural depletion by the $GRE2^{evol}$ over-expression strain. Label G shows HMF depletion by WT. Label H shows HMF depletion by the GRE2 over-expression strain, and Label I shows HMF depletion by the $GRE2^{evol}$ over-expression strain. Data are mean±standard deviation from 3 biological replicates.

FIG. 2A shows ethanol titers from prototrophic diploid strain FY4/5 after 48 h of fermentation in YSC containing 250 g/L glucose, the indicated inhibitor at 50, 100, or 150 mM, and, optionally, supplemented with 50 mM KCl and $NH_4OH$ to pH 6 (+$K^+$/pH). FIG. 2B shows furfural dose response (reproduced from FIG. 2A) compared to its cognate alcohol 2-furanmethanol (FF—OH). FIG. 2C shows HMF dose response (reproduced from FIG. 2A) compared to its cognate alcohol furan-2,5-dimethanol (HMF-OH).

FIG. 6A shows ethanol titers from prototrophic strains LAMy660 (WT). 661 (GRE2). 663 ($GRE2^{evol}$) after 40 h of fermentation in YSC-Leu containing glucose, inhibitor combinations, and supplements as indicated in the legend. FIG. 6B shows ethanol titers from LAMy660, 663 after 48 h of fermentation in minimal nutrient YNB medium containing glucose, inhibitors, and supplements as indicated. FIG. 6C shows largely unaltered ethanol titers from LAMy660, 663 (brown)

in YSC-Leu, and largely unaltered lactic acid titers from LAMy690, 692 (olive) in YSC-Ura-Leu, after complete fermentation (24 h) under non-inhibitory conditions, demonstrating minimal burden from expression of GRE2$^{evol}$.

Figure 7A:
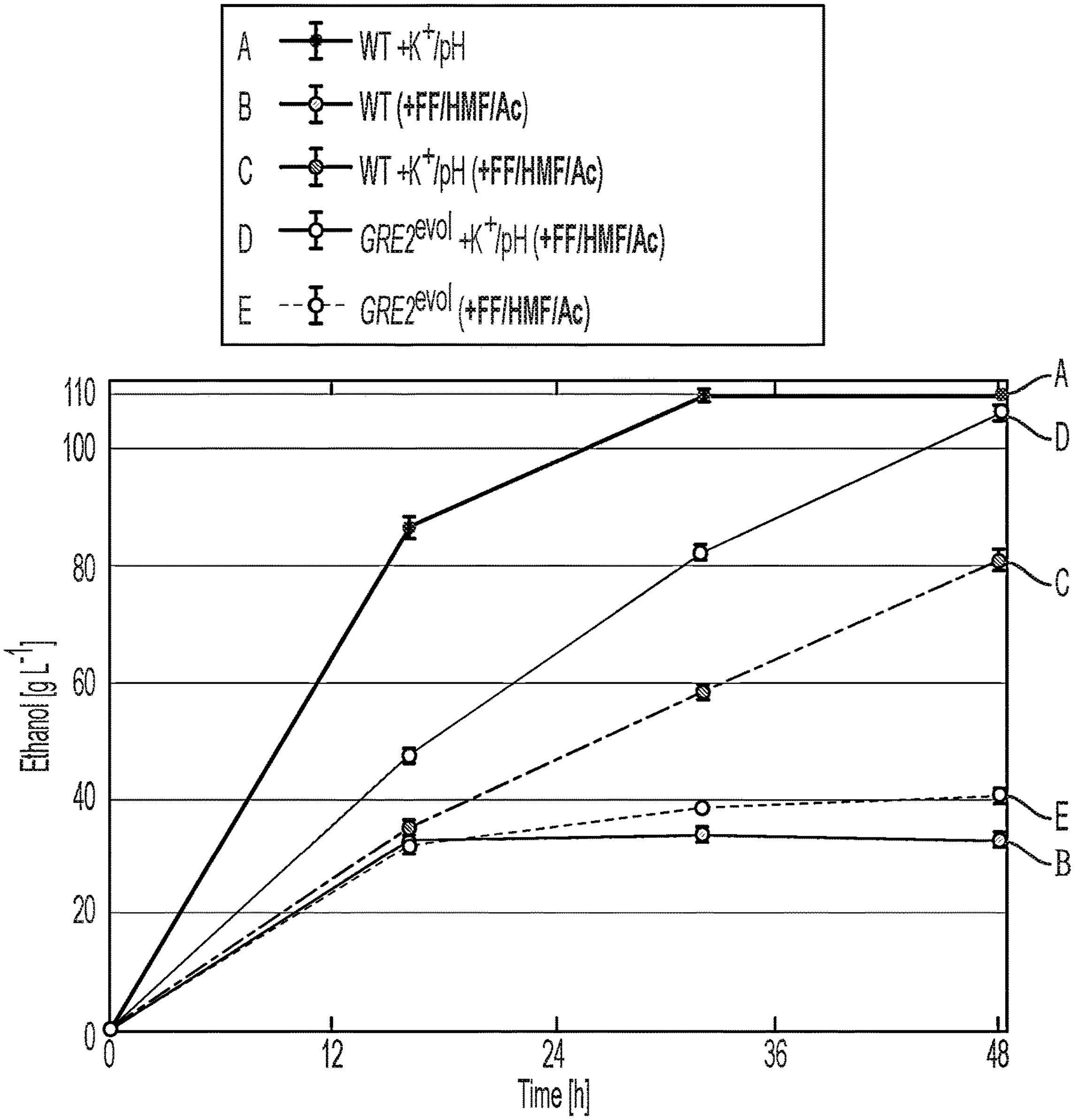
Figure 7B:
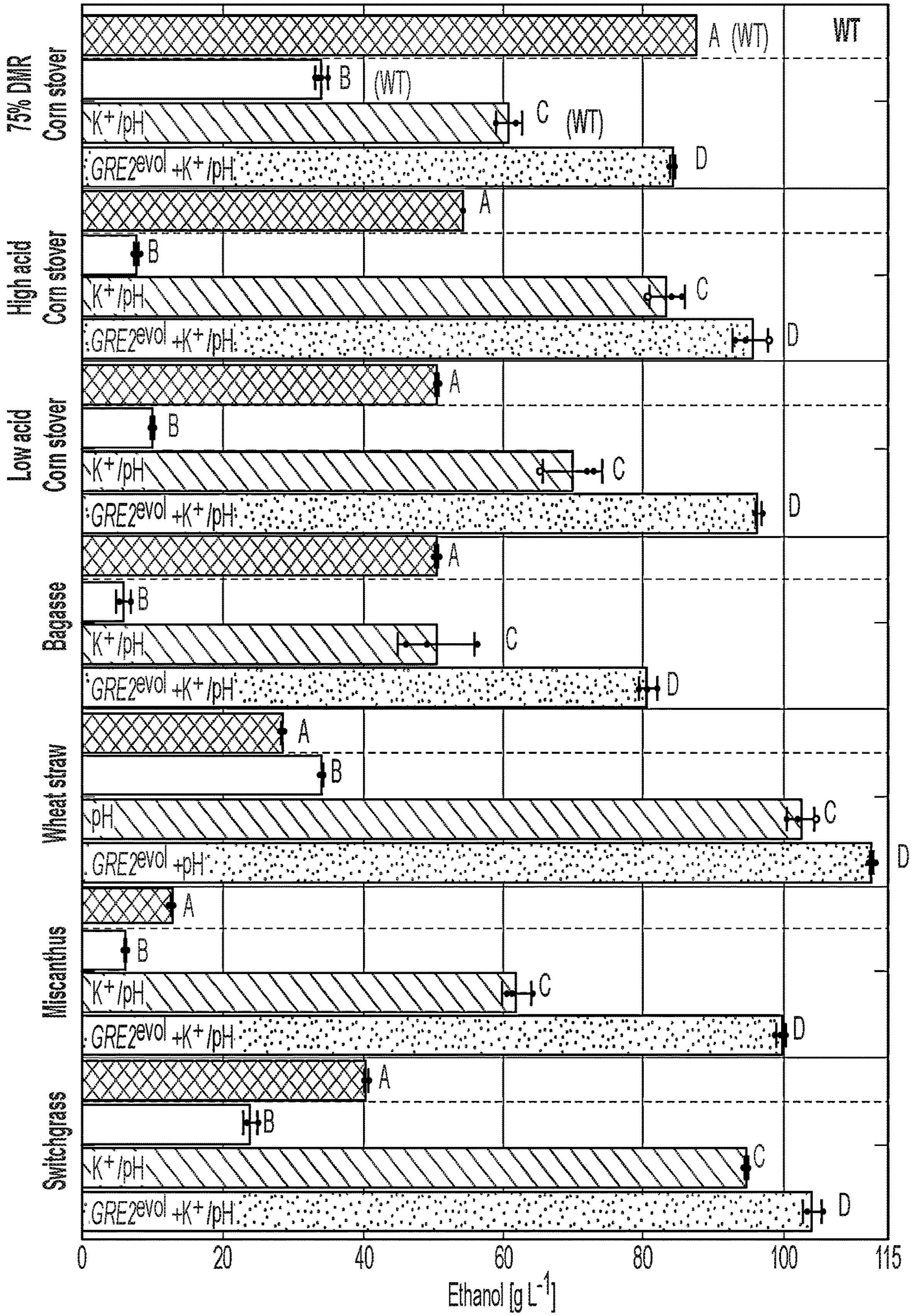

FIGS. 7A-7B. Elevated $K^+$, pH buffering, and GRE2$^{evol}$ over-expression enable near-parity ethanol titers between inhibitor-free and fully toxified conditions, and confer robustness across diverse feedstocks. FIG. 7A shows ethanol production from the WT fermenting synthetic medium supplemented solely with potassium and carbonate buffer (Label A/untoxified control); toxified with the benchmark suite of furfural. HMF, and acetic acid, and adjusted to pH 5 (Label B/WT toxified control); toxified with the benchmark suite of furfural. HMF, and acetic acid, and supplemented with potassium and carbonate buffer (Label C); same as Label C but fermented with the GRE2$^{evol}$ strain (Label D); same conditions as Label B but fermented with the GRE2$^{evol}$ strain (Label E/GRE2$^{evol}$ toxified control). FIG. 7B shows cellulosic ethanol titers from cellulosic hydrolysates where Label A is minimally modified feedstock (urea and adjusted to pH 5 if needed); Label B is toxified with furfural, HMF, acetic acid, and glucose (except no additional glucose in DMR corn stover), and supplemented with urea and adjusted to pH 5 if needed (inhibitor concentrations in Table 2); Label C is the same as Label B but adjusted with potassium and carbonate buffer in lieu of addition with base to pH 5 (Table 2); and Label D is identical to Label C but fermented with the GRE2$^{evol}$ strain. Data are mean±standard deviation from 3 biological replicates.

Figure 8:
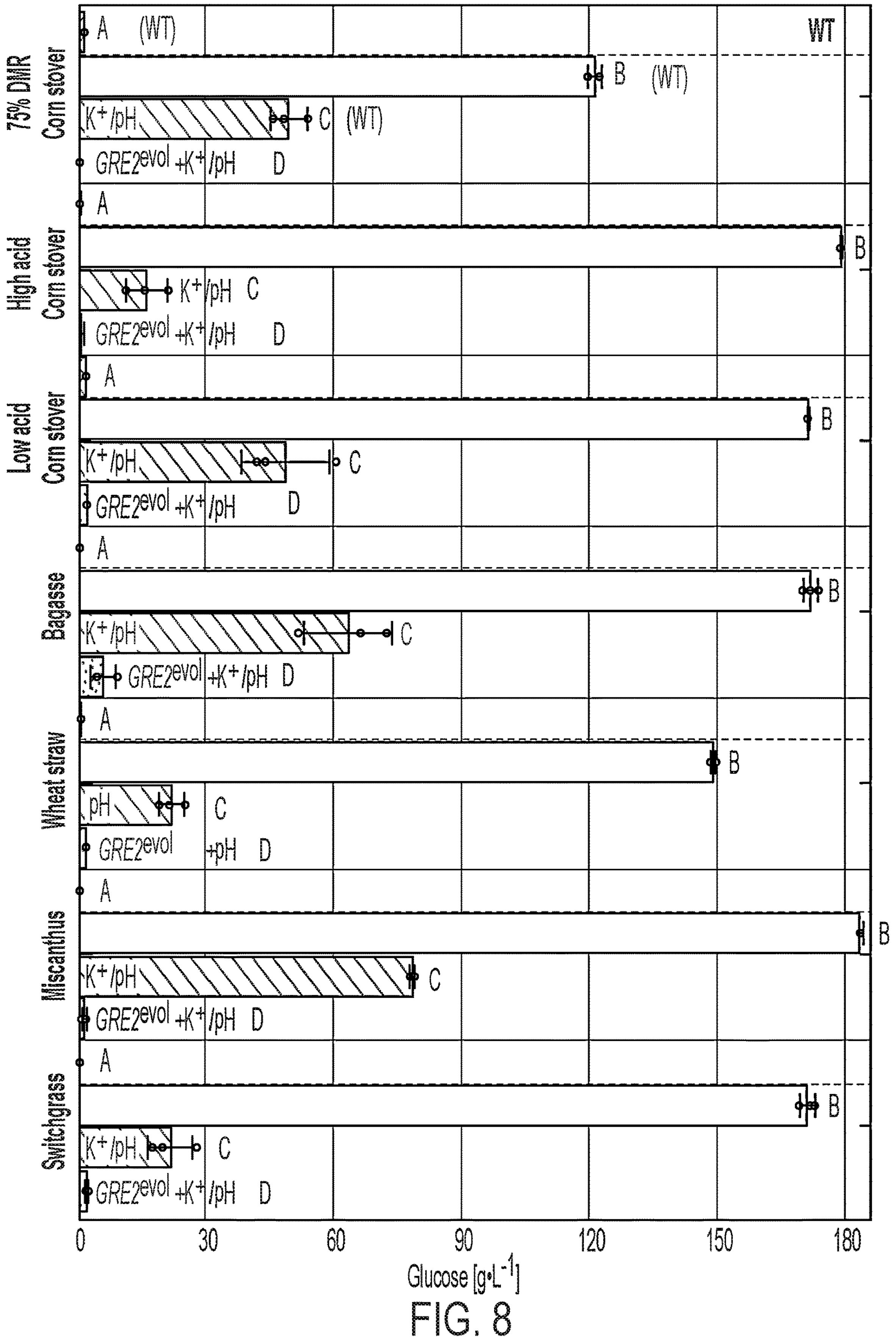

FIG. 8. Elevated $K^+$, pH buffering, and GRE2$^{evol}$ over-expression together enable complete fermentation of glucose in fully toxified cellulosic hydrolysates. Residual glucose from prototrophic strains LAMy660 (WT). 663 (GRE2$^{evol}$) after 52 h of fermentation in hydrolysates toxified to final sugar and inhibitor concentrations as listed for FIG. 7B in Table 2 (fermentation times for the minimally modified controls (Label A) vary from 24-52 h to minimize ethanol consumption in low glucose (<100 g/L) samples). Corresponding ethanol titers shown in FIG. 7B; conditions/bar labels described in caption to FIG. 7B.

Figure 9:
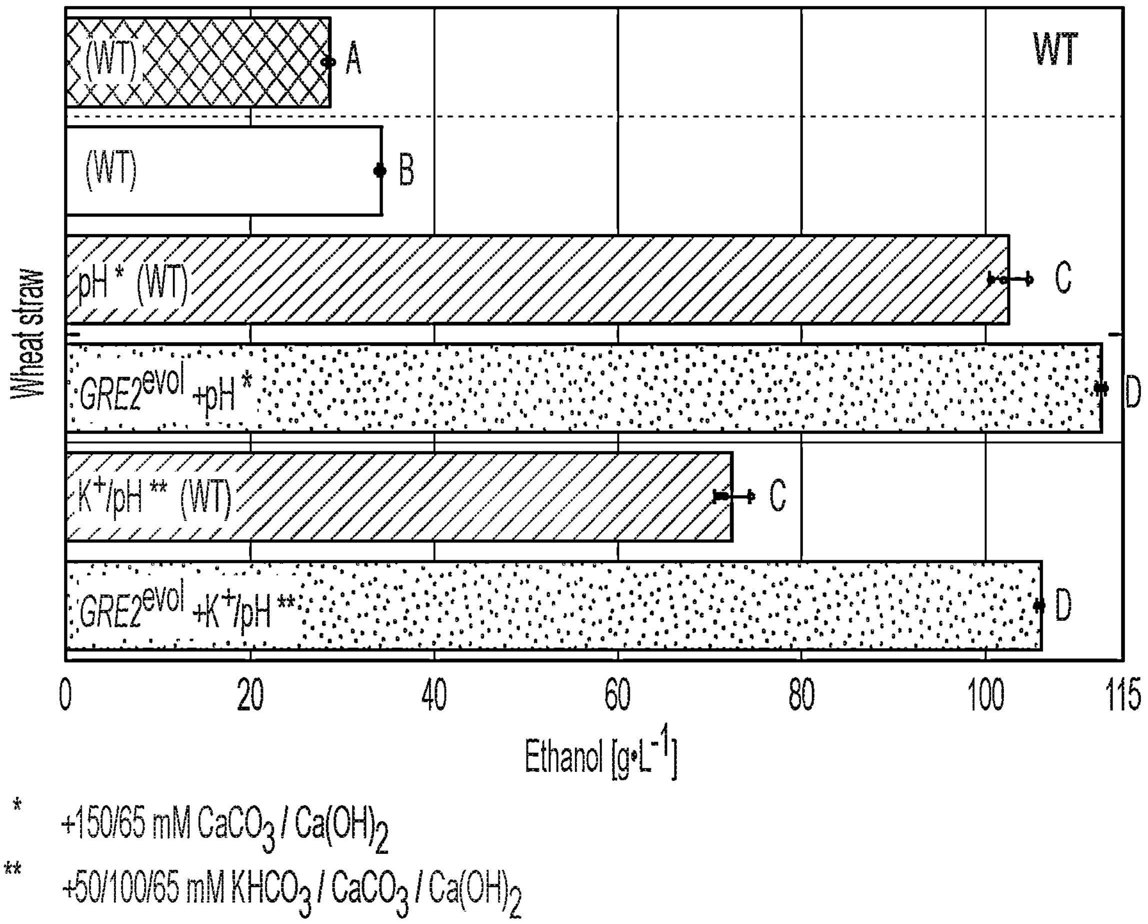

FIG. 9. Informed addition of $K^+$ and cations from buffers or bases for elevating alcohol tolerance is required to avoid exceeding yeast osmotic stress thresholds in wheat straw hydrolysate. Ethanol titers from prototrophic strains LAMy660 (WT). 663 (GRE2$^{evol}$) after 52 h of fermentation (24 h in the minimally modified control (Label A) to minimize ethanol consumption) in hydrolysate toxified to the final sugar and inhibitor concentrations listed for FIG. 7B in Table 2, and adjusted with $CaCO_3$+$Ca(OH)_2$ (single asterisk) or an alternative $KHCO_3$+$CaCO_3$+$Ca(OH)_2$ (double asterisk) that oversupplies $K^+$. Scheme of bars described in caption to FIG. 7B.

Figure 10:
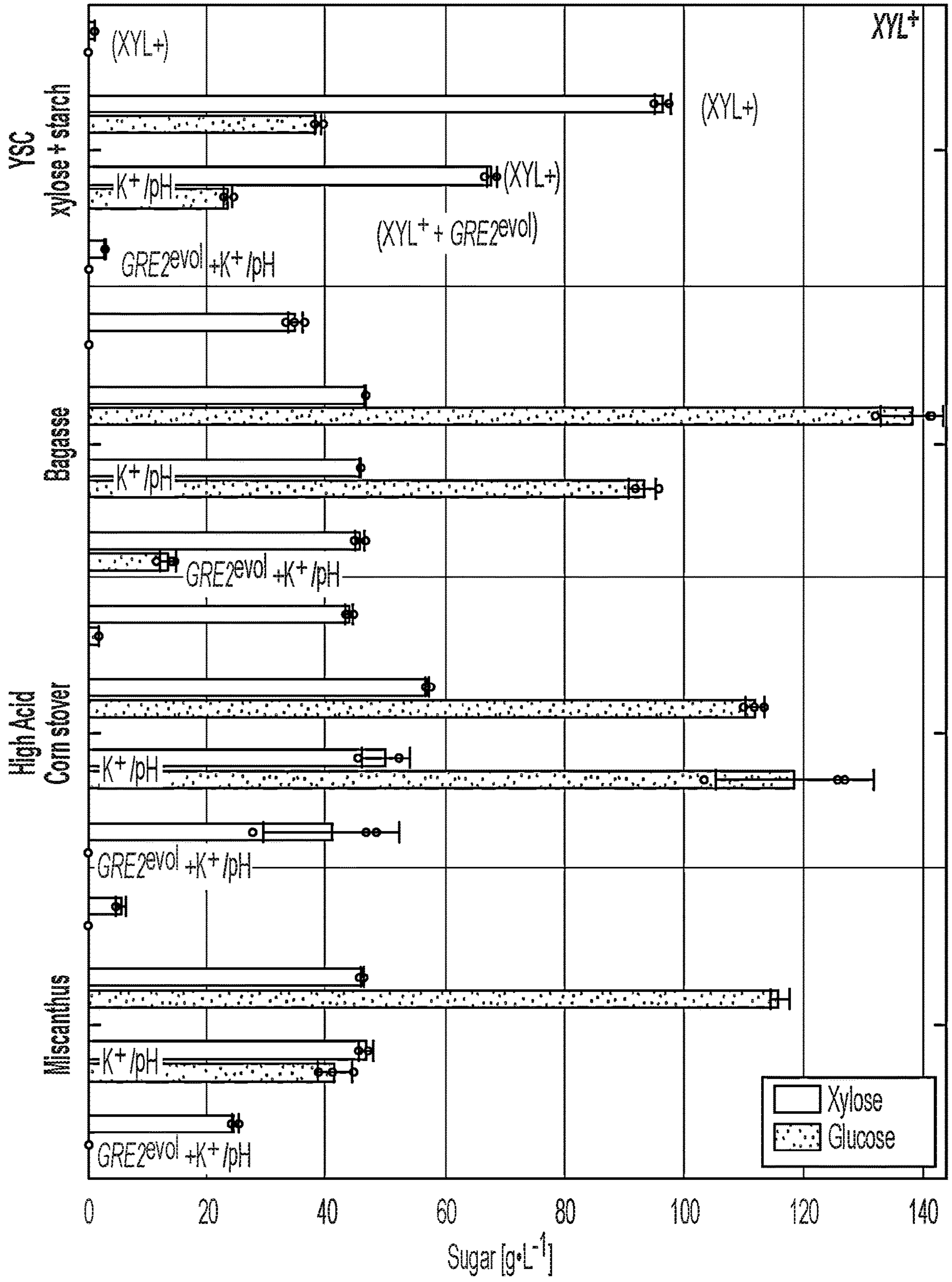

FIG. 10. Consumption of both xylose and glucose by a strain engineered to metabolize xylose (XYL$^+$) is enabled in limiting glucose conditions. Residual xylose and glucose from prototrophic strains LAMy419 (XYL$^+$). 665 (XYL$^+$+GRE2$^{evol}$) after 64-72 h of fermentation (48 h in the minimally modified control to minimize ethanol consumption) in YSC-Ura-Leu-His-Trp-Ade-Lys (bold) containing 50 g/L xylose. 150 g/L starch (slowly hydrolyzed to glucose via amylases), supplemental 60 mM $KHCO_3$ and 140 mM $CaCO_3$, or the indicated biomass hydrolysates (non-bold) toxified to final sugar and inhibitor concentrations as listed for FIG. 11A in Table 2. Corresponding ethanol titers shown in FIG. 11A; ordering of bars within each feedstock follows conditions described in caption to FIG. 7B.

Figure 11A:
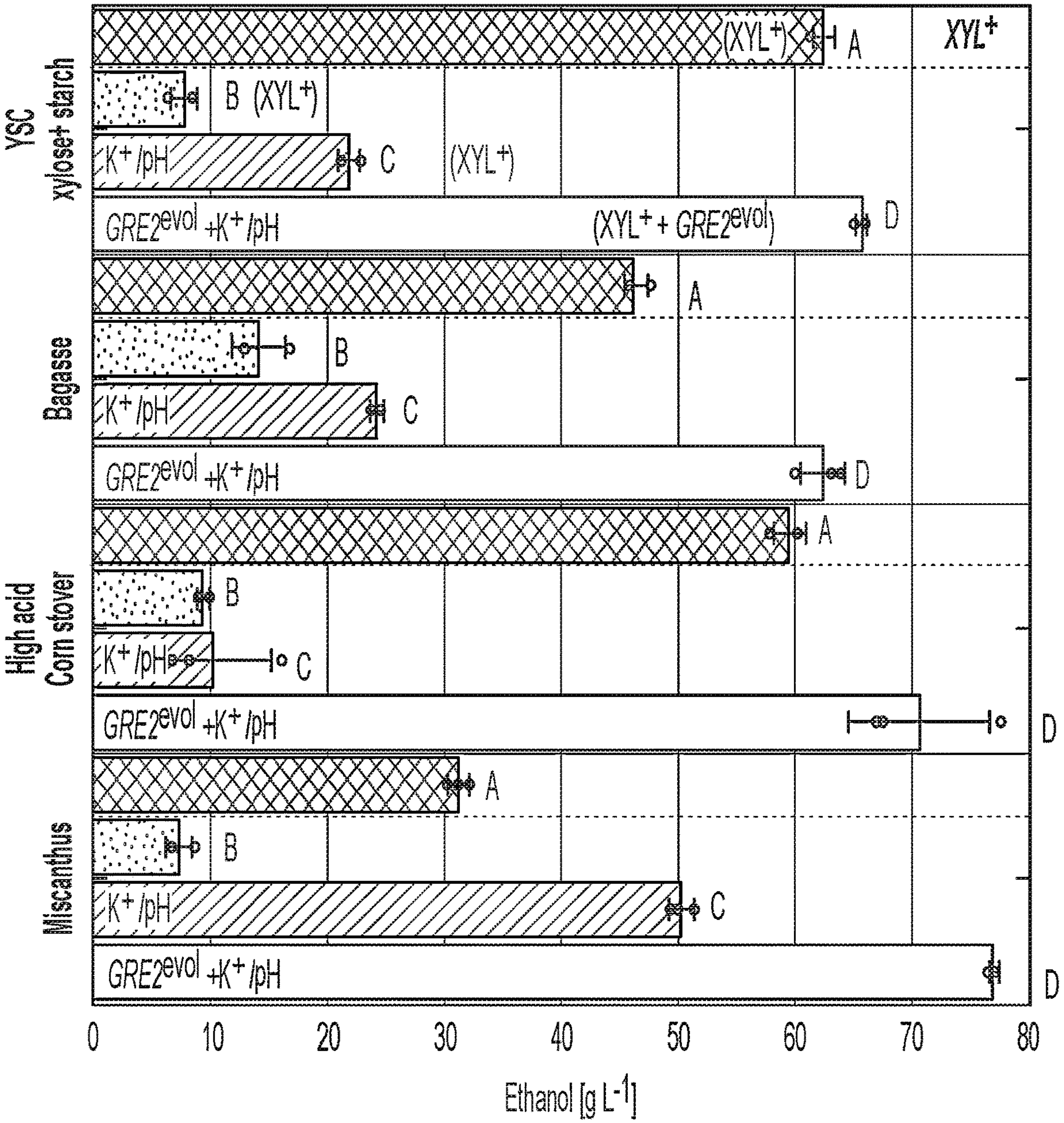
Figure 11B:
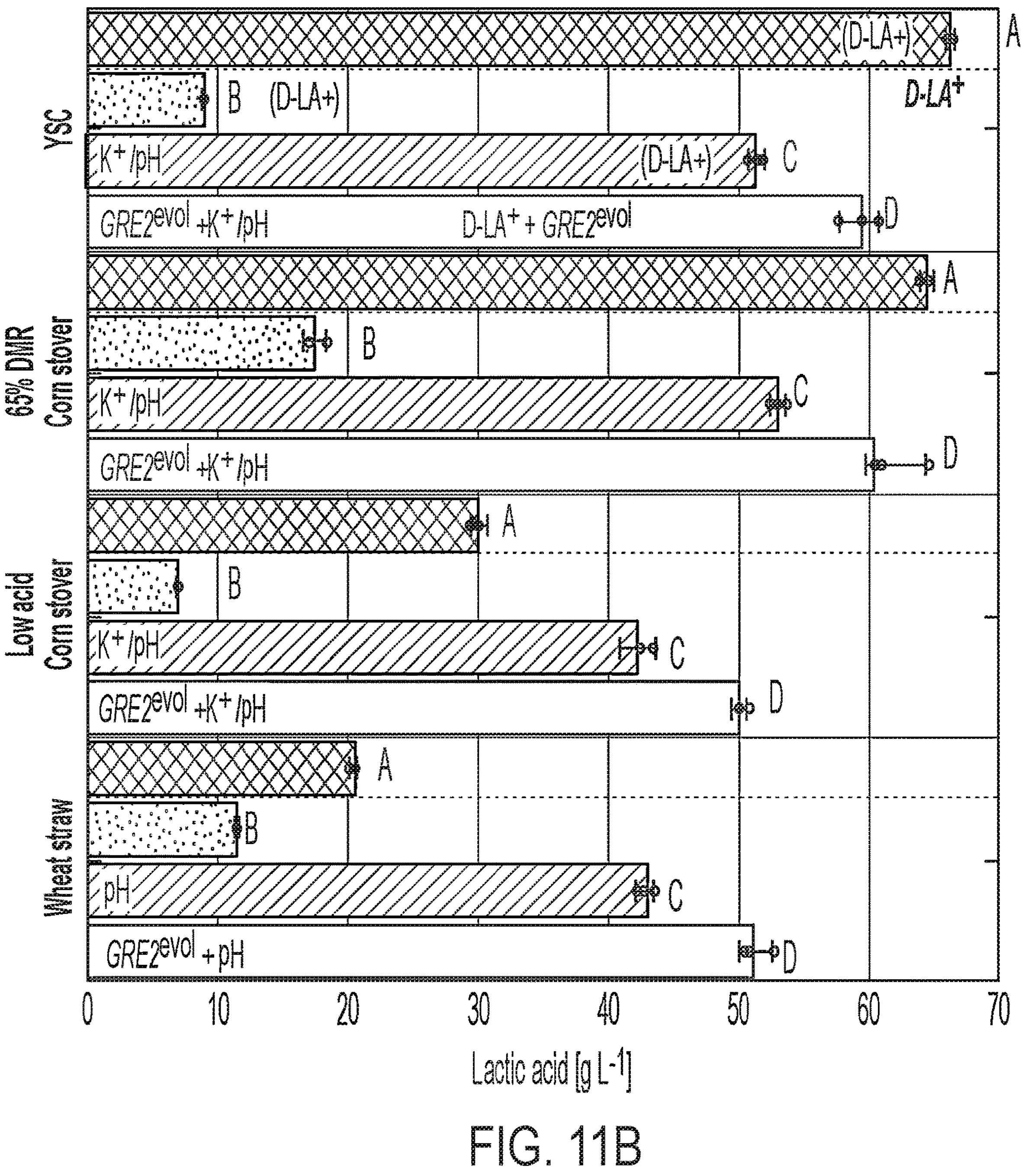

FIGS. 11A-11B. Elevated $K^+$, pH buffering, and GRE2$^{evol}$ over-expression encapsulate a lightweight cellulosic tolerance platform integrable with heterologous engineered pathways. Bars follow the conditions and labels described in FIG. 7B. FIG. 11A shows ethanol titers from a xylose-consuming strain (XYL$^+$) fermenting synthetic medium (bold) containing xylose and starch (slowly hydrolyzed to glucose via amylases), or the indicated biomass hydrolysate (non-bold). FIG. 11B shows cellulosic lactic acid titers from an ethanol-handicapped strain expressing lactate dehydrogenase from *L. mesenteroides* (D-LA$^+$) fermenting synthetic medium (bold) or the indicated biomass hydrolysate (non-bold). Data are mean±standard deviation from 3 biological replicates.

Figure 12:
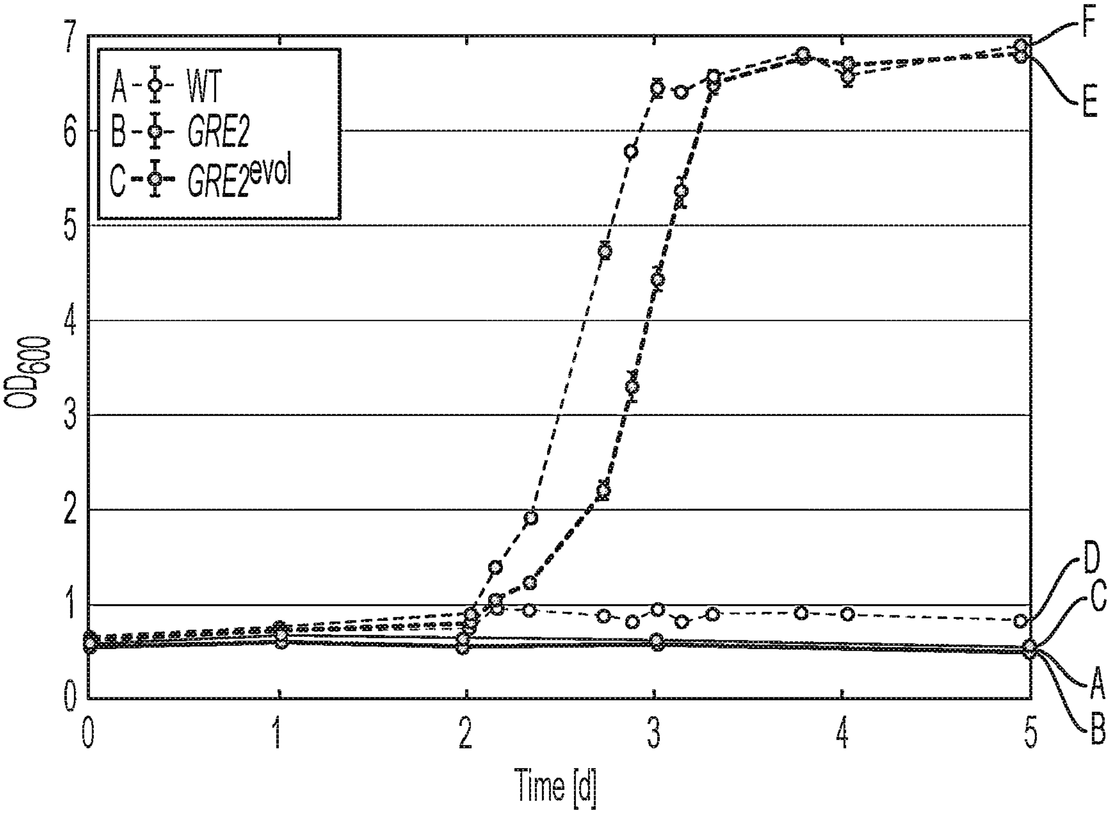

FIG. 12. Toxicity conditions tolerated in fermentation are inhibitory for cell growth. Growth in the WT (Label A and Label D). GRE2 over-expression (Label B and Label E), and GRE2$^{evol}$ over-expression strains (Label C and Label F) in medium toxified to 40/28/55 mM furfural/HMF/acetic acid (dotted lines; reprinted from FIG. 1D) or to the benchmark 62/48/100 mM furfural/HMF/acetic acid used in fermentation (solid lines). Data are mean±standard deviation from 3 biological replicates.

DETAILED DESCRIPTION

Lignocellulosic biomass remains unharnessed for the production of renewable fuels and chemicals due to challenges in deconstruction and the toxicity its hydrolysates pose to fermentation microorganisms. The present disclosure demonstrates in *Saccharomyces cerevisiae* that engineered aldehyde reduction combined with elevated extracellular potassium and pH are sufficient to enable near-parity production between inhibitor-laden and inhibitor-free feedstocks. By specifically targeting the universal hydrolysate inhibitors, a single strain is enhanced to tolerate a broad diversity of highly toxic genuine feedstocks and consistently achieve industrial-scale titers (cellulosic ethanol >100 g/L). Furthermore, a functionally orthogonal, lightweight design enables seamless transferability to existing metabolically engineered chassis strains: full, multi-feedstock tolerance is endowed on a xylose-consuming strain as well as one producing the biodegradable plastics precursor lactic acid. The demonstration of "drop-in" hydrolysate competence enables the potential of cost-effective, at-scale biomass utilization for cellulosic fuel and non-fuel products alike.

The present disclosure demonstrates that a targeted combination of genetic and feedstock modifications is sufficient to enhance a single strain to tolerate a wide variety of highly toxified biomass hydrolysates and deliver cellulosic ethanol with performance comparable to current clean sugar ethanol. This rationally-designed approach is, additionally, highly modular: with introduction of a single gene and no further engineering, feedstock-agnostic hydrolysate tolerance is conferred on or transferred to previously engineered metabolic chassis strains (including one synthesizing a biodegradable plastic) to enable novel cellulosic products beyond ethanol.

The results provided in the present disclosure describe a functionally independent, lightweight platform that both endows yeast with general lignocellulosic hydrolysate tolerance and integrates harmoniously with preexisting metabolically engineered chassis strains. Through systematic characterization of the three dominant and universal toxicities released from biomass pretreatment, the present disclosure demonstrates that tolerance to each inhibitor can be realized through standard acid neutralization (for acetic acid) or conversion of the aldehydes to alcohols which are subsequently ameliorated by elevated $K^+$ and pH treatment (for furfural and HMF). The general practice of hydrolysate tolerance can, therefore, be reduced to two specific and readily modifiable parameters: in a genetic background enhanced by GRE2$^{evol}$ for the accelerated reduction of furfural and HMF, a large diversity of feedstocks-regardless of plant source and/or pretreatment process—can be accommodated via tailored adjustment of $K^+$ and pH. That such a diversity of substrates can be accommodated indicates that the complex spectrum of hydrolytic byproducts other than furfural, HMF, and acetic acid (for example, the various acidic and phenolic inhibitors shown in Table 3) may be qualitatively immaterial. These benefits, collectively, renew and boost the value proposition of cellulosic fermentation. Wide feedstock compatibility can reduce the dependence on specific crop types or pretreatments and, consequently, ameliorate the supply variability (e.g., from seasonality, storage stability) and cost uncertainties surrounding biomass (13). Similarly, heightened tolerance, in addition to harnessing toxic sugar streams or transport-friendlier concentrates, enables production conditions of minimized contaminant growth that would otherwise require the standard-practice, but public health-concerning, use of antibiotics (55). Finally, the targeted specificity of this detoxification approach underlies the high decoupling with native metabolism and straightforward integration with such engineered pathways as those for xylose consumption and lactic acid synthesis. This underscores the notion of a "drop-in" tolerance phenotype extensible to even more non-native capabilities and high-volume biofuels and biochemicals.

Thus, provided herein are furfural and hydroxymethylfurfural (HMF) tolerant yeast cells that are engineered to express a reductase with elevated detoxifying activity toward furfural and HMF. An "engineered" yeast cell refers to a yeast cell that is modified to contain a recombinant or synthetic nucleic acid. As used herein, a "furfural and HMF tolerant yeast cell" refers to an engineered yeast cell with increased viability relative to an unmodified cell (e.g., wild-type "WT" cell) when cultured in the presence of furfural and HMF. It should be understood that, in some instances, the furfural and HMF tolerance (e.g., viability) of a yeast cell may depend on a combination of factors such as, for example, the furfural and HMF concentration and the fermentable sugar concentration in which the yeast cell is cultured.

In some embodiments, the fermentable sugar concentration of the cell culture medium is about 50 g/L to about 400 g/L (e.g., of culture medium). For example, in some embodiments, the fermentable sugar concentration of the cell culture medium is about 50 g/L, about 100 g/L, about 150 g/L, about 200 g/L, about 250 g/L, about 300 g/L, about 350 g/L or about 400 g/L. In some embodiments, the fermentable sugar concentration is more than 400 g/L.

Any yeast capable of fermentation may be used herein. Examples of yeast strains for use in accordance with the present disclosure include, without limitation, the following: *Saccharomyces* spp., *Schizosaccharomyces* spp., *Pichia* spp., Paffia spp., *Kluyveromyces* spp., *Candida* spp., *Talaromyces* spp., Brettanomyces spp., *Pachysolen* spp., Debaryomyces spp., *Yarrowia* spp. and industrial polyploid yeast strains. In some embodiments, the yeast strain is a *Saccharomyces cerevisiae* (*S. cerevisiae*) strain. In some embodiments, the yeast strain is an industrial yeast strain (*S. cerevisiae* strain) used in bioethanol production. An "industrial" yeast strain, as used here, refers to a yeast strain used in the commercial production of alcohol (e.g., ethanol). In some embodiments, an industrial yeast strain is a polyploid strain that has been selected over time for alcohol (e.g., ethanol) productivity and tolerance to alcohol, temperature and/or sugar. For example, in some embodiments, the yeast strain is a sake yeast strain (e.g., strains of *Saccharomyces cerevisiae* such as NCYC 479/Kyokai no. 7), PE-2 or JAY270 (Argueso J L et al. Genome Res. 19(12), 2258-70 (2009), incorporated by reference herein) or Ethanol Red® (Lesaffre Yeast Corporation). Other examples of industrial yeast strains include NCYC 73, NCYC 177, NCYC 431, NCYC 478, NCYC 975 and NCYC 1236.

The furfural and HMF tolerant yeast cells provided herein may be engineered to comprise a modified potassium transport gene encoding a polypeptide (e.g., protein) that increases cellular influx of potassium relative to an unmodified yeast cell and a modified proton transport gene encoding a polypeptide that increases the cellular efflux of protons relative to an unmodified yeast cell. "Cellular influx" of potassium refers to a process by which potassium ions are transported across a cell membrane into the intracellular compartments of a cell. "Cellular efflux" of protons refers to a process by which protons are transported across a cell membrane out of a cell into extracellular space.

An "unmodified yeast cell," as used herein, refers to a yeast cell that is not engineered such as, for example, a wild-type (WT) yeast cell.

The furfural and HMF tolerant yeast cells provided herein may be engineered to comprise a modified NADH- or NADPH-dependent reductase gene encoding a polypeptide (e.g., protein) that decreases the toxicity of furfural and HMF.

A "NADH- or NADPH-dependent reductase gene," as used herein, refers to a gene encoding a polypeptide that functions in the process of irreversibly reducing cytotoxic aldehydes using NADH or NADPH as an electron donor. For example, GRE2 encodes an NADPH-dependent methylglyoxal reductase that can reduce and detoxify furfural and HMF. In some embodiments, the modified cell is engineered to express a wild-type or mutant GRE2 gene.

In some embodiments, the GRE2 enzyme is a GRE2 derived from *Saccharomyces cerevisiae*. The *Saccharomyces cerevisiae* GRE2 corresponds to UniprotKB Accession No. Q12068 and is provided by SEQ ID NO: 1:

```
                                          (SEQ ID NO: 1)
MSVFVSGANGFIAQHIVDLLLKEDYKVIGSARSQEKAENLTEAFGNNPKF

SMEVVPDISKLDAFDHVFQKHGKDIKIVLHTASPFCFDITDSERDLLIPA

VNGVKGILHSIKKYAADSVERVVLTSSYAAVFDMAKENDKSLTFNEESWN

PATWESCQSDPVNAYCGSKKFAEKAAWEFLEENRDSVKFELTAVNPVYVF

GPQMFDKDVKKHLNTSCELVNSLMHLSPEDKIPELFGGYIDVRDVAKAHL

VAFQKRETIGQRLIVSEARFTMQDVLDILNEDFPVLKGNIPVGKPGSGAT

HNTLGATLDNKKSKKLLGFKFRNLKETIDDTASQILKFEGRI
```

A "lactate dehydrogenase gene," as used herein, refers to a gene encoding a polypeptide that functions to convert lactate to pyruvate and back. It also facilitate the reversible reaction of $NAD^+$ to NADH and back. A dehydrogenase is an enzyme that transfers a hydride from one molecule to another.

In some embodiments, the lactate dehydrogenase enzyme is a D-LDH derived from *Leuconostoc mesenteroides*. The

*Leuconostoc mesenteroides* D-LDH corresponds to UniprotKB Accession No. Q2ABS1 and is provided by SEQ ID NO: 2:

```
                                    (SEQ ID NO: 2)
MKIFAYGIRDDEKPSLEEWKAANPEIEVDYTQELLTPETVKLAEGSDSAV

VYQQLDYTRETLTALANVGVTNLSLRNVGTDNIDFDAAREFNFNISNVPV

YSPNAIAEHSMIQLSRLLRRTKALDAKIAKHDLRWAPTIGREMRMQTVGV

IGTGHIGRVAINILKGFGAKVIAYDKYPNAELQAEGLYVDTLDELYAQAD

AISLYVPGVPENHHLINAEAIAKMKDGVVIMNAARGNLMDIDAIIDGLNS

GKISDFGMDVYENEVGLFNEDWSGKEFPDAKIADLISRENVLVTPHTAFY

TTKAVLEMVHQSFDAAVAFAKGEKPAIAVEY
```

In some embodiments, the modified gene (e.g., GRE2 or D-LDH) is operably linked to a promoter. A "promoter," as used herein, refers to a transcription regulatory sequence (nucleic acid sequence) that initiates transcription of an RNA molecule from the DNA downstream of it. In some embodiments, the promoter operably linked to GRE2 or D-LDH is a TDH3 promoter (pTDH3), TEF3 promoter (pTEF3), or a PDC1 promoter (pPDC1).

A "modified" gene, as used herein, refers to a gene that is mutated, overexpressed or misexpressed. In some embodiments, the mutation is a deletion mutation, or a deletion. A "deletion mutation" refers to a region of a chromosome that is missing (i.e., loss of genetic material), which affects the function of a gene, or gene product (e.g., polypeptide encoded by the gene). Any number of nucleotides can be deleted. In some embodiments, a deletion mutation may render a gene, or gene product, non-functional. The symbol "Δ" denotes a deletion mutation. For example, engineered gre2Δ/gre2Δ yeast have deletion mutations in homologous alleles of GRE2. Methods of introducing genetic mutations in yeast are well-known, any of which may be used in accordance with the present disclosure (Sherman, F. in Encyclopedia of Molecular Biology and Molecular Medicine (Meyers, R. A.) 6, 302-325 (Wiley-Blackwell, 1998); Orr-Weaver, T. L., et al. Proc Natl Acad Sci USA 78, 6354-6358 (1981); Sikorski, R. S. & Hieter, P. Genetics 122, 19-27 (1989); and Wach, A., et al. Yeast 10, 1793-1808 (1994), each of which is incorporated by reference herein). A modified gene, or gene product, is herein considered to be "overexpressed" if the expression levels of the gene, or gene product, are increased relative to the expression levels of an unmodified (e.g., wild-type) gene, or gene product. A modified gene, or gene product, is herein considered to be "misexpressed" if the gene, or gene product, is expressed at a cellular location where or at a developmental time when it is not normally expressed. Methods of overexpression and misexpression in yeast are well-known, any of which may be used in accordance with the present disclosure (Mumberg, D., et al. Gene 156, 119-122 (1995); and Mumberg, D., et al. Nucleic Acids Res 22, 5767-5768 (1994), each of which is incorporated by reference herein).

Ethanol resistance is increased substantially and concomitantly with ethanol production under the high sugar (e.g., 300 g/L) and high cell density (e.g., $OD_{600}$~20-30) conditions that are typical of large-scale industrial fermentation. As used herein, "industrial fermentation" refers to the use of fermentation by yeast to produce useful products such as biofuel (e.g., ethanol, or bioethanol). A fermentation process (e.g., conversion of sugar to alcohol) is herein considered to be "large-scale" if the process includes culturing fermenting yeast cells (e.g., engineered yeast cells) in a volume of at least 5 liters (L) (e.g., of culture medium). In some embodiments, a large-scale industrial fermentation process may include culturing fermenting yeast cells in a volume of at least 10 L, at least 15 L, at least 20 L, at least 25 L, at least 50 L, at least 100 L, at least 500 L, at least 1,000 L, at least 5,000 L or at least 10,000 L. In some embodiments, a large-scale industrial fermentation process may include culturing fermenting yeast cells in a volume of at least 100,000 L, at least 500,000 L, or at least 1,000,000 L. The yeast cells may be cultured in, for example, shake flask cultures or bioreactors.

Industrial fermentation processes may also include culturing yeast in the presence of a high concentration of fermentable feedstock or fermentable sugar. "Fermentable feedstock" herein refers to feedstock that can be converted (e.g., by yeast) to sugar and then to alcohol or other engineered end-products. Non-limiting examples of a fermentable feedstock include lignocellulosic biomass (e.g., (corn stover, sugarcane bagasse, straw), composed of carbohydrate polymers (e.g., cellulose, hemicellulose) and an aromatic polymer (e.g., lignin) A "fermentable sugar" herein refers to a sugar that can be converted (e.g., by yeast) to alcohol or other engineered end-products. Examples of fermentable sugars for use in accordance with the present disclosure include, without limitation, allose, altrose, glucose, mannose, gulose, idose, galactose, talose, psicose, fructose, sorbose, tagatose, arabinose, lyxose, ribose, xylose, ribulose and xylulose. Sources of fermentable sugars include, without limitation, feedstock such as corn, wheat, sorghum, potato, sugarbeet, sugarcane, potato-processing residues, sugarbeet, cane molasses and apple pomace. Fermentable sugars can be produced directly or derived from polysaccharides such as cellulose and starch. In some embodiment, the fermentable sugar is from (e.g., derived from) a lignocellulosic substance. Thus, in some embodiments, the fermentable sugar is a hexose such as glucose. In some embodiments, the fermentable sugar is from xylan hemicellulose. Xylose can be recovered by acid or enzymatic hydrolysis. Thus, in some embodiments, the fermentable sugar is a pentose such as xylose. Enzymatic hydrolysis using mixtures of enzymes, such as cellulase and hemicellulases, may be used herein to minimize the destruction of sugars associated with higher severity pretreatments (e.g., concentrated acid hydrolysis) of lignocellulosic material. These enzymes, when combined with effective pretreatment of lignocellulosics, provide high yields of glucose, xylose, and other fermentable sugars with minimal sugar losses.

High concentrations of fermentable sugars include concentrations that are about 100 g/L to about 400 g/L. Thus, in some embodiments, the yeast (e.g., engineered yeast) is cultured in medium having a fermentable sugar concentration of at least 100 g/L. In some embodiments, the yeast is cultured in medium having a fermentable sugar concentration of about 100 g/L to about 400 g/L. For example, in some embodiments, the yeast is cultured in medium having a fermentable sugar concentration of 100 g/L, 150 g/L, 200 g/L, 250 g/L, 300 g/L. 350 g/L or 400 g/L.

Industrial fermentation processes may also include culturing yeast at a high cell density. Thus, in some embodiments, the yeast (e.g., engineered yeast) is cultured at a cell density of about $1\times10^6$ to about $1\times10^9$ viable cells/ml. For example, in some embodiments, the yeast is cultured at a cell density of about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, about $1\times10^8$, about $2\times10^8$, about $3\times10^8$, about $4\times10^8$, about $5\times10^8$, about $6\times10^8$, about $7\times10^8$, about $8\times10^8$, about $9\times10^8$ or about $1\times10^9$ viable cells/ml.

In some embodiments, the yeast (e.g., engineered yeast) is cultured at an optical cell density, measured at a wavelength of 600 nm, of about 1 to about 150 (i.e., $OD_{600}$ is about 1 to about 150). For example, in some embodiments, the $OD_{600}$ of a cell culture containing fermenting yeast cells is about 1, about 5, about 10, about 15, about 20, about 25, about 30, about 35, about 40, about 45, about 50, about 55, about 60, about 70, about 75, about 80, about 85, about 90, about 95, about 100, about 110, about 120, about 130, about 140, about 150. In some embodiments, the $OD_{600}$ of a cell culture containing fermenting yeast cells is about 20 to about 30.

In accordance with the present disclosure, the yeast (e.g., engineered yeast) may be cultured in standard laboratory synthetic complete medium with nutrient drop-out for selection when appropriate (Sherman, F. Meth Enzymol 350, 3-41 (2002), incorporated by reference herein). For example, yeast synthetic complete (YSC) medium may contain a nitrogen base without amino acids and ammonium sulfate (e.g., BD-Difco Yeast Nitrogen Base catalog #233520) with or without nutrients. In some embodiments, the culture medium is adjusted for $K^+$, $H^+$ and/or $Na^+$ concentration.

The present disclosure also provides methods of ethanol production that comprise culturing yeast cells in culture medium that comprises fermentable feedstock and a potassium salt selected from potassium phosphate monobasic ($KH_2PO_4$ or K-Pi), potassium phosphate dibasic ($K_2HPO_4$), potassium bicarbonate ($KHCO_3$), and potassium sulfate ($K_2SO_4$).

The potassium salt may be present in the culture medium in an amount sufficient to produce at least 100 g/L, or at least 150 g/L ethanol. In some embodiments, the potassium salt is in an amount sufficient to produce about 100 g/L to about 300 g/L of ethanol. For example, in some embodiments, the potassium salt is in an amount sufficient to produce about 100 g/L, about 150 g/L, about 200 g/L, about 250 g/L or about 300 g/L.

In some embodiments, the culture medium further comprises potassium hydroxide (KOH), which is present in an amount sufficient to maintain, in the culture medium, a pH of at least 3. Thus, in some embodiments, KOH may be used to adjust the pH of culture medium comprising a potassium salt such as, for example, KCl. In some embodiments, KOH is used to adjust the pH of the culture medium to about 3, about 3.5, about 4, about 4.5, about 5, about 5.5, about 6, about 6.5, about 7, about 7.5 or about 8. In some embodiments, the pH of culture medium (e.g., containing KCl) is adjusted or maintained at a pH within a range of 3 to 8 or about 3 to about 8 (e.g., a pH of 3, 3.5, 4, 4.5, 5, 5.5, 6, 6.5, 7, 7.5 or 8).

In some embodiments, the culture medium further comprises calcium carbonate ($CaCO_3$), which is present in an amount sufficient to maintain, in the culture medium, a pH of at least 3. Thus, in some embodiments, $CaCO_3$ may be used to adjust the pH of culture medium comprising a potassium salt such as, for example, $KHCO_3$. In some embodiments, $CaCO_3$ is used to adjust the pH of the culture medium to about 3, about 3.5, about 4, about 4.5, about 5, about 5.5, about 6, about 6.5, about 7, about 7.5 or about 8. In some embodiments, the pH of culture medium (e.g., containing $KHCO_3$) is adjusted or maintained at a pH within a range of 3 to 8 or about 3 to about 8 (e.g., a pH of 3, 3.5, 4, 4.5, 5, 5.5, 6, 6.5, 7, 7.5 or 8).

The concentration of potassium salt in the culture medium may be about 15 mM to about 200 mM. For example, in some embodiments, the concentration of potassium salt in the culture medium is about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 150 mM, or about 200 mM. In some embodiments, the concentration of potassium salt in the culture medium is about 25 to about 50 mM, about 35 to about 65 mM, or about 50 mM to about 75 mM.

EXAMPLES

In order that the invention described in the present disclosure may be more fully understood, the following examples are set forth. The examples described in this application are offered to illustrate the systems and methods provided in the present disclosure and are not to be construed in any way as limiting in their scope.

Example 1: Generation of Engineered Yeast for Efficient Biofuel Production from Toxic Feedstocks Prior research conducted by the inventors of the present disclosure has demonstrated that in yeast *Saccharomyces cerevisiae*, responsible for the current global output of biofuel ethanol, increases in media potassium ($K^+$) and pH were sufficient to strengthen membrane potential and enhance production universally across laboratory and industrial strains (16). Therefore, the impact of these extracellular adjustments on the fermentation of toxic lignocellulosic feedstocks was investigated. Unrefined hydrolysates of all cellulosic biomass, particularly those pretreated under acidic conditions, contain a spectrum of inhibitory byproducts but are dominated by the furan aldehydes furfural and 5-hydroxymethyl-furfural/HMF (from dehydration of pentoses and hexoses, respectively), and acetic acid (from deacetylation of hemicellulose) (17-23).

Figure 1A:
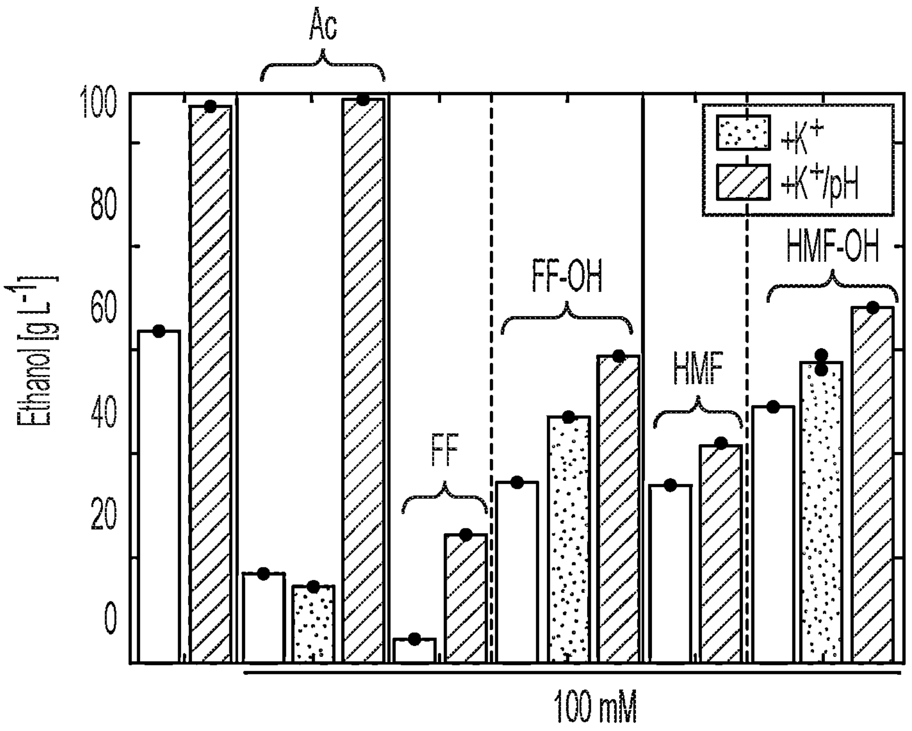
FIGS. 1A-1D. Elevated extracellular $K^+$ and pH combined with GRE2 over-expression confer tolerance to lignocellulosic hydrolysate toxicity.

To systematically characterize the impact of these constituent toxicities, ethanol production was assessed in yeast synthetic complete medium (YSC) with the 3 inhibitors added individually at equimolar concentration. As a completely chemically-defined formulation with trace vitamins, minerals, and amino acids, YSC lacks the undefined extracts contained in "rich" media that could supply unknown components to boost or hinder tolerance. A diploid prototroph of laboratory strain S288C was used to preclude nutrient liabilities, and fermentations conducted for 48 h at 30° C. under high pitch (cell density of $OD_{600}$=20) and high gravity (250 g/L glucose) conditions to mimic industrial production (24). Compared to an ethanol titer of 64±0.2 g/L in unmodified YSC, the presence of 100 mM acetic acid (Ac), furfural (FF), or HMF (HMF) reduced production respectively to 17±0.1, 4±0.3, and 34±0.3 g/L, establishing furfural as the most deleterious component (FIG. 1A. light gray bars) (25). Based on prior tolerance research, each solution was supplemented with 50 mM potassium chloride (KCl) and ammonium hydroxide ($NH_4OH$) to achieve pH 6, and widely varying recoveries were observed (FIG. 1A, +$K^+$/pH black bars). For acetic acid, these additions restored production to 109±0.6 g/L, effectively matching that of $K^+$/pH-elevated YSC. Indeed, the prevalence of acetate salt at pH values sufficiently above its pKa of 4.76 completely abolished toxicity and, over a concentration range applicable to genuine hydrolysates, the salt was fully tolerated by yeast (FIG.

2A) (17, 26). Moreover, a control supplemented solely with KCl provided no amelioration, demonstrating that acetic acid tolerance arises entirely from acid neutralization (FIG. 1A, $+K^+$ medium gray bars).

Figure 1B:
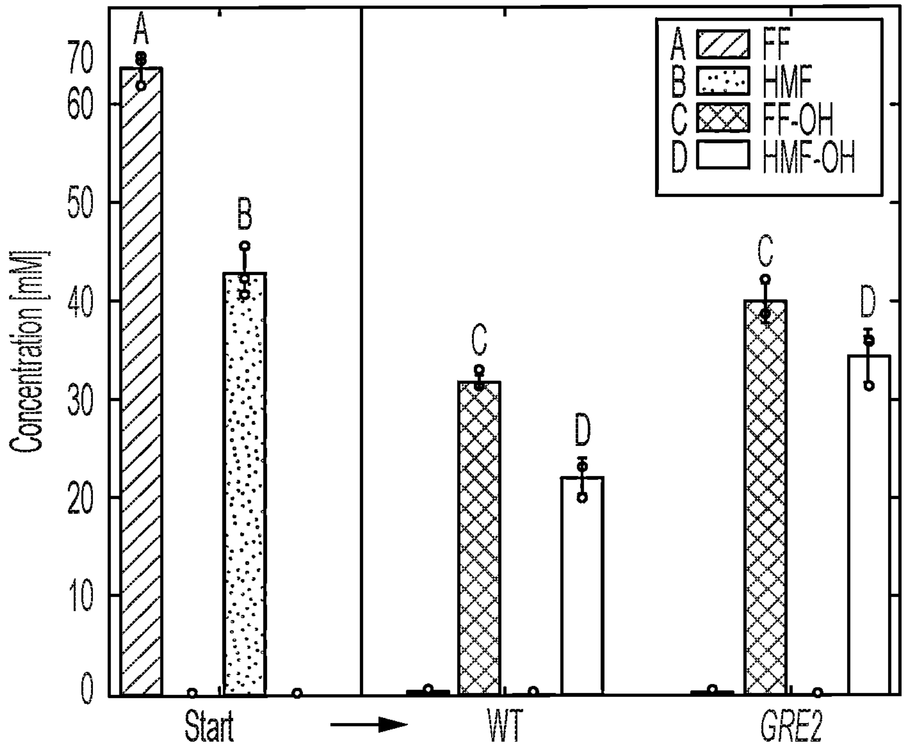

Elevated $K^+$ and pH also conferred improvements to furfural and HMF, but to titers substantially below that of equivalently-elevated YSC. Based on prior work that delineated a mechanism of multi-alcohol tolerance, these improvements, however small, were unlikely to have arisen from tolerance elicited to the 4±0.3 or 34±0.3 g/L of ethanol produced under inhibition (16). Rather, given reports that *S. cerevisiae* naturally possesses various dehydrogenases sufficiently promiscuous to reduce furfural and HMF, it was surmised that these extracellular adjustments were conferring tolerance to their furan alcohol products (27-30). Indeed, 2-furanmethanol (FF—OH) and furan-2,5-dimethanol (HMF-OH) were detected in significant amounts ($p \leq 3.35 \times 10^5$), along with the disappearance of furfural and HMF, after just 24 h of fermentation in an unmodified strain (FIG. 1B, "WT"). When comparing the relative toxicity imposed by these alcohols vs. their aldehyde equivalents, an ethanol output of 35±0.4 g/L demonstrated that FF—OH was 9× more tolerated than furfural at cquimolar concentration (FF—OH vs. FF, light gray); with extracellular K+/pH adjustments (FF—OH, black), production was boosted an additional 69% to 59±0.5 g/L (FIG. 1A). The same trend was recapitulated with HMF where HMF-OH accorded 45% higher titer (HMF-OH vs. HMF, light gray), and media modifications yielded a further 39% that corresponded to production of 69±0.6 g/L (HMF-OH, K+/pH). Unlike acetic acid where $K^+$-only supplementation showed no improvement, the addition of KCl alone to FF—OH and HMF-OH (FF—OH and HMF-OH, medium gray) elicited improvements intermediate to those with K+/pH together. This behavior was consistent with that observed previously for ethanol and underscored the specificity of the membrane permeabilization, and K+/pH countermeasures, to alcohol toxicity (16). Furthermore, across concentrations relevant to genuine hydrolysates, these adjustments consistently elicited an enhancement, one whose efficacy was sustained over a larger range with FF—OH and HMF-OH than with furfural and HMF (FIG. 2B-2C). Given the gains attainable individually on the 3 dominant inhibitors, it was surmised that augmenting in vivo conversion of furfural and HMF to alcohols, paired with the elevation of extracellular K+ and pH, could encapsulate a unified method for bestowing tolerance against the totality of toxicities present in genuine lignocellulosic hydrolysates.

Figure 3:
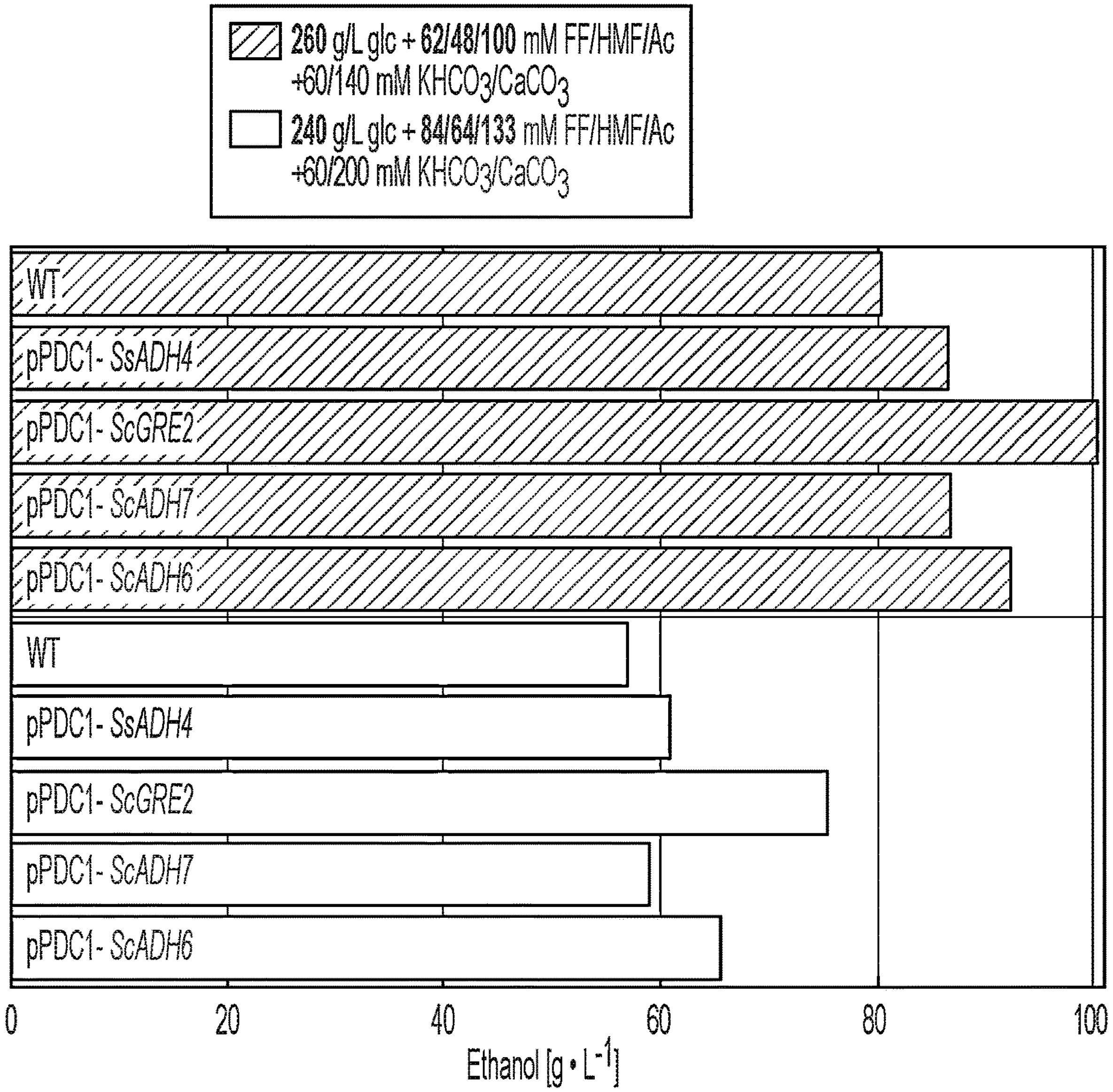
FIG. 3. GRE2 from *S. cerevisiae* confers the highest full tolerance fermentation advantage among the tested panel of reductases with documented activity toward furfural and HMF. Ethanol titers from strains LAMy312, 553, 579, 580, 589 after 46 h of fermentation in YSC-Leu containing glucose (glc), inhibitors, and supplements as indicated in the legend.

Based on literature describing reductases with detoxifying activity toward furfural and HMF, yeast strains over-expressing ADH6, ADH7, or GRE2 from *S. cerevisiae*, or ADH4 from Scheffersomyces *stipitis* were constructed (29-33). Fermentation benchmarking over two repressive conditions combining the trio of inhibitors revealed that *S. cerevisiae* GRE2 evoked the greatest improvement among the candidates. When compared to the wildtype (WT), these improvements amounted to as much as 32% (FIG. 3). Furthermore, that the GRE2 strain sustained a smaller percentage production drop than the WT when moving to the harsher of the two conditions suggested that increased detoxification can enhance robustness over a wider range of toxicity. When FF—OH and HMF-OH were quantified to corroborate the augmented reduction capacity, it was found that GRE2 over-expression produced 25±1% higher concentrations of FF—OH and 56±6% of HMF-OH ($p \leq 3.2 \times 10^3$; FIG. 1B "GRE2"). Despite non-stoichiometric conversion of furfural and HMF, that greater formation of FF—OH and HMF-OH could be engineered indicated that the aggregate toxicity could be mitigated by converting the aldehydes into a form (alcohols) for which means to counteract effectively exist.

Figure 1C:
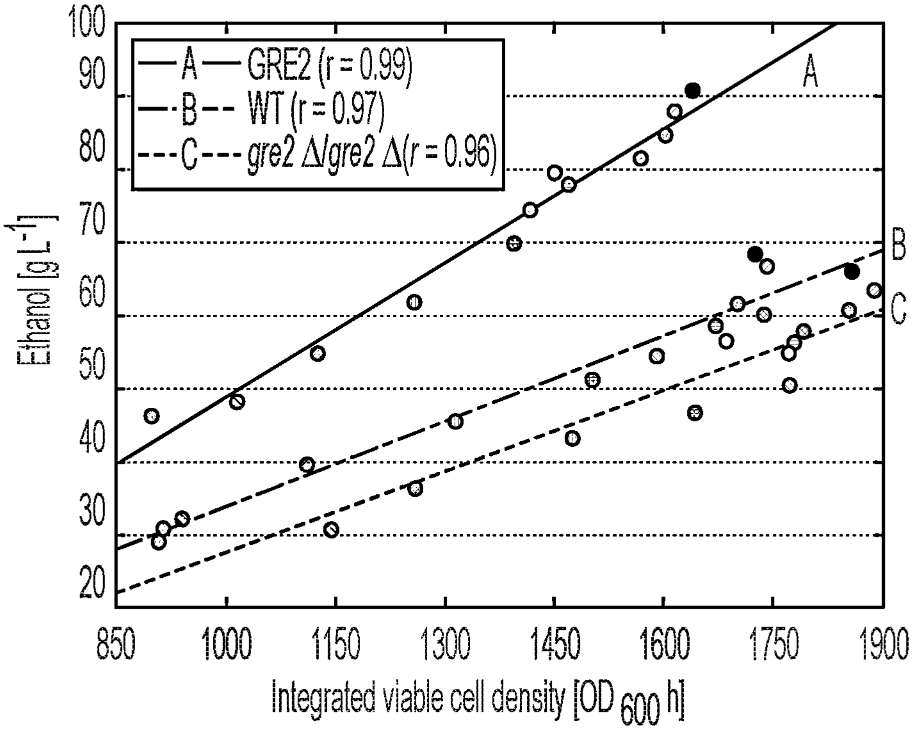
Figure 4:
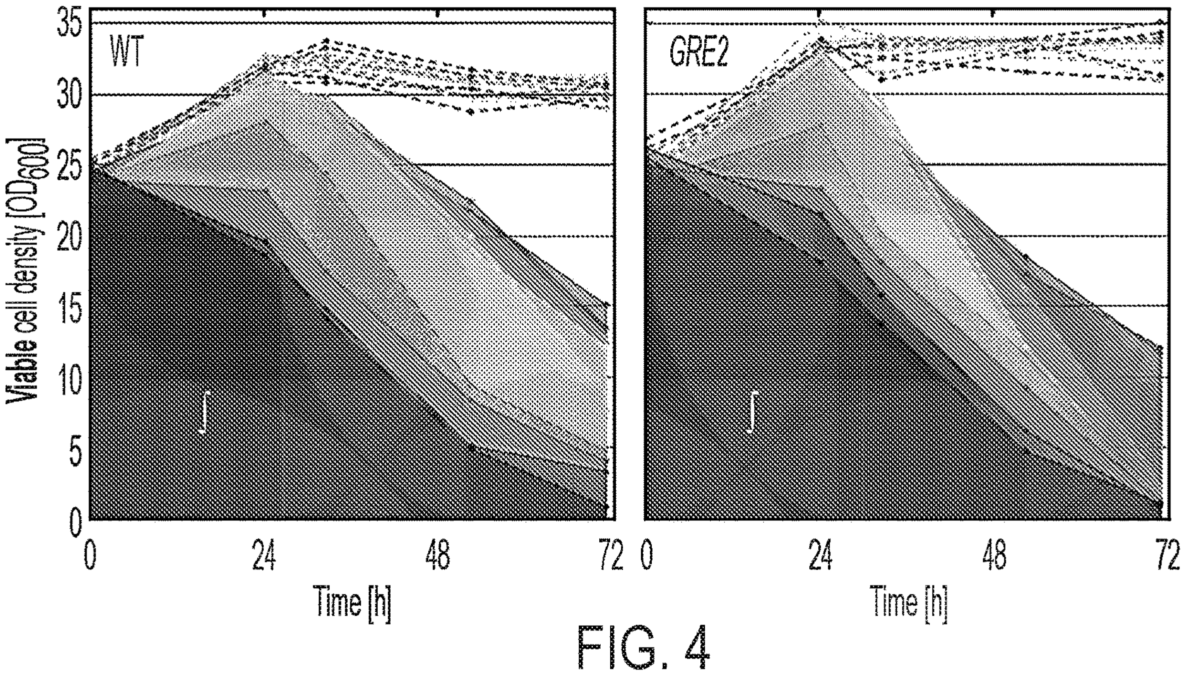
FIG. 4. GRE2 over-expression enables the same total viable cell population to achieve higher ethanol production under toxified conditions. Shades of gray represent conditions of increasing $K^+$ and/or pH supplemented (frontmost=lowest strength; rearmost=highest strength) to strains LAMy312, 579 fermenting YSC-Leu containing 62 mM furfural and 48 mM HMF as described in Materials and Methods, and correspond to the same data points in FIG. 1C. Dotted lines reflect total cell densities measured at 600 nm and corresponding shaded areas the time integrals of cell densities after correcting for the viable fraction (determined by methylene blue staining). Values of these integrals (in $OD_{600}$·h units) are scatter-plotted in FIG. 1C along the x-axis against final ethanol titers along the y-axis.

To characterize productivity under combined furfural and HMF stress, as well as the impact from modulating reductase activity, the relationship between tolerance and ethanol production for the WT, the GRE2 over-expression strain, and one deleted for GRE2 was quantified. Prior work has demonstrated that the viable fraction in an actively fermenting yeast population declined rapidly with accumulating ethanol due to the toxicity of the ethanol itself. However, such mortality could be rescued by $K^+$ and pH adjustments in a dose-dependent manner. Furthermore, time integrations of these viable population fractions ("integrated viable cell density") from progressively higher adjustments, and correlation with ethanol titers, established the relationship between tolerance and production. Importantly, a readout of the time-averaged specific productivity exclusive to the differentially decaying viable fractions was revealed in the correlation slope (16). Therefore, titers and viabilities were measured from a series of fermentations containing furfural, HMF, and incrementally higher adjustments of $K^+$ and/or pH (FIG. 1C, data points left to right). The slope from the GRE2 strain revealed a 59% improvement in per-cell performance over the WT, demonstrating that increased detoxification subdued the combined inhibition effectively to sustain metabolic activity (FIG. 1C). Indeed, for higher extracellular adjustments (e.g., right side data points), the GRE2 strain was quantified to actually have lower viabilities yet greater ethanol production, illustrating that WT cells, while alive, were stalled metabolically (FIG. 4). Furthermore, the higher prevalence of alcohols from GRE2 over-expression (from HMF-OH and FF—OH formation as well as improved ethanol production) likely predisposed the strain to the increasing alcohol protective benefits of incremental $K^+$ and pH, the outcome of which was reflected as higher per-cell performance (i.e., greater slope). Deletion of GRE2 corroborated these trends: while the gre2A/gre24 strain retained the same specific productivity as the WT, the downshift in correlation indicated that any given viability or particular extracellular adjustment would result in lower ethanol output. Thus, GRE2 contributes directly to the resilience of the population by converting furfural and HMF aldehyde stress into alcohols which are subsequently ameliorated by $K^+$ and pH treatment.

Figure 5:
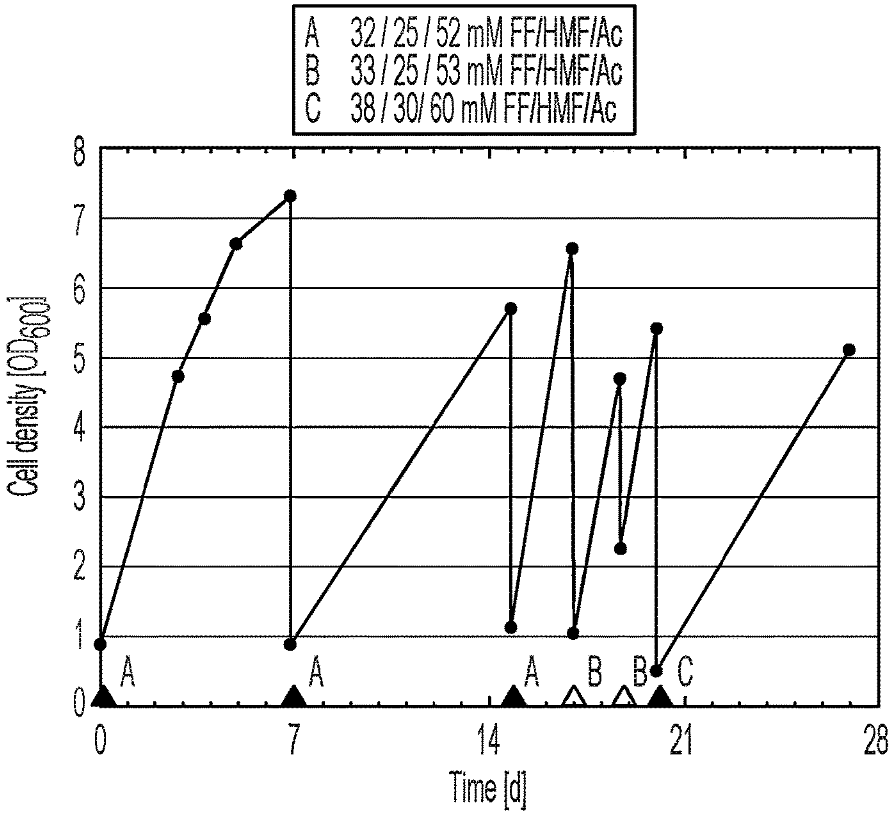
FIG. 5. Time course of PCR-mutagenized GRE2 yeast library under evolutionary selection from incrementally increased combinations of inhibitors. Cell densities ($OD_{600}$) measured from cultures in YSC-Ura containing 30 g/L glucose, inhibitors (as indicated in the legend), supplemental 10 mM $KH_2PO_4$, and adjusted to pH 6. Drops in $OD_{60}$ represent dilution and sub-culturing in fresh medium containing the indicated combination of inhibitors.

Given the efficacy exhibited by the GRE2 over-expression strain, various adaptation approaches were considered to further improve furfural and HMF hydrolysate tolerance. While whole-strain laboratory adaptive evolution is well practiced for augmenting fitness, selective advantages from genome-wide drift have been shown to incur costs in robustness (34, 35). To minimize the risk of pleiotropic deficits undermining feedstock range and strain performance, the detoxification capabilities of GRE2 specifically were honed via directed evolution. Therefore, a yeast library consisting of plasmid-borne PCR-mutagenized GRE2 variants was cultured under combined furfural, HMF, and acetic acid stress, and challenged to increasing toxicity loads over approximately 1 month (36) (FIG. 5). Post-selection isolates were sequence-validated, subcloned into fresh over-expression vectors, and introduced anew into S288C to ensure phenotypes derived exclusively from the plasmid. Individual strains were then screened for a fermentation advantage.

Figure 6A:
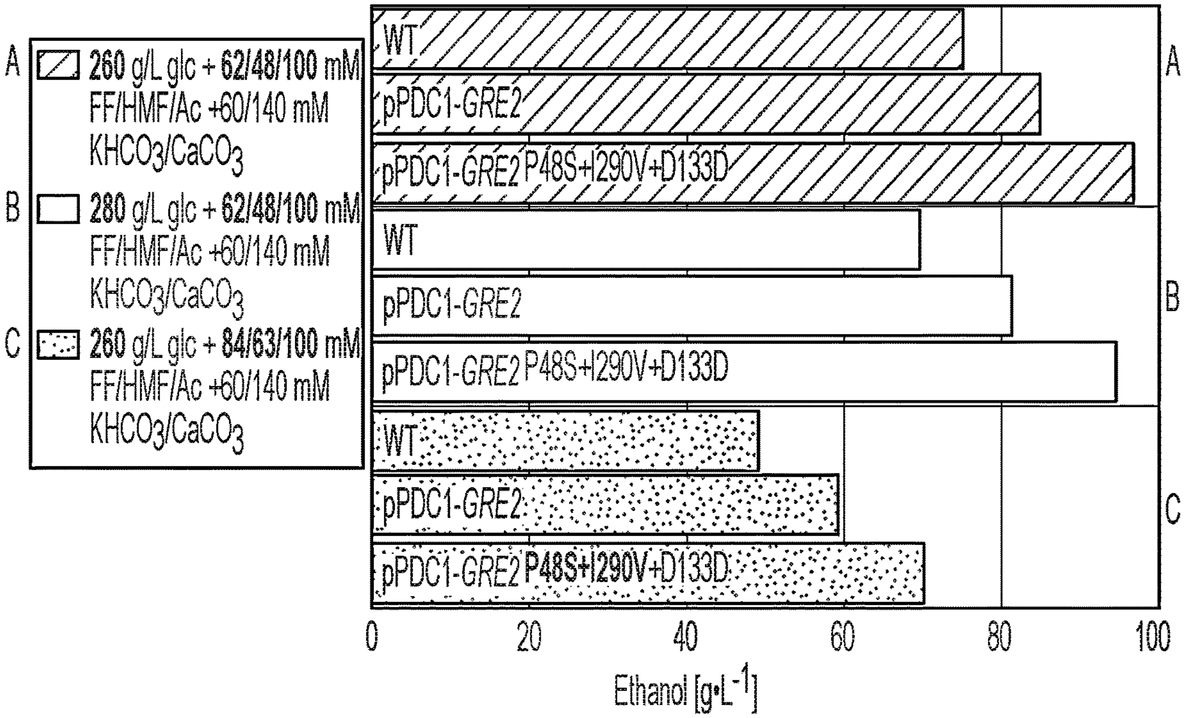
FIGS. 6A-6C. Hyper-tolerant allele $GRE2^{P48S+I290V+D133D}$ ($GRE2^{evol}$) confers a consistent fermentation advantage under full toxicity conditions and imposes minimal expression burden.
Figure 6B:
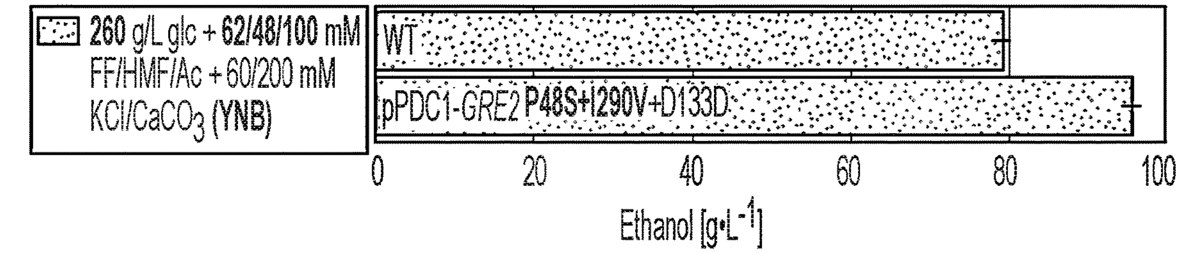
Figure 6C:
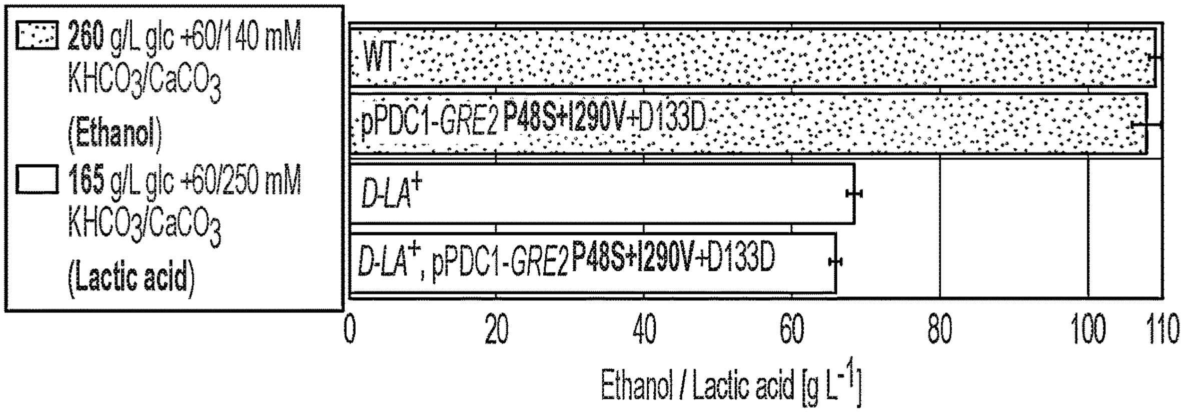

The allele exhibiting the greatest gain was a triple mutant containing a proline to serine substitution at amino acid 48, isoleucine to valine at amino acid 290, and a silent aspartate mutation at amino acid 133 (GRE2P48S+1290V+D133D; hereafter as GRE2$^{evol}$). Across several toxicity combinations mimicking a range of pretreatment severities, GRE2$^{evol}$ consistently conferred improvements over unevolved GRE2 in ethanol production (FIG. 6A). Other than K+ and pH requirements, the superior phenotype was not dependent on extracellular factors supplied by a favorable nutritional environment: in yeast nitrogen base (YNB) minimal medium—containing no amino acids and solely glucose, ammonium sulfate, salts, and trace vitamins—GRE2$^{evol}$ was capable of eliciting a percentage gain comparable to those observed under nutrient-plentiful conditions (FIG. 6B). Furthermore, under nominal/non-toxic conditions where the over-expressed abundance and reductive capacity of GRE2$^{evol}$ could potentially cross-react with, for example, acetaldehyde to boost ethanol yield, statistically unchanged levels of performance were observed (FIG. 6C, top bars). Along with the absence of a major negative impact, these data suggested that the highly-transcribed GRE2$^{evol}$ imposed a low expression burden and functioned largely in an orthogonal manner specific to the hydrolysate inhibitors.

Figure 1D:
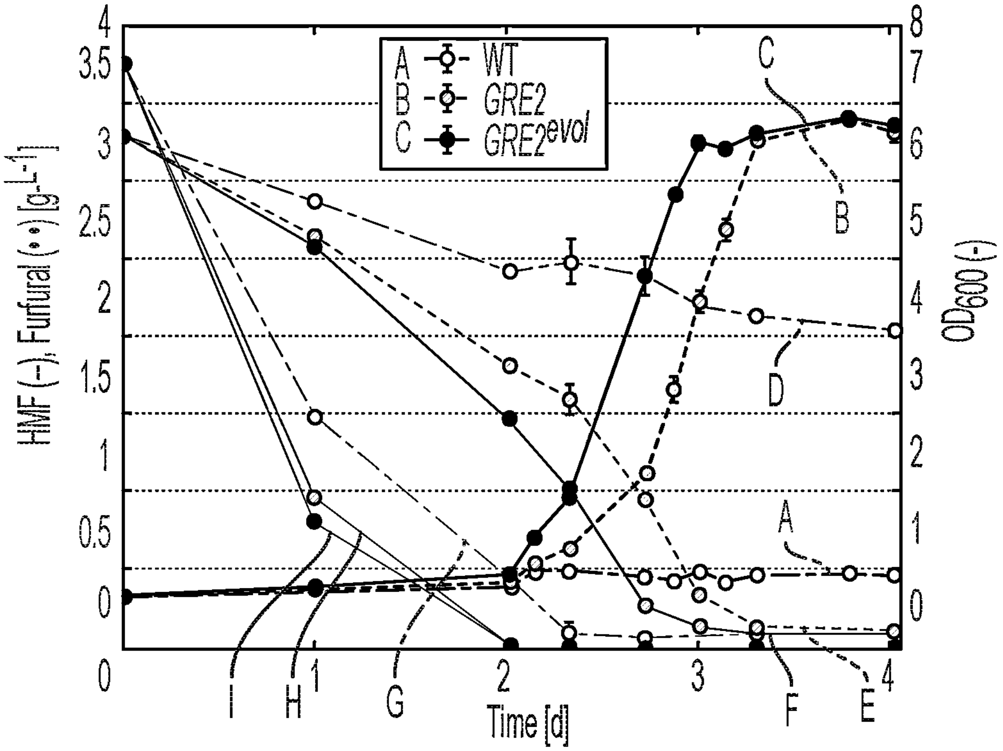

As rates of detoxification are directly proportional to cell biomass (FIG. 1B demonstrated that even the WT could completely reduce furfural and HMF within 24 h at production cell densities), inocula were lowered significantly in a growth assay designed to emphasize fitness advantages enabled by GRE2$^{evol}$ under full toxicity. Here, the WT failed completely to expand, while GRE2$^{evol}$ shortened the lag phase by approximately 7 h compared to unevolved GRE2 (FIG. 1D). The exit from lag was preceded by the detoxification of furfural and HMF where GRE2$^{evol}$ exhibited the highest rates of depletion. Incidentally, when juxtaposed with growth, the decreases in inhibitor concentration revealed further that, unlike furfural, HMF need not be fully detoxified in order for growth to commence and approximately 1.5 g/L are tolerable by yeast.

Expression of GRE2$^{evol}$ was, moreover, capable of conferring near-parity ethanol production between inhibitor-free and fully toxified conditions. To first establish a reference upper bound for inhibitor-free productivity and titer, the WT was fermented in traditional (i.e., non-toxic) high glucose synthetic medium supplemented with potassium bicarbonate ($KHCO_3$) and calcium carbonate ($CaCO_3$)-selected for their widespread industrial and agricultural availability—to provide elevated $K^+$ and pH buffering. Under these optimal conditions, ethanol reached 109±1 g/L in under 32 h (FIG. 7A, Label A). Toxification with 62 mM furfural, 48 mM HMF, and 100 mM acetic acid—a benchmark of above-average toxicity formulated to balance broad feedstock applicability with acceptable yeast performance—output was repressed by 69% to 34±1.2 g/L ethanol. This was despite the adjustment to pH 5 per standard bioethanol practices that also neutralized the acetic acid component (FIG. 7A, Label B) (17, 18, 21, 37). Subsequent supplementation with $KHCO_3$ and $CaCO_3$ was sufficient to rescue stalled productivity in the WT and achieve production of 81±2 g/L (FIG. 7A, Label C). However, substitution with the GRE2$^{evol}$ strain provided a further gain, boosting rate by an additional mean 39% and final product by 31% (FIG. 7A, Label D). The titer of 106±1 g/L ethanol amounted to 97% of that from inhibitor-free medium, demonstrating near-unrestricted ethanol production under full toxicity conditions. Moreover, that the GRE2$^{evol}$ strain remained predominantly repressed under toxification (FIG. 7A, Label E) illustrated the necessity of both the genetic- and extracellular-derived enhancements to attain maximal tolerance.

The targeted detoxification provided by the combination of GRE2$^{evol}$ expression and feedstock $K^+$/pH adjustments was applicable beyond laboratory media to a wide range of genuine lignocellulosic feedstocks. Influenced partly by their history of toxicity and limited utility, the hydrolysates currently available are produced largely at research scale and focused on maximally detoxified cellulosic sugars (6-8, 10, 38, 39). A collection of 7 samples were procured representing a diversity of plant sources (corn stover, sugar cane bagasse, wheat straw, giant *miscanthus*, and switchgrass) and various pretreatment methods, and inhibitors were confirmed to be present in the ranges of 0.1-21 mM furfural, 0.1-6 mM HMF, and 0-178 mM acetic acid (Table 1). These quantities were indeed sufficiently mild such that, aside from the standard supplementation with urea (to provide nitrogen) and adjustment to pH 5, the WT was capable of fermenting all glucose to completion under otherwise unmodified conditions (FIG. 7B, Label A; FIG. 8).

TABLE 1

Hydrolysate samples (concentrations represent first-party or contract vendor measurements).

| Material | Supplier* | Pretreatment | Glc [g/L] | Xyl [g/L] | FF [mM] | HMF [mM] | Ac [mM] | pH | $K^+$ [mM] | $Ca^{2+}$ [mM] |
|---|---|---|---|---|---|---|---|---|---|---|
| Corn stover, DMR (75%) | NREL | Deacetylated, mechanically refined(dilute base, 2 stage milling) | 211 | 111 | 0.3 | 0.2 | 13 | 4.81 | 4 | 7 |
| Corn stover, high acid | NREL | Steam, dilute sulfuricacid (higher concentration) | 120 | 66 | 0.5 | 3.2 | 108 | 4.83 | 28 | 16 |
| Corn stover, low acid | NREL | Steam, dilute sulfuricacid (lower concentration) | 117 | 71 | 0.3 | 2.4 | 92 | 4.78 | 32 | 16 |
| Sugarcane bagasse | Ethtec | High pressure sulfuricacid, chromatography | 113 | 52 | 0.2 | 0.1 | 0 | 2.04 | 14 | 9 |
| Wheat straw *Triticum aestivum L.* | Biochemtex | PROESA ® (chemical-free hot water, steam) | 57 | 32 | 0.1 | 0.1 | 55 | 5.03 | 130 | 6 |

TABLE 1-continued

Hydrolysate samples (concentrations represent first-party or contract vendor measurements).

| Material | Supplier* | Pretreatment | Glc [g/L] | Xyl [g/L] | FF [mM] | HMF [mM] | Ac [mM] | pH | $K^+$ [mM] | $Ca^{2+}$ [mM] |
|---|---|---|---|---|---|---|---|---|---|---|
| *Miscanthus* × *giganteus* | LBNL | Steam, dilute sulfuricacid | 24 | 59 | 20.8 | 6.3 | 178 | 1 | 20 | 9 |
| Switchgrass *P. virgatum* | NCERC | Hot water | 86 | 5 | 3.4 | 0.6 | 18 | 5.23 | 1 | 1 |

*NREL—U.S. Dept. of Energy National Renewable Energy Laboratory,Golden, CO, USA (nrel.gov)
Ethtec—Ethanol Technologies Limited, New South Wales, Australia (ethtec.com.au)
Biochemtex—Eni Versalis S.p.A., Crescentino, Italy (versalis.eni.com)
LBNL—Lawrence Berkeley National Laboratory, Berkeley, CA, USA (lbl.gov)
NCERC—National Corn-to-Ethanol Research Center at Southern Illinois University Edwardsville, Edwardsville, IL, USA (siue.edu/ncerc)

Since inhibitor and glucose loads inherent in the majority of samples fell below that of the formulated benchmark, all samples were toxified to impinge on engineered tolerance limits (Table 2). Furfural was raised to an average 45 mM, HMF to 35 mM, and acetic acid to 100 mM to more closely align with published inhibitory combinations, and glucose to an average 220 g/L for increased osmotic, and ensuing ethanol, stress (17-23). Importantly, supplementation with pure chemical forms of these components was necessary as pre-hydrolyzed solids (and hydrolysis methods) were unavailable to us to boost toxicity using raw cellulosic material. Under these conditions, the WT became repressed even with adjustments to pH 5 (FIG. 7B, Label B). In DMR corn stover, for example, this repression amounted to an output 39% of its minimally modified control. (Glucose supplementation in the remaining feedstocks concomitantly raised ethanol ceilings, rendering comparisons with their minimally modified, lower-glucose controls invalid). The subsequent addition of $K^+$ and pH buffering elicited increases of 1.8-10.7×, enabling 57-91% of the previously residual glucose to be consumed (FIG. 7B, Label C; FIG. 8, Label C). However, when these additions were combined with the GRE2$^{evol}$ strain, over 91% of the final remaining substrate was consumed, increasing production by 10-61% over the WT to titers of 81±1 to 113±0.4 g/L (FIG. 7B, Label D; FIG. 8, Label D). Such performance corresponded to theoretical conversion yields of 78-91% and were all obtained from a single strain derived from a historically underperforming laboratory lineage. However, these titers still exceeded currently published values of cellulosic ethanol produced from un-detoxified industrial feedstocks (40-42). Thus, despite the compositional and pretreatment-by-product complexity across this diversity of material (e.g., *miscanthus* contains ferulic and p-coumaric acids derived from lignin degradation; Table 3), the combination of GRE2$^{evol}$ and alcohol protective $K^+$/pH adjustments exhibited robustness and sufficiency to efficiently ferment highly toxified genuine feedstocks.

TABLE 2

Toxified hydrolysate samples (concentrations represent first-party measurements or additions).

| Material | Supplier | FIG. | Glc [g/L] | Xyl [g/L] | FF [mM] | HMF [mM] | Ac [mM] | $KHCO_3$ [mM] | $CaCO_3$ [mM] | $Ca(OH)_2$ [mM] |
|---|---|---|---|---|---|---|---|---|---|---|
| Corn stover, DMR (75%) | NREL | 7B | 211 | 111 | 36 | 32 | 63 | +40 | +150 | — |
| Corn stover, high acid | NREL | 7B | 225 | 59 | 32 | 26 | 121 | +50 | +100 | +65 |
| Corn stover, low acid | NREL | 7B | 215 | 71 | 32 | 29 | 85 | +50 | +100 | +65 |
| Bagasse | Ethtec | 7B | 198 | 53 | 41 | 33 | 72 | +50 | +150 | — |
| Wheat straw | Biochemtex | 7B | 244 | 29 | 54 | 44 | 103 | — | +150 | +65 |
| *Miscanthus* | LBNL | 7B | 216 | 47 | 54 | 34 | 155 | +60 | — | +270 |
| Switchgrass | NCERC | 7B | 252 | 5.1 | 51 | 43 | 97 | +50 | +100 | +65 |
| Bagasse | Ethtec | 11A | 182 | 52 | 48 | 33 | 72 | +50 | +150 | — |
| Corn stover, high acid | NREL | 11A | 156 | 57 | 45 | 32 | 108 | +50 | +100 | +65 |
| *Miscanthus* | LBNL | 11A | 157 | 46 | 57 | 36 | 165 | +60 | — | +255 |
| Corn stover, DMR (65%) | NREL | 11B | 167 | 85 | 59 | 34 | 67 | +50 | +250 | — |
| Corn stover, low acid | NREL | 11B | 159 | 62 | 54 | 35 | 90 | +30 | +260 | — |
| Wheat straw | Biochemtex | 11B | 167 | 27 | 63 | 42 | 72 | — | +280 | — |

TABLE 3

Gas chromatography-mass spectrometry analysis of *Miscanthus* × *giganteus* hydrolysate; courtesy of Stefan Bauer (LBNL).

| Target compound | [μg/ml] |
|---|---|
| ISTD (internal standard) | 19.57 |
| Guaiacol | 1.91 |
| Benzoic acid | 0.46 |
| Catechol | 0.78 |
| Resorcinol | — |
| 4-Hydroxybenzaldehyde | 22.48 |
| 4-Methylcatechol | — |
| 3-Methylcatechol | — |
| Hydroquinone | 8.90 |
| Eugenol | 0.47 |

TABLE 3-continued

Gas chromatography-mass spectrometry analysis of *Miscanthus* × *giganteus* hydrolysate; courtesy of Stefan Bauer (LBNL).

| Target compound | [μg/ml] |
|---|---|
| 2-Hydroxybenzoic acid | 0.36 |
| Vanillin | 41.25 |
| 3-Hydroxybenzoic acid | 0.81 |
| Iso-eugenol | — |
| 3,4-Dihydroxybenzaldehyde | 2.13 |
| Acetovanillone | 3.56 |
| 4-Hydroxybenzoic acid | 7.09 |
| Vanillyl alcohol | — |
| 4-Hydroxyphenylacetic acid | 1.76 |
| Syringaldehyde | 26.80 |
| Homovanillyl alcohol | 1.01 |
| 3-(4-OH-phenyl)propionic acid | 2.09 |
| Vanillic acid | 26.94 |
| Homovanillic | 3.41 |
| Acetosyringone | 1.58 |
| 2,5-Dihydroxybenzoic acid | 1.87 |
| 4-Hydroxymandelic acid | 4.53 |
| 3,4-Dihydroxybenzoic acid | 4.10 |
| 3,4-Dihydroxyphenylacetic acid | 0.86 |
| 4-Hydroxycoumarin | — |
| 4-OH-3-OCH3-cinnamaldehyde | 15.65 |
| 4-OH-3-OCH3-mandelic acid | 2.55 |
| Syringic acid | 16.60 |
| p-Coumaric acid | 141.33 |
| Coniferyl alcohol | 1.61 |
| Gallic acid | 1.08 |
| Sinapaldehyde | 7.58 |
| Iso-ferulic acid | — |
| Ferulic acid | 141.88 |
| Caffeic acid | 4.15 |
| Sinapic acid | 1.90 |

Since genuine hydrolysates are highly undefined mixtures with unknown levels of salts, uninformed additions of $K^+$ and particular buffer counter-cations could potentially exceed osmotic shock thresholds in yeast (43-45). As it had been previously established that $K^+$ has fermentation-beneficial effects to at least 110 mM and $Ca^{2+}$ is fermentation-neutral, it was deemed important to maintain total $K^+$ within this limit and modulate pH via $Ca^{2+}$-based buffers or bases (16). Thus, cation concentrations in each sample were determined by mass spectrometry and used to determine the specific mixes of $KHCO_3$, $CaCO_3$, and calcium hydroxide to provide as supplementation (Table 1 and Table 2). The atypically high $K^+$ concentration in wheat straw, in fact, provided an opportunity to validate these constraints: when 50 mM $KHCO_3$ and 100 mM $CaCO_3$ were used in lieu of 150 mM $CaCO_3$, the oversupply of $K^+$ resulted in decreases to performance despite the same pH buffering capacity (FIG. 9). Therefore, supplementation customized to each feedstock conforming to salt-specific limits is necessary to achieve maximal efficacy.

These tolerance capabilities were fully transferrable to the fermentation of inhibitor-laden xylose, the pentose comprising a significant portion of lignocellulosic sugars that unmodified *S. cerevisiae* cannot consume (6, 17). The inventors of the present disclosure had previously engineered a strain ($XYL^+$) that efficiently fermented xylose to ethanol, but preferentially utilized glucose if present (46). Therefore, a YSC-based hydrolysate was formulated to favor xylose metabolism, yet mimic genuine cellulosic proportions, by combining xylose with starch whose glucan polymers were slowly digested to glucose via incrementally-dosed amylases. In the absence of inhibitors, the $XYL^+$ chassis completely consumed available xylose and glucose in this medium and produced 62±0.9 g/L of ethanol (FIG. 11A, bold Label A; FIG. 10, bold Label A). Toxification with the benchmark suite of furfural, HMF, and acetic acid repressed production to 8±1 g/L, and subsequent treatment with elevated $K^+$ and pH buffering provided recovery to 22±0.9 g/L with improved proportional usage of sugar (FIG. 11A, bold Label B and Label C; FIG. 10). However, when $GRE2^{evol}$ was introduced into $XYL^+$ with no further modifications, the chassis was functionalized to ferment all xylose and glucose, restoring production essentially 100% to 66±0.6 g/L (FIG. 11A, bold Label D; FIG. 10, bold Label D). The combination of genetic and extracellular tolerance enhancements thus enabled the prior-engineered metabolism to achieve full production capacity under complete toxicity conditions.

Moreover, the $GRE2^{evol}$-enhanced $XYL^+$ strain maintained its tolerance capabilities on multiple toxified genuine hydrolysates. Due to catabolite repression, xylose went unconsumed by the $XYL^+$ chassis strain in minimally modified hydrolysates of sugarcane bagasse and high acid corn stover (FIG. 11A, non-bold Label A; FIG. 10, non-bold Label A). *Miscanthus* proved, fortuitously, to be an exception: as glucose was present in amounts lower than xylose and depleted rapidly, xylose metabolism remained sufficiently active such that both monomeric sugars were near-entirely consumed. Toxification from increased glucose, furfural, HMF, and acetic acid repressed production in all 3 hydrolysates to below 15 g/L ethanol. While these inhibitory conditions were relieved by elevated $K^+$ and pH buffering, the recoveries exhibited much greater variability than in S288C (FIG. 11A, non-bold Label B and Label C; Table 2). In high acid corn stover, for example, an improvement was statistically questionable ($p=0.76$) while that for *miscanthus* was a significant 689±1% ($p=1.00\times10^{-6}$). However, these inconsistent recoveries were subsequently remedied in a robust manner by the introduction of $GRE2^{evol}$ where gains averaged a further 260% (FIG. 11A, non-bold Label D). In *miscanthus*, this, additionally, enabled partial fermentation of xylose despite higher catabolite repression from supplemented glucose (FIG. 10). Again, the combination genetic and extracellular tolerance enhancements proved effective across disparate, toxified, genuine feedstocks.

The recapitulation of phenotype and substrate robustness on a pre-existing metabolic chassis suggested that $GRE2^{evol}$ expression and $K^+$/pH feedstock adjustment could constitute a functionally orthogonal tolerance platform integrable with other engineered end products. Given that the alcohol-focused countermeasures may have conferred a bias toward ethanol production, an effort was made to endow hydrolysate tolerance on a non-alcohol product, namely, a glucose-consuming strain synthesizing the biodegradable plastics precursor lactic acid (D-LA), a chemical commodity projected to reach US$9 billion by 2025 (47). Given the evolutionary predilection of *S. cerevisiae* for alcoholic fermentation, elimination of ethanol has been a major goal in all efforts to reengineer yeast for non-ethanol products. Here, the inventors of the present disclosure opted to minimize, rather than eliminate, glycolytic flux toward ethanol in order to maintain subsistence ATP generation for cell growth and active lactate export (48). As lactate and ethanol share a common precursor in pyruvate, pyruvate decarboxylase activity and losses to ethanol were curtailed by creating a pdc1Δ/pdc1Δ pdc5Δ/pdc5Δ::pTEF1m4-PDC5 strain where a sole chromosomal pyruvate decarboxylase gene was transcribed using a handicapped variant of the TEF1 promoter (49-51). Reductive conversion of pyruvate to lactate was fulfilled via expression of D-lactate dehydrogenase from *L. mesenteroides* (52).

In synthetic medium supplemented with $KHCO_3$ and sufficient $CaCO_3$ to buffer lactic acid accumulation, and likewise in DMR corn stover minimally supplemented with $CaCO_3$, the D-$LA^+$ chassis generated inhibitor-free reference titers of 66±0.3 and 65±0.4 g/L, respectively (FIG. 11B, Label A). Under complete toxification, elevated $K^+$ and pH buffering, combined with $GRE2^{evol}$ expression and no additional modifications, succeeded in conferring tolerance such that cellulosic lactic acid reached 90% and 96% of these clean sugar benchmarks (FIG. 11B, Label D). Like $XYL^+$, the engineered D-$LA^+$ metabolism was largely liberated from inhibition to elicit near-unrestricted production. Furthermore, strain robustness to additional hydrolysates was investigated using low acid corn stover and wheat straw. As before, these feedstocks (unlike DMR corn stover) contained the stress from supplemented glucose as well as toxification from the trio of inhibitors. Nevertheless, $GRE2^{evol}$ expression was capable of eliciting mean gains of 19% over the unengineered chassis to attain cellulosic product titers greater than 50 g/L. Although higher lactic acid production from yeast has been reported, all prior studies were conducted using traditional, clean sugar feedstocks; titers here, furthermore, were restrained by the chassis' inherently limited synthesis capabilities (52-54). Importantly, the single-transformation tolerance phenotype minimally interfered with the engineered lactic acid metabolism (FIG. 6C); likewise, $GRE2^{evol}$ remained predominantly orthogonal and unperturbed to alleviate toxicity efficiently. The findings in the present disclosure represent the first demonstration of a non-ethanol cellulosic product delivered with industrially-relevant performance from multiple highly toxified genuine feedstocks using a single strain.

Example 2: Materials and Methods for Example 1

Plasmid Construction

All plasmids were assembled using the Gibson method from segments generated via PCR. Amplification of plasmid backbone, yeast promoter, protein coding, and transcription termination fragments (see below) was carried out using the Phusion High-Fidelity DNA polymerase (New England Biolabs #M0530, neb.com) in 50 μL reactions following the manufacturer's directions. Primers were designed with 25-30 bp 5' overhangs to serve as assembly junctions and annealing temperatures of primer pairs optimized using the vendor-provided calculator (tmcalculator.neb.com). The suggested extension times of 30 s/kb were often inadequate empirically and extended to 60 s/kb for problematic amplicons (fragments >2-3 kb tended to require the higher extension rate). For templates containing a bacterial origin of replication (e.g., plasmid backbone segment), PCR products were further digested with 20 U of DpnI (New England Biolabs #R0176) added directly to the reaction sample post-thermocycling (i.e., no additional restriction enzyme buffer), incubated for 90 min at 37° C., and heat inactivated for 20 min at 80° C. All fragments were purified and concentrated (up to 3 pooled PCR reactions per column) using the QIAquick PCR Purification Kit (QIAGEN #28106, qiagen.com) and DNA concentrations quantified with a NanoDrop Microvolume UV-Vis spectrophotometer. Gibson reactions were prepared from these eluates using 50-100 ng of vector and molar ratios of 1 part vector to 4-8 parts of each insert in the lowest volume possible (i.e., no additional $H_2O$ to meet the instructed minimum of 10 μL). Assembly enzymes were supplied through a cocktail (New England Biolabs #E2611) and reactions incubated for 30 min at 50° C. followed by an additional 1 h to overnight at room temperature. Chemically competent *E. coli* (New England Biolabs #C2992) were transformed and cultured per manufacturer instructions, and ampicillin-resistant isolates screened by PCR using vector- and insert-specific primers. Plasmids derived from positively scoring transformants were extracted using the QIAprep Spin Miniprep Kit (QIAGEN #27106) and validated by Sanger sequencing (QuintaraBio, quintarabio.com).

Minimal backbone segments-containing solely the bacterial replication origin, ampicillin marker, yeast replication origin, and yeast selection marker-were sourced from the p415 and p426 expression series developed by Mumberg et al. (56). For strong transcription in yeast coupled to glycolytic activity, either the TDH3 ("GPD") or TEF1 promoters were retained from the Mumberg vectors or the −703 to −1 fragment of the PDC1 promoter was cloned from FY4/5 genomic DNA. Protein coding sequences for ADH6, ADH7, and GRE2 were likewise amplified directly from FY4/5 genomic DNA. For ADH4 from S. *stipitis*, Bio Basic (biobasic.com) was contracted to synthesize a *S. cerevisiae* codon-optimized sequence from the publicly available protein translation (GenBank accession no. XM_001387085). Similarly, IdhA from *L. mesenteroides* subsp. *mesenteroides* was produced by Eurofins Genomics (eurofinsgenomics.com) from the amino acid sequence available from UniProt (gene entry LEUM_1756). For transcription termination, either the CYC1 element from Mumberg or from FY4/5 genomic DNA were retained and the 166 bp immediately following the stop codon of ADH1 or the 295 bp following ACTI was cloned.

To clone the GRE2 mutants emerging from toxicity selection, the plasmid-based coding sequences were distinguished from chromosomal GRE2 via an initial PCR using primers binding to library plasmid elements. Specifically, the collection of mutagenized genes, including their non-mutagenized promoters and terminators, were originally subcloned via Gateway recombination and positioned between attB1 and attB2 sequences (36). Thus, from total DNA isolated from the final inhibitor-tolerant culture (FIG. 5), an initial amplification was performed using primers annealing to these unique attB elements. To further subclone the coding sequences of hyper-tolerant GRE2 mutants, the plasmid-derived amplicons were used to template a second-pass PCR excluding the GRE2 promoter and terminator. These amplified protein coding fragments were subsequently Gibson-assembled into final expression constructs. Table 4 shows a complete list of over-expression plasmids used in the present disclosure.

TABLE 4

Over-expression vectors.

| Plasmid | Gene Insert | Reference |
|---|---|---|
| pRS415 | — | (24) |
| p415-pPDC1-ADH6-tACT1 | *S. cerevisiae* ADH6 (YMR318C) | This study |
| p415-pPDC1-ADH7-tCYC1 | *S. cerevisiae* ADH7 (YCR105W) | This study |
| p415-pPDC1-GRE2-tCYC1 | *S. cerevisiae* GRE2 (YOL151W) | This study |
| p415-pPDC1-SsADH4-tCYC1 | *S. stipitis* ADH4 (GenBank XM_001387085), codon optimized for *S. cerevisiae* | This study |

TABLE 4-continued

Over-expression vectors.

| Plasmid | Gene Insert | Reference |
|---|---|---|
| p415-pPDC1-GRE2(P48S + I290V + D133D)-tCYC1 | *S. cerevisiae* GRE2$^{P48S+I290V+D133D}$, from directed evolution | This study |
| p415-pGPD-GRE2(P48S + I290V + D133D)-tCYC1 | *S. cerevisiae* GRE2$^{P48S+I290V+D133D}$, from directed evolution | This study |
| p426TEF1-LmLDHA-tADH1 | *Leuconostoc mesenteroides* subsp. *mesenteroides* (ATCC 8293) ldhA (UniProt LEUM_1756), codon optimized for *S. cerevisiae* | This study |

Yeast Strain Construction.

Recombinant strains were created following the lithium acetate chemical transformation method of Gietz et al. (57). For single plasmid introduction, 50 ng of p(RS)415-based DNA was used with 1 $OD_{600}$ unit of cells and selection carried out on solid YSC-Leu dropout medium. For strains generated from introduction of two simultaneous plasmids, 150-300 ng each of p426TEF- and p(RS)415-based DNA was used with 3-4 $OD_{600}$ units, and selection done on YSC-Ura-Leu solid medium. For chromosomal integrations, 800 ng-1 μg of linear DNA was used with 7-10 $OD_{600}$ units. Low transformation efficiencies (e.g., from variability in strain, locus, DNA secondary structure) were typically resolved by increasing the DNA to cell ratio, amount of salmon sperm carrier DNA, or heat shock incubation time (up to 40-50 min at 42° C.).

In addition to laboratory standard BY4743, the gre24::kanMX4/gre2A::kanMX4 diploid used for LAMy629 pre-existed this study and was obtained from the *Saccharomyces* Genome Deletion Project collection (sequence.stanford.edu/group/yeast_deletion_project/).

To create the diploid xylose-consuming chassis (XYL+), a xylose-enabled MATa leu2-3 haploid (internal strain F258) available from the development efforts of Zhou et al., 2012 was transformed with plasmid pJH727 (GAL::HO LEU2; gift from Jim Haber of Brandeis University) to generate a MATa equivalent (46, 58). Induction of the HO gene in Leu+ transformants was conducted in liquid medium containing 20 g/L galactose for 6 h at 30° C. (complete mating type switching protocol, including pre-induction, is available from the Haber Lab website: bio.brandeis.edu/haberlab/jehsite/protocol.html). Individual colonies, recovered from growth in glucose medium additionally containing leucine to discard pJH727, were screened for MATα haploids by α- and a-factor sensitive mating type tester strains (59). A validated MATa leu2-3 haploid was subsequently mated with F258 to create the homozygous XYL$^{+}$ leu-chassis strain LAMy435 that preceded LAMy419 and 665.

To create the S288C leu-predecessor of LAMy660, 661, and 663, the defective his3Δ1/and ura3Δ0 alleles in BY4743 were corrected sequentially by targeted chromosomal replacements. In brief, a PCR product encompassing the full length coding sequence of HIS3 was amplified from FY4/5 genomic DNA, introduced into BY4743, and transformants selected for histidine prototrophy. To repair ura3Δ0, which spans a segment larger than the open reading frame of URA3, a PCR product including 320 bp of the URA3 promoter and 194 bp beyond the stop codon was amplified from FY4/5 genomic DNA, introduced into the His+ intermediate, and transformants selected on minimal yeast nitrogen base (YNB) medium supplemented solely with leucine to yield chassis strain LAMy651.

To create the diploid ethanol-handicapped chassis for lactic acid production, a fully ethanol-deficient pdc-haploid was first generated by creating a markerless deletion of PDC5 in a MATa pdc1Δ::kanMX4 strain sourced from the *Saccharomyces* Genome Deletion Project collection (PDC6, while intact, is functionally inert). Briefly, plasmid PCR-SPR,PDC1±5 expressing a *Candida albicans/S. cerevisiae* codon-optimized version of Cas9, and a guide RNA targeting the PAM-proximal sequence TGCTAAGAACCCAGTTATCT (SEQ ID NO: 3) common to PDC1 and PDC5, was co-electroporated with the double-stranded linear repair template:

```
                                        (SEQ ID NO: 4)
CATAATCAATCTCAAAGAGAACAACACAATACAATAACAAGAAGAACAAA

GCTAATTAAC
```

into the MATa pdc1Δ::kanMX4 haploid according to the protocol of Vyas et al. (plasmid and template are gifts of Boon Uranukul) (60). Transformants were selected on solid YP (yeast bacto-peptone) medium containing 3% ethanol, 3% glycerol, and 100 μg/mL nourscothricin (YPEG+NAT), and isolates comparatively grown on YPEG+NAT and YPD (YP with 2% glucose) solid media to identify the pdc-phenotype (development strain LAMy399).

Separately, a haploid containing PDC5 transcribed by the low strength TEF1m4 promoter mutant was generated in a MATα pdc1Δ::kanMX4 strain sourced from the *Saccharomyces* Genome Deletion Project collection. Here, the in-locus markerless edit was likewise accomplished through a similar CRISPR protocol with plasmid LAMb66 (featuring uracil selection in yeast and improved Cas9 expression) encoding a guide RNA targeting sequence TTCTCGATCAATATACTGTA (SEQ ID NO: 5) in the PDC5 promoter and the double-stranded repair template:

```
                                        (SEQ ID NO: 6)
CAAAGGTCGCGTTTCTTTTAGAAAAACTAATACGTAAACCTGCATTAAGG

GAACAAAAGCTGGAGCTCATAGCTTCAAAAcGcTTCTACcCCcTTTTTAC

TCTTCCAGATTTTCTCGGACTCCGCGCATCGCCGTACCACTTCAAgACAC

CCAAGCACAGCATACTAAATTTCCCCTCTTTCTTCCTCTAGGGTGTCGcT

AATTACCCGTACTAAAGGTTTGGAAAAGAAAAAAGgGACCGCCTCGTTTC

TTTcTCTTCGTCGAgAgAGGCAATAAAAATTTTTATCACGTTTCTTTTTC

TTGAgAgTTTcTTTcTtGATTTTTTTCTCTTTCGATGACCTCCCATTGAT

ATTTAAGcTAATAAACGGTCTTCAATTTCTCAAGcTTCAGTTTCATTTTT

CTTGTTCTATTACAACTTTTTTTACTTCTTGCTCgTTAGAgAGAAAGCAT

AGCAATCTAATCTAAGTTTTCTAGAAAAATGTCTGAAATAACCTTAGGTA

AATATTTATTTGAAAGATTGAGCCAAGT
```

where lowercase letters designate the TEF1m4 promoter mutations (50). Transformants were selected on YSC-Ura solid medium and small colonies suggesting handicapped glucose growth validated further by PCR using primer pairs identifying the TEF1m4 promoted-PDC5 fusion. This haploid was mated to LAMy399 to produce the PDC5 heterozygote, and the diploid subsequently made His+ via the chromosomal integration described above to yield the ethanol-handicapped chassis strain LAMy670 preceding LAMy690 and 692.

All final strains were re-validated by PCR using plasmid- or modification-specific primers and the relevant regions Sanger sequenced as appropriate before fermentation experiments. Table 5 shows a complete list of strains used in this study.

TABLE 5

Yeast strains (bold indicates plasmids introduced in this study).

| Strain | Genotype | Reference |
| --- | --- | --- |
| BY4743 | S288C MATa/α his3Δ1/his3Δ1 leu2Δ0/leu2Δ0 LYS2/lys2Δ0 met15Δ0/MET15 ura3Δ0/ura3Δ0 | (24) |
| FY4/5 | S288C MATa/α (prototrophic) | (24) |
| LAMy312 | BY4743 + **pRS415** | This study |
| LAMy419 | BF264-15Dau MATa/α TRP1::pTDH3-RKI1-tCYC1-pTDH3-RPE1-tCYC1/TRP1::pTDH3-RKI1-tCYC1-pTDH3-RPE1-tCYC1 HIS2::pTDH3-TKL1-tCYC1/HIS2::pTDH3-TKL1-tCYC1 ADE1::pTDH3-PsTAL1-tCYC1/ADE1::pTDH3-PsTAL1-tCYC1 + pRS426-XYLA-XYL3$^{evol}$ + pUCAR1 + **pRS415** | This study |
| LAMy553 | BY4743 + **p415-pPDC1-SsADH4-tCYC1** | This study |
| LAMy579 | BY4743 + **p415-pPDC1-GRE2-tCYC1** | This study |
| LAMy580 | BY4743 + **p415-pPDC1-ADH7-tCYC1** | This study |
| LAMy589 | BY4743 + **p415-pPDC1-ADH6-tACT1** | This study |
| LAMy629 | BY4743 gre2Δ::kanMX4/gre2Δ::kanMX4 + **pRS415** | This study |
| LAMy660 | S288C MATa/α his3Δ1/HIS3 leu2Δ0/leu2Δ0 LYS2/lys2Δ0 met15Δ0/MET15 ura3Δ0/URA3 + **pRS415** | This study |
| LAMy661 | S288C MATa/α his3Δ1/HIS3 leu2Δ0/leu2Δ0 LYS2/lys2Δ0 met15Δ0/MET15 ura3Δ0/URA3 + **p415-pPDC1-GRE2-tCYC1** | This study |
| LAMy663 | S288C MATa/α his3Δ1/HIS3 leu2Δ0/leu2Δ0 LYS2/lys2Δ0 met15Δ0/MET15 ura3Δ0/URA3 + **p415-pPDC1-GRE2(P48S + I290V + D133D)-tCYC1** | This study |
| LAMy665 | BF264-15Dau MATa/α TRP1::pTDH3-RKI1-tCYC1-pTDH3-RPE1-tCYC1/TRP1::pTDH3-RKI1-tCYC1-pTDH3-RPE1-tCYC1 HIS2::pTDH3-TKL1-tCYC1/HIS2::pTDH3-TKL1-tCYC1 ADE1::pTDH3-PsTAL1-tCYC1/ADE1::pTDH3-PsTAL1-tCYC1 + pRS426-XYLA-XYL3$^{evol}$ + pUCAR1 + **p415-pGPD-GRE2(P48S + I290V + D133D)-tCYC1** | This study |
| LAMy690 | S288C MATa/α his3Δ1/HIS3 leu2Δ0/leu2Δ0 LYS2/lys2Δ0 met15Δ0/ura3Δ0 pdc1Δ::kanMX4/pdc1Δ::kanMX4 pdc5Δ/pdc5Δ::pTEF1m4-PDC5 + **p426TEF-LmLDHA-tADH1** + **pRS415** | This study |
| LAMy692 | S288C MATa/α his3Δ1/HIS3 leu2Δ0/leu2Δ0 LYS2/lys2Δ0 met15Δ0/MET15 ura3Δ0/ura3Δ0 pdc1Δ::kanMX4/pdc1Δ::kanMX4 pdc5Δ/pdc5Δ::pTEF1m4-PDC5 + **p426TEF-LmLDHA-tADH1** + **p415-pGPD-GRE2(P48S + I290V + D133D)-tCYC1** | This study |

Media and Fermentation Conditions

To provide a consistent but modifiable medium to accommodate the entire collection of strains, all baseline culturing was performed in yeast synthetic complete medium (YSC) composed of 1.5 g/L Yeast Nitrogen Base without Amino Acids & Ammonium Sulfate (BD-Difco #233520, bd.com), 5 g/L ammonium sulfate, 0.2 mM inositol, 0.1 g/L of each of the 20 amino acids, and 0.1 g/L each of adenine and uracil (all from Sigma-Aldrich, sigmaaldrich.com). Strains containing a p(RS)415 plasmid were maintained in medium lacking leucine and those with a p426 plasmid lacking uracil. Unless indicated otherwise, individual strains were expanded and acclimated to high cell density and high sugar conditions in singlicate YSC-based cultures and divided into triplicate biological samples upon inoculation into fermentation (FIGS. 1A-1C; FIGS. 7A-7B; FIGS. 11A-11B) or growth (FIG. 1D) media. All yeast culturing and fermentations were conducted at 30° C. in Erlenmeyer flasks (≥25 mL) shaken at 200 RPM or glass tubes (≤12 mL) rotated in a cell culture roller drum at maximum speed.

For the constituent toxicity studies, prototrophic strain FY4/5 was expanded in a starter culture of YSC containing 150 g/L glucose and grown overnight to approximately $OD_{600}$=10. To mimic industrial high cell density conditions, 100 $OD_{600}$ units of cells per fermentation were harvested, washed with an equal volume of room temperature distilled and deionized water, and cell pellets resuspended in 4 mL media for a production cell density of approximately $OD_{600}$=25 (9.9 g DCW/L). Fermentation media consisted of 250 g/L glucose in YSC and were supplemented with (left to right in FIG. 1A) 6 mM $NH_4Cl$, 50/6 mM KCl/$NH_4OH$, 100/128 mM acetic acid/$NH_4Cl$, 100/50/128 mM acetic acid/KCl/$NH_4Cl$, 100/50/128 mM acetic acid/KCl/$NH_4OH$, 100/11 mM furfural/NHCl, 100/50/11 mM furfural/KCl/$NH_4OH$, 100/7 mM 2-furanmethanol (FF—OH)/NHCl, 100/50/7 mM FF—OH/KCl/$NH_4Cl$, 100/50/7 mM FF—OH/KCl/NHOH, 100/7 mM 5-hydroxymethyl-furfural (HMF)/$NH_4Cl$, 100/50/7 mM HMF/KCl/NHOH, 100/7 mM furan-2,5-dimethanol (HMF-OH)/$NH_4Cl$, 100/50/7 mM HMF-OH/KCl/$NH_4Cl$, or 100/50/7 mM HMF-OH/KCl/$NH_4OH$.

Figure 2A:
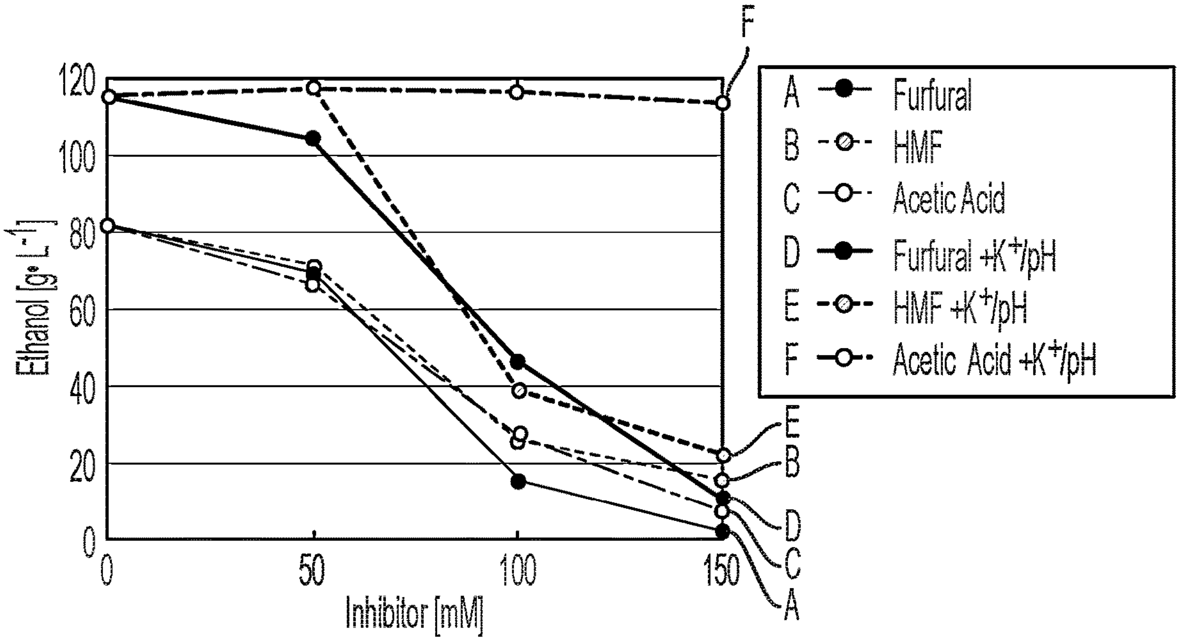
FIGS. 2A-2C. Elevated $K^+$ and pH enhance ethanol production inhibited by the dominant universal toxicity components in cellulosic hydrolysates.
Figure 2B:
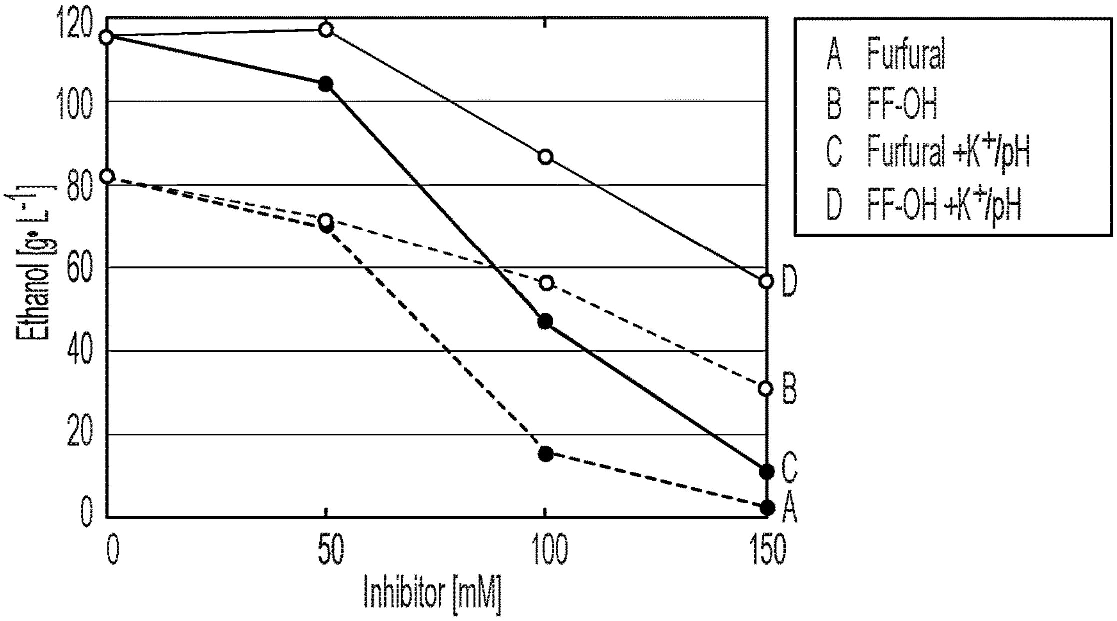
Figure 2C:
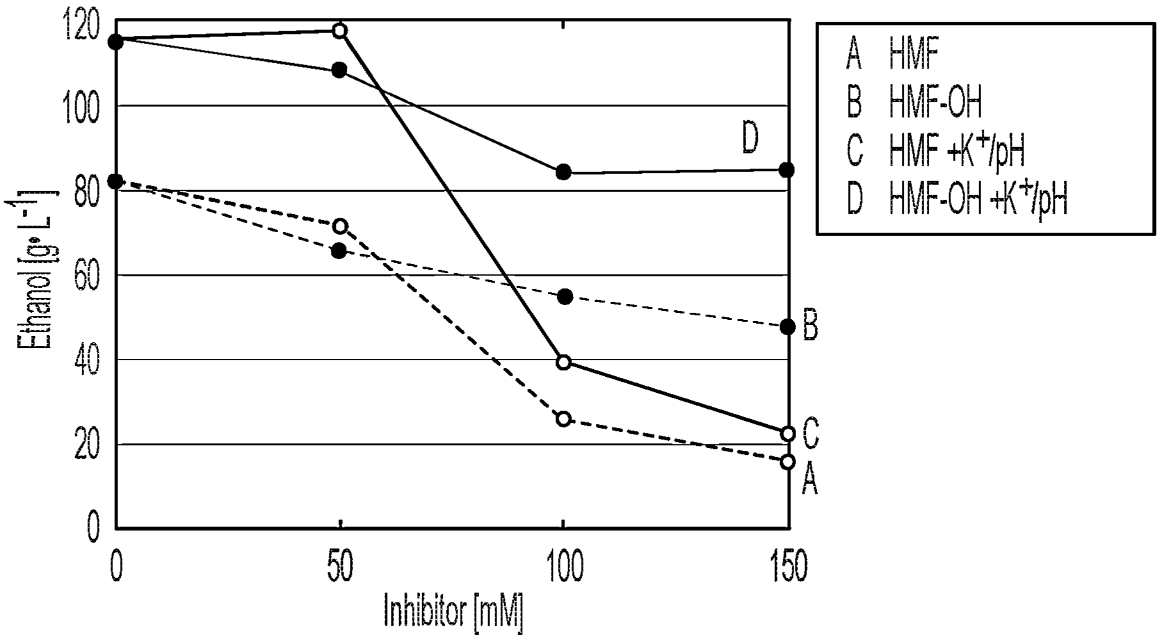

Inhibitor supplementation for the additionally screened conditions in FIGS. 2A-2C were: 50/60 mM acetic acid/NHCl, 50/50/60 mM acetic acid/KCl/$NH_4OH$, 150/180 mM acetic acid/$NH_4Cl$, 150/50/180 mM acetic acid/KCl/$NH_4OH$, 50/9 mM furfural/$NH_4Cl$, 50/50/9 mM furfural/KCl/$NH_4OH$, 50/6 mM FF—OH/NHCl, 50/50/6 mM FF—OH/KCl/$NH_4OH$, 150/15 mM furfural/$NH_4Cl$. 150/50/15 mM furfural/KCl/$NH_4OH$, 150/9 mM FF—OH/$NH_4Cl$, 150/50/9 mM FF—OH/KCl/$NH_4OH$, 50/6 mM HMF/NHCl, 50/50/6 mM HMF/KCl/$NH_4OH$, 50/6 mM HMF-OH/$NH_4Cl$, 50/50/6 mM HMF-OH/KCl/$NH_4OH$, 150/11 mM HMF/$NH_4Cl$, 150/50/11 mM HMF/KCl/$NH_4OH$, 150/9 mM HMF-OH/NHCl, or 150/50/9 mM HMF-OH/KCl/$NH_4OH$. The "/" notation is used for visual abbreviation but indicates the addition of all components during preparation. All $NH_4OH$ concentrations were pre-determined to be the amounts needed to achieve pH 6; the same concentration of $NH_4Cl$ was supplemented to the inhibitor-only condition to control for ammonium addition (that said, prior experience has shown that yeast can tolerate at least 200 mM $NH_4Cl$ with no detectable changes on ethanol titer). Furfural (Sigma-Aldrich #185914), HMF (Sigma-Aldrich #H40807), FF—OH (Sigma-Aldrich #W249106), and HMF-OH (Santa Cruz Biotechnology #sc-210242, scbt.com) were added directly to media in their supplier, concentrated forms to minimize the addition of volume. Despite the highly nonpolar nature of furfural and HMF, significant agitation during media preparation was sufficient to solubilize these components such that amounts added and those quantified from HPLC were in agreement. Fermentation samples of 550 μL were harvested after 48 h, cells removed by centrifugation (16,870×g, 2 min), and supernatants 0.45 μm syringe-filtered (Fisher Scientific #50-109-8735, fishersci.com) into glass HPLC vials and stored at 4° C. until analysis. Similarly, pre-inoculation fermentation media were syringe-filtered and diluted 1:5 in water for HPLC verification of starting glucose and inhibitor concentrations.

To screen the panel of over-expressed reductases on fermentation (FIG. 3), strains LAMy312, 553, 579, 580, 589 were started in YSC-Leu containing 180 g/L glucose and diluted for further acclimation overnight to higher glucose in YSC-Leu containing 240 g/L glucose. Upon reaching $OD_{600}$=2.5-3, 100 $OD_{600}$ units of cells were harvested, and cell pellets resuspended in 4 mL of YSC-Leu containing 260 g/L glucose, 62/48/100 mM furfural/HMF/acetic acid, and 60/140 mM $KHCO_3$/$CaCO_3$. A second set of cell pellets was resuspended in 4 mL of YSC-Leu containing 240 g/L glucose, 84/64/133 mM furfural/HMF/acetic acid, and 60/200 mM $KHCO_3$/$CaCO_3$. Cell-free samples of the fermentation medium were harvested after 46 h per procedures described above for HPLC analysis.

To prepare samples for mass spectrometric quantification of furfural, HMF, FF—OH, and HMF-OH (FIG. 1B), strains LAMy312, 579 were started in YSC-Leu containing 180 g/L glucose and diluted for further acclimation overnight to higher glucose in YSC-Leu containing 240 g/L glucose. Upon reaching $OD_{600}$=2.5-3, 100 $OD_{600}$ units of cells were harvested, and cell pellets resuspended in 4 mL of YSC-Leu containing 260 g/L glucose, 62/48/100 mM furfural/HMF/acetic acid, and 60/140 mM $KHCO_3$/$CaCO_3$. After 24 h of fermentation, 100 μL of supernatant from cell-pelleted samples was combined with 100 μL of 100% UHPLC-grade methanol containing isotopically labeled amino acids (provided by the Whitehead Institute Metabolite Profiling Core Facility), and mixtures stored at −80° C. until analysis. Similarly, 100 μL of syringe-filtered pre-inoculation fermentation medium was extracted to determine starting concentrations of inhibitors.

To assess the impact of GRE2 and increasing $K^+$ and pH conditions on cell viability under combined furan aldehyde stress (FIG. 1C; FIG. 4), strains LAMy312, 579, 629 were started in YSC-Leu containing 180 g/L glucose, diluted, and further acclimated overnight in YSC-Leu containing 260 g/L glucose. Upon reaching $OD_{600}$=2.5-3, 100 $OD_{600}$ units of cells were harvested, and cell pellets resuspended in 4 mL of YSC-Leu 601 containing 260 g/L glucose, 62/48 mM furfural/HMF, and supplemented with either (from 602 blue to red) 25 mM KCl, 5 mM $NH_4OH$, 10 mM $NH_4OH$, 15 mM $NH_4OH$, 20 mM $NH_4OH$, 24 mM $NH_4OH$, 24/25 mM $NH_4OH$/KCl, 24±5 mM $NH_4OH$+$NH_4OH$, 24±10 mM $NH_4OH$+$NH_4OH$, 24±15 mM $NH_4OH$+$NH_4OH$, or 24±20 mM $NH_4OH$+NHOH. As above, "/" indicates addition of components during preparation while the "+" here indicates addition after 22 h of fermentation. At 0, 24, 32, 52, and 71 h after inoculation, cell densities were measured, and 20 μL taken for immediate methylene blue viability staining and microscopy (FIG. 4). Pre-inoculation media and cell-free fermentation samples at 71 h were harvested for HPLC analysis.

To screen for a fermentation advantage conferred by over-expression of GRE2$^{evol}$ vs. GRE2 (FIG. 6A), prototrophic strains LAMy660, 661, 663 were started in minimal YNB medium (i.e., no amino acids) containing 100 g/L glucose and diluted for further acclimation overnight to higher glucose in 1.3×YNB containing 240 g/L glucose. Upon reaching $OD_{600}$=2.5-3, 100 $OD_{600}$ units of cells were harvested, and cell pellets resuspended in 4 mL of YSC-Leu containing 260 g/L glucose, 62/48/100 mM furfural/HMF/acetic acid, and 60/140 mM $KHCO_3$/$CaCO_3$. A second set of cell pellets was resuspended in 4 mL of YSC—Leu containing 280 g/L glucose, 62/48/100 mM furfural/HMF/acetic acid, and 60/140 mM $KHCO_3$/$CaCO_3$. A third set of cell pellets was resuspended in 4 mL of YSC-Leu containing 260 g/L glucose, 84/63/100 mM furfural/HMF/acetic acid, and 60/140 mM $KHCO_3$/$CaCO_3$. For FIG. 6B, LAMy660, 663 prepared and harvested in the same fashion were resuspended in 4 mL of YNB containing 260 g/L glucose, 62/48/100 mM furfural/HMF/acetic acid, and 60/200 mM KCl/$CaCO_3$. Here, due to the reduced acidity from the lack of amino acids in YNB, equimolar KCl was used in lieu of $KHCO_3$, and $CaCO_3$ consequently increased to 200 mM, to achieve a pH within range of that in equivalent YSC-Leu. For FIG. 6C, LAMy660, 663, 690, and 692 were started in YSC-Ura-Leu-His-Trp-Ade-Lys ("YSC-6 AA") dropout medium containing 100 g/L glucose, diluted, and further expanded overnight in YSC-6 AA containing 250 g/L glucose (LAMy660, 663) or 150 g/L glucose (LAMy690, 692). Upon reaching $OD_{600}$=2.5-3, 100 $OD_{600}$ units of LAMy660, 663 were harvested and cell pellets resuspended in 4 mL of YSC-Leu with 260 g/L glucose and 60/140 mM $KHCO_3$/$CaCO_3$. For LAMy690, 692, 90 $OD_{600}$ units were harvested and resuspended in 4 mL of YSC-Ura-Leu with 165 g/L glucose and 60/250 mM $KHCO_3$/$CaCO_3$. Cell-free samples of the fermentation medium were harvested after 40 h (FIG. 6A), 48 h (FIG. 6B), or 24 h (FIG. 6C) for HPLC analysis.

For assaying a fitness advantage conferred by GRE2$^{evol}$ vs. GRE2 over-expression (FIG. 1D), strains LAMy660, 661, 663 were started in YSC-6 AA medium containing 100 g/L glucose, diluted, and further expanded overnight in YSC-6 AA containing 250 g/L glucose. Upon reaching $OD_{600}$=2.5-3, 9 $OD_{600}$ units of cells were harvested, and cell pellets resuspended in 13.5 mL of YSC-6 AA containing 50 g/L glucose, 40/28/55 mM furfural/HMF/acetic acid, supplemental 50 mM KCl, and adjusted to pH 6 with $NH_4OH$. Cell densities were measured at 0, 24, 48.5, 51.5, 56, 65.5, 69, 72, 75.5, 79.5, 91, and 96.5 h after inoculation. Cell-free samples of the medium were collected at 0, 24, 48.5, 56, 65.5, 72, 79.5, and 96.5 h for determination of furfural and HMF concentrations by HPLC.

For the fermentation time courses of FIG. 7A, strains LAMy660, 663 were started in YSC-6 AA containing 100 g/L glucose, diluted, and further expanded overnight in YSC-6 AA containing 250 g/L glucose. Upon reaching $OD_{600}$=2.5-3, 100 $OD_{600}$ units of LAMy660 were harvested and cell pellets resuspended in 4 mL of YSC-Leu with 260 g/L glucose and either 60/140 mM $KHCO_3$/$CaCO_3$ (uninhibited control, Label A); 62/48/100 mM furfural/HMF/acetic acid and adjusted to pH 5 with $NH_4OH$ per bioethanol practices (inhibited control, Label B); or 62/48/100 mM furfural/HMF/acetic acid and 60/140 mM $KHCO_3$/$CaCO_3$ (Label C). This final condition, as well as that of the inhibited control (inhibitor trio adjusted to pH 5 with $NH_4OH$), was repeated with 100 $OD_{600}$ units of strain LAMy663 for direct comparison with LAMy660 (Label D and Label E, respectively). At 0, 16, 32, and 48 h after inoculation, cell-free samples of the fermentation medium were harvested for HPLC analysis.

To assess performance in genuine biomass feedstocks (FIG. 7B), strains LAMy660, 663 were started in YSC-Leu containing 100 g/L glucose, diluted, and further expanded overnight in YSC-Leu containing 250 g/L glucose. Upon reaching $OD_{600}$=2.5-3, 90 $OD_{600}$ units were harvested, and cell pellets resuspended in 4 mL of the 7 indicated lignocellulosic hydrolysates supplemented with 20 mM urea and modified as follows: in the minimally-altered control (Label A), $Ca(OH)_2$ was also added, if necessary, to achieve pH 5; in the inhibited control (Label B), feedstocks were toxified to the final concentrations of glucose, furfural, HMF, and acetic acid listed in Table 2 and adjusted to pH 5 with $Ca(OH)_2$ if needed; and in the toxification and $K^+$/pH-ameliorated condition (Label C), feedstocks were toxified identically but adjusted instead with $KHCO_3$, $CaCO_3$, and $Ca(OH)_2$ as listed in Table 2. These 3 conditions were fermented with LAMy660 and the final repeated with LAMy663 (Label D). The ordering and labeling of bars in FIG. 7B follow that of FIG. 7A. The "high concentration sugar syrup" nature of DMR corn stover as described by the provider was found in pilot experiments to be inhibitory to yeast (above-average concentrations of glucose and xylose were confirmed; Table 1); therefore, dilutions of 65-75% were necessary to enable fermentation (61). All supplements were added in the maximally concentrated forms available to minimize dilution of the original hydrolysate. The minimally-altered controls (Label A) for bagasse, wheat straw, *miscanthus*, and switchgrass hydrolysate were observed in preliminary experiments to be sufficiently low in available sugar and ethanol product inhibition such that ethanol was metabolized following the consumption of glucose. To maximize accuracy of titers, cell-free fermentation samples for HPLC analysis were harvested after 24 h in these 4 control conditions and 52 h in all remaining.

For demonstrating extensibility of hydrolysate tolerance to xylose-consuming strains (FIG. 11A), prototrophic strains LAMy419, 665 were started in YSC-6 AA containing 40 g/L xylose, diluted, and further expanded overnight in YSC-6 AA containing 100 g/L xylose. Upon reaching $OD_{600}$=2.5-3, 90 $OD_{600}$ units were harvested, and cell pellets resuspended in 4 mL of bagasse, high acid corn stover, or *miscanthus* hydrolysate (non-bold) supplemented with 20 mM urea and modified in the same order and manner as those described above for FIG. 7B: Label A contained the $Ca(OH)_2$ needed to achieve pH 5 and was fermented with LAMy419; Label B toxified to the conditions listed in Table 2 and fermented with LAMy419; Label C was toxified, $K^+$ and pH-adjusted to the conditions in Table 2 and fermented with LAMy419; and Label D was the same as Label C but fermented with LAMy665. Formulation and fermentation of synthetic medium (bold) was done in a manner to reflect genuine lignocellulosic hexose-pentose proportions but maintain the xylose metabolism that would be suppressed from catabolite repression. Specifically, LAMy419 was fermented in YSC-6 AA prepared with 50 g/L xylose, 150 g/L potato starch (Sigma-Aldrich #S2630), and either 60/140 mM $KHCO_3$/$CaCO_3$ (uninhibited control, Label A); 62/48/100 mM furfural/HMF/acetic acid and adjusted to pH 5 with $NH_4OH$ (inhibited control, Label B); or 62/48/100 mM furfural/HMF/acetic acid and 60/140 mM $KHCO_3$/$CaCO_3$ (Label C). The final condition was repeated with LAMy665 (Label D). For these 4 conditions, the harvested 90 $OD_{600}$ units were resuspended in 2.5 mL of medium and glucoamylase (Sigma-Aldrich #A7095) added at the following amounts and times: 333 μL at 0 h (+25 U/mL), 333 μL at 18 h. 666 μL at 24 h (+50 U/mL), and 666 μL at 36.5 h. Enzyme amounts and times of addition were pre-determined in pilot experiments to support the full consumption of xylose in the uninhibited control (FIG. 10). Fermentation media were prepared in the most concentrated form possible to minimize dilution from glucoamylase addition. Cell-free fermentation samples for HPLC analysis were harvested after 48 h for the uninhibited controls (Label A) to minimize ethanol loss to consumption and 72 h for the remaining conditions.

For demonstrating extensibility of hydrolysate tolerance to lactic acid-producing strains (FIG. 11B), prototrophic strains LAMy690, 692 were started in YSC-6 AA containing 100 g/L glucose, diluted, and further expanded overnight in YSC-6 AA containing 200 g/L glucose. Upon reaching $OD_{600}$=2.5-3, 90 $OD_{600}$ units of LAMy690 were harvested, and cell pellets resuspended in 4 mL of YSC-Ura-Leu (bold) with 160 g/L glucose and either 60/250 mM $KHCO_3$/$CaCO_3$ (uninhibited control, Label A); 62/48/100 mM furfural/HMF/acetic acid and adjusted to pH 5 with $NH_4OH$ (inhibited control, Label B); or 62/48/100 mM furfural/HMF/acetic acid and 60/270 mM $KHCO_3$/$CaCO_3$ (Label C). The final condition was repeated with LAMy692 (Label D). Cell-free fermentation samples for HPLC analysis were harvested after 24 h for the uninhibited control (observed in pilot experiments to have had all glucose consumed) and 72 h for toxified conditions. For production from genuine hydrolysates, 90 $OD_{600}$ units of LAMy690 (Label A, Label B, Label C conditions) or LAMy692 (Label D) were resuspended in 4 mL of 65% DMR corn stover, low acid corn stover, or wheat straw hydrolysate (non-bold) supplemented with 20 mM urca and modified largely in the same order and manner as those described for FIG. 11A: Label A additionally contained 280 mM, 200 mM, or 120 mM $CaCO_3$, respectively, to buffer lactic acid accumulation; Label B toxified to the conditions listed in Table 2; and Label C and Label D were toxified, $K^+$ and pH-buffered to the conditions in Table 2. Cell-free fermentation samples for HPLC analysis were harvested after 24 h (wheat straw, Label A) or 48 h (DMR and low acid corn stover, Label A) for the uninhibited controls (observed in pilot experiments to have had all glucose consumed) and after 72 h for toxified conditions.

Directed Evolution of GRE2

The PCR-mutagenized GRE2 yeast library was revived from the "functional variomics" collection (gift of Xuewen Pan of Baylor University) in YSC-Ura containing 30 g/L glucose and supplemental 10 mM $KH_2PO_4$ (36). To maintain the >$2\times10^5$ diversity, 20 μL of thawed cells were expanded to saturation, diluted, and cultured overnight in fresh medium to approximately $OD_{600}$=2.5. Cell biomass totaling 3.5 $OD_{600}$ units was harvested and resuspended in 4 mL of YSC-Ura containing 30 g/L glucose, 32/25/52 mM furfural/HMF/acetic acid, supplemental 10 mM $KH_2PO_4$, and adjusted to pH 6 with $NH_4OH$. Following the time course of FIG. 5, cell densities reaching $OD_{600}$ values of 5-8 were sub-cultured in identically formulated YSC-Ura medium containing the indicated combinations of inhibitors. A 1 mL aliquot of the final culture was harvested for isolation of bulk DNA and the remaining mixed to 15% glycerol for preservation at −80° C.

Several attempts were required to converge on the conditions used in the successful iteration depicted in FIG. 5. For example, the 62/48/100 mM furfural/HMF/acetic acid combination used as a fermentation benchmark was determined to be growth suppressive even when pH-adjusted to neutralize acetic acid. A reduction to 30/24/50 mM furfural/HMF/acetic acid provided baseline growth-permissive conditions; however, increments of 5-10% of each inhibitor at the first sub-culturing ended in suppression. Given these responses, it was hypothesized that prolonging stress combinations over multiple expansion cycles was needed to allow stronger mutants to entrench within the population and seed further advantageous trajectories. Finally, that the hyper-tolerant $GRE2^{P48S+I290V+D133D}$ mutant was capable of conferring an improvement to fermentation under the benchmark suite of inhibitors (FIG. 7A), yet still unable to demonstrate growth under the same conditions (FIG. 12), underscored the divergence in tolerance thresholds between metabolic and biomass production.

The coding sequence for the $GRE2^{P48S+I290V+D133D}$ allele is as follows:

(SEQ ID NO: 7)

```
ATGTCAGTTTTCGTTTCAGGTGCTAACGGGTTCATTGCCCAACACATTGT
CGATCTCCTGTTGAAGGAAGACTATAAGGTCATCGGTTCTGCCAGAAGTC
AAGAAAAGGCCGAGAATTTAACGGAGGCCTTTGGTAACAACTCAAAATTC
TCCATGGAAGTTGTCCCAGACATATCTAAGCTGGACGCATTTGACCATGT
TTTCCAAAAGCACGGCAAGGATATCAAGATAGTTCTACATACGGCCTCTC
CATTCTGCTTTGATATCACTGACAGTGAACGCGATTTATTAATTCCTGCT
GTGAACGGTGTTAAGGGAATTCTCCACTCAATTAAAAAATACGCCGCTGA
TTCTGTAGAACGTGTAGTTCTCACCTCTTCTTATGCAGCTGTGTTCGACA
TGGCAAAAGAAAACGATAAGTCTTTAACATTTAACGAAGAATCCTGGAAC
CCAGCTACCTGGGAGAGTTGCCAAAGTGACCCAGTTAACGCCTACTGTGG
TTCTAAGAAGTTTGCTGAAAAAGCAGCTTGGGAATTTCTAGAGGAGAATA
GAGACTCTGTAAAATTCGAATTAACTGCCGTTAACCCAGTTTACGTTTTT
GGTCCGCAAATGTTTGACAAAGATGTGAAAAAACACTTGAACACATCTTG
CGAACTCGTCAACAGCTTGATGCATTTATCACCAGAGGACAAGATACCGG
AACTATTTGGTGGATACATTGATGTTCGTGATGTTGCAAAGGCTCATTTA
GTTGCCTTCCAAAAGAGGGAAACAATTGGTCAAAGACTAATCGTATCGGA
GGCCAGATTTACTATGCAGGATGTTCTCGATATCCTTAACGAAGACTTCC
CTGTTCTAAAAGGCAATGTTCCAGTGGGGAAACCAGGTTCTGGTGCTACC
CATAACACCCTTGGTGCTACTCTTGATAATAAAAAGAGTAAGAAATTGTT
```

-continued

```
AGGTTTCAAGTTCAGGAACTTGAAAGAGACCATTGACGACACTGCCTCCC
AAATTTTAAAATTTGAGGGCAGAATATAA
```

Chromatography

Quantification of ethanol, lactic acid, glucose, xylose, glycerol, furfural, HMF, and acetic acid was performed on cell-free, 0.45 μm-filtered samples using an Agilent 1200 Infinity Series HPLC configured with G1362A Refractive Index Detector and Aminex HPX-87H carbohydrate analysis column (Bio-Rad #125-0140, bio-rad.com). Analytes were separated isocratically in 5 mM sulfuric acid at 65° C. using a flow rate of 0.6 m/min. Under these conditions, retention times were approximately as follows: glucose 9.2 min, xylose 9.9 min, lactic acid 13.1 min, glycerol 13.8 min, acetic acid 15.3 min, ethanol 22.3 min, HMF 30.2 min, and furfural 45.0 min. Chromatogram peaks auto-integrated by the Agilent OpenLab CDS ChemStation software were converted to concentrations through interpolation off standard curves calibrated over the ranges of 0-100 g/L glucose, 0-50 g/L xylose, 0-100 g/L lactic acid, 0-8 g/L glycerol, 0-60 g/L acetic acid, 0-150 g/L ethanol, 0-8 g/L HMF, and 0-8 g/L furfural defined from chemically-pure dilution series. To compensate for the minor overlap between the peaks for glucose and xylose, standards were employed incorporating the two sugars at a ratio of 3:1 g/L glucose:xylose to reflect typical proportions. Likewise, lactic acid and glycerol standards incorporated 10:1 g/L lactic acid:glycerol.

Given the likelihood of calcium salts precipitating from the low pH in the running solvent and obstructing instrument fluidic lines, all samples derived from calcium-containing fermentations were acidified with 1% sulfuric acid (vol/vol), rotated for ≥1 h at 4° C., precipitates removed via centrifugation, and supernatants 0.45 μm-filtered before HPLC analysis.

Mass Spectrometry

For targeted quantification of furfural, FF—OH, HMF, and HMF-OH, cell-free samples collected from fermentation were extracted 1:1 with 100% UHPLC-grade methanol containing seventeen 13C labeled amino acids (Cambridge Isotope Laboratories, isotope.com) added as internal standards, and stored at −80° C. for further processing. Amino acid-methanol extraction buffer, downstream method development, and analysis were provided by the Metabolite Profiling Core Facility at the Whitehead Institute (metabolomics.wi.mit.edu).

In brief, additional dilutions to 1:20 and 1:80 (final) in 50% methanol were required to reach the linear range of the spectrometer. Samples of 1 μL were injected into a Dionex UltiMate 3000 ultra-high performance liquid chromatography (UPLC) unit equipped with an Ascentis Express C18 (2.1×150 mm, 2.7 μm particle) column (Sigma-Aldrich #53825-U) maintained at 35° C. Analytes were reverse phase separated at a flow rate of 0.25 mL/min using buffers A (0.1% formic acid in LCMS grade water) and B (0.1% formic acid in LCMS grade acetonitrile) under the following gradient conditions: 0-2 min (5% B); 2-20 min (5-75% B. linear gradient); 20.1-24 min (95% B); 24.1-28 min (5% B). Mass analysis was performed on a Thermo Scientific QExactive Orbitrap operating with a spray voltage of 3.0 kV, capillary temperature 275° C., HESI probe temperature 350° C., sheath gas flow 40 units, auxiliary gas flow 15 units, and sweep gas flow 1 unit. For targeted isolation of furfural, HMF, FF—OH, and HMF-OH, positive ionization mode was used with resolution set to 70,000, automatic gain control to $1×10^5$ with maximum injection time of 250 ms, and isolation window to 4.0 m/z. Fragmentation patterns from MS/MS were matched with reference spectra available in the METLIN online database (metlin.scripps.edu). Quantification was performed using the Thermo Scientific Xcalibur™ Software calibrated against chemically-pure dilution series of 3 μM-3 mM furfural, 30 μM-3 mM FF—OH, 0.1 μM-3 mM HMF, and 30 μM-3 mM HMF-OH.

For measurement of salt concentrations in hydrolysates, 10 mL of each sample was centrifuged (3,500×g, 5 min) to remove large particulates, and the supernatants submitted to Environmental Testing & Research Laboratories (ctrlabs.com) for quantification of K+ and $Ca^{2+}$ (available as components of their water testing suite). Acid-digested samples were assayed in three replicate reads by inductively coupled plasma mass spectrometry.

Viability Measurements

Yeast population viabilities measured via methylene blue staining and subsequent procedures to calculate correlation with ethanol titers described previously (16).

Statistical Analysis

Calculation of standard deviation (SD), propagation of error, hypothesis testing (two-sample, two-tailed t-test, $\alpha$=0.05), and p-value determination were performed using MATLAB (The Math Works, mathworks.com) on independent biological triplicates following standard procedures.

REFERENCES

1. C. McKerracher, A. Izadi-Najafabadi, A. O'Donovan, N. Albanese, N. Soulopoulous, D. Doherty, M. Boers, R. Fisher, C. Cantor, J. Frith, S. Mi, A. Grant, "Electric Vehicle Outlook 2020," Bloomberg New Energy Finance (Bloomberg Finance L.P., 2020), (available at about.bnef.com/electric-vehicle-outlook).
2. S. Davis, R. G. Boundy, "Transportation Energy Data Book: Edition 38" (ORNL/TM-2019/1333, Oak Ridge National Lab. (ORNL), Oak Ridge, TN (United States), 2020), doi: 10.2172/1606919.
3. Y. M. Bar-On, R. Phillips, R. Milo, The biomass distribution on Earth. Proc Natl Acad Sci USA. 115, 6506-6511 (2018).
4. M. H. Langholtz, B. J. Stokes, L. M. Eaton, "2016 Billion-Ton Report: Advancing Domestic Resources for a Thriving Bioeconomy" (10.2172/1271651, 2016), (available at energy.gov/eere/bioenergy/2016-billion-ton-report).
5. W.-C. Wang, L. Tao, J. Markham, Y. Zhang, E. Tan, L. Batan, E. Warner, M. Biddy, "Review of Biojet Fuel Conversion Technologies" (NREL/TP-5100-66291, 1278318, 2016), p. NREL/TP-5100-66291, 1278318, doi: 10.2172/1278318.
6. N. W. Y. Ho, M. R. Ladisch, M. Sedlak, N. S. Mosier, E. Casey, in Comprehensive Biotechnology (Second Edition), M. Moo-Young, Ed. (Elsevier B.V., 2011; sciencedirect.com/science/article/pii/B9780080885049001550), vol. 3, pp. 51-62.
7. L. J. Jönsson, B. Alriksson, N. O. Nilvebrant, Bioconversion of lignocellulose: inhibitors and detoxification. Biotechnol Biofuels (2013) (available at biomedcentral.com/content/pdf/1754-6834-6-16.pdf).
8. E. C. van der Pol, R. R. Bakker, P. Baets, G. Eggink, By-products resulting from lignocellulose pretreatment and their inhibitory effect on fermentations for (bio) chemicals and fuels. Appl Microbiol Biotechnol. 98, 9579-9593 (2014).
9. L. R. Lynd, The grand challenge of cellulosic biofuels. Nature Biotechnology. 35, 912-915 (2017).
10. N. Ali, Q. Zhang, Z.-Y. Liu, F.-L. Li, M. Lu, X.-C. Fang, Emerging technologies for the pretreatment of lignocellulosic materials for bio-based products. Appl Microbiol Biotechnol. 104, 455-473 (2020).
11. N. Mosier, C. Wyman, B. Dale, R. Elander, Y. Y. Lee, M. Holtzapple, M. Ladisch, Features of promising technologies for pretreatment of lignocellulosic biomass. Bioresour Technol. 96, 673-686 (2005).
12. J. T. Cunha, A. Romaní, C. E. Costa, I. Sá-Correia, L. Domingues, Molecular and physiological basis of *Saccharomyces cerevisiae* tolerance to adverse lignocellulose-based process conditions. Appl Microbiol Biotechnol. 103, 159-175 (2019).
13. F. K. Kazi, J. A. Fortman, R. P. Anex, D. D. Hsu, A. Aden, A. Dutta, G.
Kothandaraman, Techno-economic comparison of process technologies for biochemical ethanol production from corn stover. Fuel. 89, S20-S28 (2010).
14. J. K. Ko, Y. Um, Y.-C. Park, J.-H. Seo, K. H. Kim, Compounds inhibiting the bioconversion of hydrothermally pretreated lignocellulose. Appl Microbiol Biotechnol. 99, 4201-4212 (2015).
15. J. R. Almeida, T. Modig. A. Petersson, B. Hahn-Hägerdal, G. Lidén, M. F. Gorwa-Grauslund, Increased tolerance and conversion of inhibitors in lignocellulosic hydrolysates by *Saccharomyces cerevisiae*. J. Chem. Technol. Biotechnol. 82, 340-349 (2007).
16. F. H. Lam, A. Ghaderi, G. R. Fink, G. Stephanopoulos, Biofuels. Engineering alcohol tolerance in yeast. Science. 346, 71-75 (2014).
17. H. B. Klinke, A. B. Thomsen, B. K. Ahring, Inhibition of ethanol-producing yeast and bacteria by degradation products produced during pre-treatment of biomass. Appl Microbiol Biotechnol. 66, 10-26 (2004).
18. D. Heer, U. Sauer, Identification of furfural as a key toxin in lignocellulosic hydrolysates and evolution of a tolerant yeast strain. Microb Biotechnol. 1, 497-506 (2008).
19.
Y. H. Jung. I. J. Kim, H. K. Kim, K. H. Kim, Dilute acid pretreatment of lignocellulose for whole slurry ethanol fermentation. Bioresour Technol. 132, 109-114 (2013).
20. E. Palmqvist, B. Hahn-Hägerdal, Fermentation of lignocellulosic hydrolysates. II: inhibitors and mechanisms of inhibition. Bioresource Technology. 74, 25-33 (2000).
21. S. Larsson, E. Palmqvist, B. Hahn-Hägerdal, C. Tengborg, K. Stenberg, G. Zacchi, N.-O. Nilvebrant, The generation of fermentation inhibitors during dilute acid hydrolysis of softwood. Enzyme Microb. Technol. 24, 151-159 (1999).
22. T. Y. Mills, N. R. Sandoval, R. T. Gill, Cellulosic hydrolysate toxicity and tolerance mechanisms in *Escherichia coli*. Biotechnol Biofuels. 2 (2009), doi: doi.org/10.1186/17546834-2-26.
23. M. P. Almario, L. H. Reyes, K. C. Kao, Evolutionary engineering of *Saccharomyces cerevisiae* for enhanced tolerance to hydrolysates of lignocellulosic biomass. Biotechnol Bioeng. 110, 2616-2623 (2013).
24. C. B. Brachmann, A. Davies, G. J. Cost, E. Caputo, J. Li, P. Hieter, J. D. Boeke, Designer deletion strains derived from *Saccharomyces cerevisiae* S288C: a useful set of strains and plasmids for PCR-mediated gene disruption and other applications. Yeast. 14, 115-132 (1998).
25. S. A. Allen, W. Clark, J. M. McCaffery, Z. Cai, A. Lanctot, P. J. Slininger, Z. L. Liu, S. W. Gorsich, Furfural induces reactive oxygen species accumulation and cellular damage in *Saccharomyces cerevisiae*. Biotechnol Biofuels. 3, 2 (2010).

26. E. Casey, M. Sedlak, N. W. Y. Ho, N. S. Mosier, Effect of acetic acid and pH on the cofermentation of glucose and xylose to ethanol by a genetically engineered strain of *Saccharomyces cerevisiae*. FEMS Yeast Res. 10, 385-393 (2010).
27. M. J. Taherzadeh, L. Gustafsson, C. Niklasson, G. Lidén, Conversion of furfural in aerobic and anaerobic batch fermentation of glucose by *Saccharomyces cerevisiae*. J. Biosci. Bioeng. 87, 169-174 (1999).
28. J. R. M. Almeida, A. Röder, T. Modig, B. Laadan, G. Lidén, M. F. Gorwa-Grauslund, NADH-vs NADPH-coupled reduction of 5-hydroxymethyl furfural (HMF) and its implications on product distribution in *Saccharomyces cerevisiae*. Appl Microbiol Biotechnol. 78, 939-945 (2008).
29. D. Heer, D. Heine, U. Sauer, Resistance of *Saccharomyces cerevisiae* to high concentrations of furfural is based on NADPH-dependent reduction by at least two oxireductases. Appl Environ Microbiol. 75, 7631-7638 (2009).
30. Z. Lewis Liu, J. Moon, B. J. Andersh, P. J. Slininger, S. Weber, Multiple gene-mediated NAD(P)H-dependent aldehyde reduction is a mechanism of in situ detoxification of furfural and 5-hydroxymethylfurfural by *Saccharomyces cerevisiae*. Appl Microbiol Biotechnol. 81, 743-753 (2008).
31. J. Moon, Z. L. Liu, Engineered NADH-dependent GRE2 from *Saccharomyces cerevisiae* by directed enzyme evolution enhances HMF reduction using additional cofactor NADPH. Enzyme Microb. Technol. 50, 115-120 (2012).
32. A. Petersson, J. R. M. Almeida, T. Modig, K. Karhumaa, B. Hahn-Hägerdal, M. F. Gorwa-Grauslund, G. Liden, A 5-hydroxymethyl furfural reducing enzyme encoded by the *Saccharomyces cerevisiae* ADH6 gene conveys HMF tolerance. Yeast. 23, 455-464 (2006).
33. M. Ma, X. Wang, X. Zhang, X. Zhao, Alcohol dehydrogenases from Scheffersomyces *stipitis* involved in the detoxification of aldehyde inhibitors derived from lignocellulosic biomass conversion. Appl Microbiol Biotechnol. 97, 8411-8425 (2013).
34. E. R. Jerison, A. N. Nguyen Ba, M. M. Desai, S. Kryazhimskiy, Chance and necessity in the pleiotropic consequences of adaptation for budding yeast. Nat Ecol Evol. 4, 601-611 (2020).
35. W. Qian, D. Ma, C. Xiao, Z. Wang, J. Zhang. The Genomic Landscape and Evolutionary Resolution of Antagonistic Pleiotropy in Yeast. Cell Reports. 2, 1399-1410 (2012).
36. Z. Huang, K. Chen, J. Zhang, Y. Li, H. Wang, D. Cui, J. Tang, Y. Liu, X. Shi, W. Li, D. Liu, R. Chen, R. S. Sucgang. X. Pan, A functional variomics tool for discovering drug-resistance genes and drug targets. Cell Rep. 3, 577-585 (2013).
37. S. H. Mohd Azhar, R. Abdulla, S. A. Jambo, H. Marbawi, J. A. Gansau, A. A. Mohd Faik, K. F. Rodrigues, Yeasts in sustainable bioethanol production: A review. Biochemistry and Biophysics Reports. 10, 52-61 (2017).
38. X. Chen, E. Kuhn, E. W. Jennings, R. Nelson, L. Tao, M. Zhang, M. P. Tucker, DMR (deacetylation and mechanical refining) processing of corn stover achieves high monomeric sugar concentrations (230 g L-1) during enzymatic hydrolysis and high ethanol concentrations (>10% v/v) during fermentation without hydrolysate purification or concentration. Energy & Environmental Science. 9, 1237-1245 (2016).
39. L. Tao, D. Schell, R. Davis, E. Tan, R. Elander, A. Bratis, "NREL 2012 Achievement of Ethanol Cost Targets: Biochemical Ethanol Fermentation via Dilute-Acid Pretreatment and Enzymatic Hydrolysis of Corn Stover" (NREL/TP-5100-61563, 1129271, 2014), p.NREL/TP-5100-61563, 1129271, doi: 10.2172/1129271.
40. B. Zhang, H. Sun, J. Li, Y. Wan, Y. Li, Y. Zhang, High-titer-ethanol production from cellulosic hydrolysate by an engineered strain of *Saccharomyces cerevisiae* during an in situ removal process reducing the inhibition of ethanol on xylose metabolism. Process Biochemistry. 51, 967-972 (2016).
41. M. W. Lau, B. E. Dale, Cellulosic ethanol production from AFEX-treated corn stover using *Saccharomyces cerevisiae* 424A(LNH-ST). PNAS. 106, 1368-1373 (2009).
42. X. Liu, H. Liu, P. Yan, L. Mao, Z. Xu, Z. C. Zhang, Mechanocatalytic Synergy for Expedited Cellulosic Ethanol Production Compatible with Integrated Biorefinery. ACS Sustainable Chem. Eng. 8, 2399-2408 (2020).
43. S. M. O'Rourke, I. Herskowitz, Unique and redundant roles for HOG MAPK pathway components as revealed by whole-genome expression analysis. Mol Biol Cell. 15, 532-542 (2004).
44. J. C. Varela, C. van Beekvelt, R. J. Planta, W. H. Mager, Osmostress-induced changes in yeast gene expression. Mol Microbiol. 6, 2183-2190 (1992).
45. A. P. Capaldi, T. Kaplan, Y. Liu, N. Habib, A. Regev, N. Friedman, E. K. O'Shea, Structure and function of a transcriptional network activated by the MAPK Hog1. Nat Genet. 40, 1300-1306 (2008).
46. H. Zhou, J.-S. Cheng, B. L. Wang, G. R. Fink, G. Stephanopoulos, Xylose isomerase overexpression along with engineering of the pentose phosphate pathway and evolutionary engineering enable rapid xylose utilization and ethanol production by *Saccharomyces cerevisiae*. Metab Eng. 14, 611-622 (2012).
47. Global Lactic Acid Market Size & Share Report, 2019-2025, (available at grandviewresearch.com/industry-analysis/lactic-acid-and-poly-lactic-acid-market).
48. D. A. Abbott, R. M. Zelle, J. T. Pronk, A. J. A. van *Maris*, Metabolic engineering of *Saccharomyces cerevisiae* for production of carboxylic acids: current status and challenges. FEMS Yeast Res. 9, 1123-1136 (2009).
49. M. T. Flikweert, L. Van Der Zanden, W. M. Janssen, H. Y. Steensma, J. P. van Dijken, J. T. Pronk, Pyruvate decarboxylase: an indispensable enzyme for growth of *Saccharomyces cerevisiae* on glucose. Yeast. 12, 247-257 (1996).
50. H. Alper, C. Fischer, E. Nevoigt, G. Stephanopoulos, Tuning genetic control through promoter engineering. Proc Natl Acad Sci USA. 102, 12678-12683 (2005).
51. S. Hohmann, Characterization of PDC6, a third structural gene for pyruvate decarboxylase in *Saccharomyces cerevisiae*. J Bacteriol. 173, 7963-7969 (1991).
52. S.-H. Baek, E. Y. Kwon, Y. H. Kim, J.-S. Hahn, Metabolic engineering and adaptive evolution for efficient production of D-lactic acid in *Saccharomyces cerevisiae*. Appl Microbiol Biotechnol. 100, 2737-2748 (2016).
53. T. L. Turner, G.-C. Zhang, E. J. Oh, V. Subramaniam, A. Adiputra, V. Subramaniam, C. D. Skory. J. Y. Jang. B. J. Yu, I. Park, Y.-S. Jin, Lactic acid production from cellobiose and xylose by engineered *Saccharomyces cerevisiae*. Biotechnology and Bioengineering. 113, 1075-1083 (2016).

54. N. Ishida, S. Saitoh, T. Onishi, K. Tokuhiro, E. Nagamori, K. Kitamoto, H. Takahashi, The effect of pyruvate decarboxylase gene knockout in *Saccharomyces cerevisiae* on L-lactic acid production. Biosci Biotechnol Biochem. 70, 1148-1153 (2006).
55. A. L. Walter, D. Yang, Z. Zeng, D. Bayrock, P. E. Urriola, G. C. Shurson, Assessment of antibiotic resistance from long-term bacterial exposure to antibiotics commonly used in fuel ethanol production. World J Microbiol Biotechnol. 35, 66 (2019).
56. D. Mumberg, R. Müller, M. Funk, Yeast vectors for the controlled expression of heterologous proteins in different genetic backgrounds. Gene. 156, 119-122 (1995).
57. R. D. Gietz, R. H. Schiestl, A. R. Willems, R. A. Woods, Studies on the transformation of intact yeast cells by the LiAc/SS-DNA/PEG procedure. Yeast. 11, 355-360 (1995).
58. I. Herskowitz, R. E. Jensen, Putting the HO gene to work: practical uses for mating-type switching. Meth Enzymol. 194, 132-146 (1991).
59. G. F. Sprague, Assay of yeast mating reaction. Meth Enzymol. 194, 77-93 (1991).
60. V. K. Vyas, M. I. Barrasa, G. R. Fink, A *Candida albicans* CRISPR system permits genetic engineering of essential genes and gene families. Science Advances. 1, e1500248 (2015).
61. M. P. Tucker, High Titer and Yields Achieved with Novel, Low-Severity Pretreatment Strategy (2016), (available at nrel.gov/docs/fy16osti/65917.pdf).

Additional Embodiments

1. A genetically modified yeast cell (modified cell) comprising: a first exogenous gene operably linked to a promoter, wherein the first exogenous gene encodes an enzyme having methylglyoxal reductase (GRE2) activity.
2. The modified cell of Embodiment 1, wherein the enzyme having GRE2 activity is derived from *Saccharomyces cerevisiae*.
3. The modified cell of Embodiment 1 or Embodiment 2, wherein the enzyme having GRE2 activity comprises a sequence having at least 90% identity to the amino acid sequence set forth in SEQ ID NO: 1.
4. The modified cell of any one of Embodiments 1-3, wherein the enzyme having GRE2 activity comprises a sequence set forth in SEQ ID NO: 1.
5. The modified cell of any one of Embodiments 1-4, wherein the enzyme having GRE2 activity comprises at least one substitution mutation at a position corresponding to position P48, 1290, and/or D133, relative to SEQ ID NO: 1.
6. The modified cell of Embodiment 5, wherein the substitution mutation at the position corresponding to position P48 of SEQ ID NO: 1 is a mutation to serine.
7. The modified cell of Embodiment 5 or Embodiment 6, wherein the substitution mutation at the position corresponding to position 1290 of SEQ ID NO: 1 is a mutation to valine.
8. The modified cell of any one of Embodiments 5-7, wherein the substitution mutation at the position corresponding to position D133 of SEQ ID NO: 1 is a silent mutation that retains aspartate.
9. The modified cell of any one of Embodiments 1-8, wherein the promoter is selected from the group consisting of pTDH3, pTEF3, and pPDC1.
10. The modified cell of any one of Embodiments 1-9, wherein the yeast cell is of the genus *Saccharomyces*.
11. The modified cell of Embodiment 10, wherein the yeast cell is of the species *Saccharomyces cerevisiae*.
12. The modified cell of any one of Embodiments 1-11, wherein the yeast cell is modified to ferment xylose to ethanol in the absence of glucose.
13. The modified cell of any one of Embodiments 1-12, further comprising a second exogenous gene, wherein the second exogenous gene encodes an enzyme having D-lactate dehydrogenase (D-LDH) activity.
14. The modified cell of Embodiment 13, wherein the enzyme having D-LDH activity is derived from *Leuconostoc mesenteroides*.
15. The modified cell of Embodiment 13 or Embodiment 14, wherein the enzyme having D-LDH activity comprises a sequence having at least 90% identity to the amino acid sequence set forth in SEQ ID NO: 2.
16. The modified cell of any one of Embodiments 13-15, wherein the enzyme having D-LDH activity comprises a sequence set forth in SEQ ID NO: 2.
17. A method of producing biofuel from toxic biomass comprising:

contacting the modified cell of any one of Embodiments 1-16 with a medium comprising a potassium salt and a pH modulator.

18. The method of Embodiment 17, wherein the biofuel is ethanol.
19. The method of Embodiment 17 or Embodiment 18, wherein the potassium salt is selected from potassium phosphate monobasic ($KH_2PO_4$), potassium bicarbonate ($KHCO_3$), potassium phosphate dibasic ($K_2HPO_4$), potassium chloride (KCl), potassium hydroxide (KOH), and potassium sulfate ($K_2SO_4$).
20. The method of Embodiment 19, wherein the potassium salt is $K_2HPO_4$.
21. The method of any one of Embodiments 19-20, wherein the concentration of potassium salt in the medium is between about 15 mM to about 200 mM.
22. The method of Embodiment 21, wherein the concentration of potassium salt in the medium is about 50 mM.
23. The method of any one of Embodiments 17-22, wherein the pH modulator is selected from potassium hydroxide (KOH), potassium phosphate dibasic ($K_2HPO_4$), and calcium carbonate ($CaCO_3$).
24. The method of Embodiment 23, wherein the pH modulator is $CaCO_3$.
25. The method of Embodiment 24, wherein the $CaCO_3$ is in an amount sufficient to maintain, in culture medium, a pH of at least 3.5.

EQUIVALENTS

Those skilled in the art will recognize or be able to ascertain using no more than routine experimentation, many equivalents to the specific embodiments of the invention described here. Such equivalents are intended to be encompassed by the following claims.

All references, including patent documents, are incorporated by reference in their entirety.

What is claimed is:

1. A genetically modified yeast cell comprising:

a first exogenous gene operably linked to a promoter, wherein the first exogenous gene encodes an enzyme having methylglyoxal reductase (GRE2) activity comprising the sequence of SEQ ID NO: 1 with a P48S and 1290V mutation, relative to SEQ ID NO: 1.

2. The genetically modified yeast cell of claim 1, wherein the promoter is selected from the group consisting of pTDH3, pTEF3, and pPDC1.

3. The genetically modified yeast cell of claim 2, wherein the genetically modified yeast cell is of the genus *Saccharomyces.*

4. The genetically modified yeast cell of claim 3, wherein the genetically modified yeast cell is modified to ferment xylose to ethanol in the absence of glucose.

5. The genetically modified yeast cell of claim 3, further comprising a second exogenous gene, wherein the second exogenous gene encodes an enzyme having D-lactate dehydrogenase (D-LDH) activity comprising the sequence of SEQ ID NO: 2.

6. A method of producing biofuel from toxic biomass comprising:

contacting the genetically modified yeast cell of claim 1 with a medium comprising a potassium salt and a pH modulator.

7. The method of claim 6, wherein the biofuel is ethanol.

8. The method of claim 6, wherein the potassium salt is selected from potassium phosphate monobasic ($KH_2PO_4$), potassium bicarbonate ($KHCO_3$), potassium phosphate dibasic ($K_2HPO_4$), potassium chloride (KCl), potassium hydroxide (KOH), and potassium sulfate ($K_2SO_4$).

9. The method of claim 8, wherein the concentration of potassium salt in the medium is between about 15 mM to about 200 mM.

10. The method of claim 6, wherein the pH modulator is selected from potassium hydroxide (KOH), potassium phosphate dibasic ($K_2HPO_4$), and calcium carbonate ($CaCO_3$).

11. The method of claim 10, wherein the $CaCO_3$ is in an amount sufficient to maintain, in culture medium, a pH of at least 3.5.

12. The method of claim 8, wherein the potassium salt is $K_2HPO_4$.

13. The method of claim 9, wherein the concentration of potassium salt in the medium is about 50 mM.

14. The method of claim 10, wherein the pH modulator is $CaCO_3$.

15. The genetically modified yeast cell of claim 3, wherein the yeast cell is of the species *Saccharomyces cerevisiae.*

16. The genetically modified yeast cell of claim 1, wherein the first exogenous gene comprises the nucleotide sequence of SEQ ID NO: 7.

* * * * *

SEQUENCE LISTING

<160> NUMBER OF SEQ ID NOS: 7

<210> SEQ ID NO 1
<211> LENGTH: 342
<212> TYPE: PRT
<213> ORGANISM: Saccharomyces cerevisiae

<400> SEQUENCE: 1

Met Ser Val Phe Val Ser Gly Ala Asn Gly Phe Ile Ala Gln His Ile
1 5 10 15

Val Asp Leu Leu Leu Lys Glu Asp Tyr Lys Val Ile Gly Ser Ala Arg
20 25 30

Ser Gln Glu Lys Ala Glu Asn Leu Thr Glu Ala Phe Gly Asn Asn Pro
35 40 45

Lys Phe Ser Met Glu Val Val Pro Asp Ile Ser Lys Leu Asp Ala Phe
50 55 60

Asp His Val Phe Gln Lys His Gly Lys Asp Ile Lys Ile Val Leu His
65 70 75 80

Thr Ala Ser Pro Phe Cys Phe Asp Ile Thr Asp Ser Glu Arg Asp Leu
85 90 95

Leu Ile Pro Ala Val Asn Gly Val Lys Gly Ile Leu His Ser Ile Lys
100 105 110

Lys Tyr Ala Ala Asp Ser Val Glu Arg Val Val Leu Thr Ser Ser Tyr
115 120 125

Ala Ala Val Phe Asp Met Ala Lys Glu Asn Asp Lys Ser Leu Thr Phe
130 135 140

Asn Glu Glu Ser Trp Asn Pro Ala Thr Trp Glu Ser Cys Gln Ser Asp
145 150 155 160

Pro Val Asn Ala Tyr Cys Gly Ser Lys Lys Phe Ala Glu Lys Ala Ala
165 170 175

Trp Glu Phe Leu Glu Glu Asn Arg Asp Ser Val Lys Phe Glu Leu Thr
180 185 190

Ala Val Asn Pro Val Tyr Val Phe Gly Pro Gln Met Phe Asp Lys Asp
195 200 205

Val Lys Lys His Leu Asn Thr Ser Cys Glu Leu Val Asn Ser Leu Met
210 215 220

His Leu Ser Pro Glu Asp Lys Ile Pro Glu Leu Phe Gly Gly Tyr Ile
225 230 235 240

Asp Val Arg Asp Val Ala Lys Ala His Leu Val Ala Phe Gln Lys Arg
245 250 255

Glu Thr Ile Gly Gln Arg Leu Ile Val Ser Glu Ala Arg Phe Thr Met
260 265 270

Gln Asp Val Leu Asp Ile Leu Asn Glu Asp Phe Pro Val Leu Lys Gly
275 280 285

Asn Ile Pro Val Gly Lys Pro Gly Ser Gly Ala Thr His Asn Thr Leu
290 295 300

Gly Ala Thr Leu Asp Asn Lys Lys Ser Lys Lys Leu Leu Gly Phe Lys
305 310 315 320

Phe Arg Asn Leu Lys Glu Thr Ile Asp Asp Thr Ala Ser Gln Ile Leu
325 330 335

Lys Phe Glu Gly Arg Ile
340

<210> SEQ ID NO 2
<211> LENGTH: 331

-continued

```
<212> TYPE: PRT
<213> ORGANISM: Leuconostoc mesenteroides

<400> SEQUENCE: 2

Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

Glu Leu Leu Thr Pro Glu Thr Val Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Ile
            100                 105                 110

Gln Leu Ser Arg Leu Leu Arg Arg Thr Lys Ala Leu Asp Ala Lys Ile
        115                 120                 125

Ala Lys His Asp Leu Arg Trp Ala Pro Thr Ile Gly Arg Glu Met Arg
    130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
        195                 200                 205

Val Pro Glu Asn His His Leu Ile Asn Ala Glu Ala Ile Ala Lys Met
    210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Gly Leu Phe Asn Glu Asp Trp
            260                 265                 270

Ser Gly Lys Glu Phe Pro Asp Ala Lys Ile Ala Asp Leu Ile Ser Arg
        275                 280                 285

Glu Asn Val Leu Val Thr Pro His Thr Ala Phe Tyr Thr Thr Lys Ala
    290                 295                 300

Val Leu Glu Met Val His Gln Ser Phe Asp Ala Ala Val Ala Phe Ala
305                 310                 315                 320

Lys Gly Glu Lys Pro Ala Ile Ala Val Glu Tyr
                325                 330


<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3

tgctaagaac ccagttatct                                                 20
```

<210> SEQ ID NO 4
<211> LENGTH: 60
<212> TYPE: DNA
<213> ORGANISM: Artificial Sequence
<220> FEATURE:
<223> OTHER INFORMATION: Synthetic

<400> SEQUENCE: 4
cataatcaat ctcaaagaga acaacacaat acaataacaa gaagaacaaa gctaattaac 60

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ttctcgatca atatactgta 20

<210> SEQ ID NO 6
<211> LENGTH: 528
<212> TYPE: DNA
<213> ORGANISM: Artificial Sequence
<220> FEATURE:
<223> OTHER INFORMATION: Synthetic

<400> SEQUENCE: 6
caaaggtcgc gtttctttta gaaaaactaa tacgtaaacc tgcattaagg gaacaaaagc 60
tggagctcat agcttcaaaa cgcttctacc cccttttac tcttccagat tttctcggac 120
tccgcgcatc gccgtaccac ttcaagacac ccaagcacag catactaaat ttcccctctt 180
tcttcctcta gggtgtcgct aattacccgt actaaaggtt tggaaaagaa aaaagggacc 240
gcctcgtttc tttctcttcg tcgagagagg caataaaaat ttttatcacg tttctttttc 300
ttgagagttt ctttcttgat ttttttctct ttcgatgacc tcccattgat atttaagcta 360
ataaacggtc ttcaatttct caagcttcag tttcattttt cttgttctat tacaactttt 420
tttacttctt gctcgttaga gagaaagcat agcaatctaa tctaagtttt ctagaaaaat 480
gtctgaaata accttaggta aatatttatt tgaaagattg agccaagt 528

<210> SEQ ID NO 7
<211> LENGTH: 1029
<212> TYPE: DNA
<213> ORGANISM: Artificial Sequence
<220> FEATURE:
<223> OTHER INFORMATION: Synthetic

<400> SEQUENCE: 7
atgtcagttt tcgtttcagg tgctaacggg ttcattgccc aacacattgt cgatctcctg 60
ttgaaggaag actataaggt catcggttct gccagaagtc aagaaaaggc cgagaattta 120
acggaggcct ttggtaacaa ctcaaaattc tccatggaag ttgtcccaga catatctaag 180
ctggacgcat ttgaccatgt tttccaaaag cacggcaagg atatcaagat agttctacat 240
acggcctctc cattctgctt tgatatcact gacagtgaac gcgatttatt aattcctgct 300
gtgaacggtg ttaagggaat tctccactca attaaaaaat acgccgctga ttctgtagaa 360
cgtgtagttc tcacctcttc ttatgcagct gtgttcgaca tggcaaaaga aaacgataag 420
tctttaacat ttaacgaaga atcctggaac ccagctacct gggagagttg ccaaagtgac 480

-continued

| | |
|---|---|
| ccagttaacg cctactgtgg ttctaagaag tttgctgaaa aagcagcttg ggaatttcta | 540 |
| gaggagaata gagactctgt aaaattcgaa ttaactgccg ttaacccagt ttacgttttt | 600 |
| ggtccgcaaa tgtttgacaa agatgtgaaa aaacacttga acacatcttg cgaactcgtc | 660 |
| aacagcttga tgcatttatc accagaggac aagataccgg aactatttgg tggatacatt | 720 |
| gatgttcgtg atgttgcaaa ggctcattta gttgccttcc aaaagaggga aacaattggt | 780 |
| caaagactaa tcgtatcgga ggccagattt actatgcagg atgttctcga tatccttaac | 840 |
| gaagacttcc ctgttctaaa aggcaatgtt ccagtgggga aaccaggttc tggtgctacc | 900 |
| cataacaccc ttggtgctac tcttgataat aaaaagagta agaaattgtt aggtttcaag | 960 |
| ttcaggaact tgaaagagac cattgacgac actgcctccc aaattttaaa atttgagggc | 1020 |
| agaatataa | 1029 |